US009751939B2

(12) United States Patent
Steidl et al.

(10) Patent No.: US 9,751,939 B2
(45) Date of Patent: *Sep. 5, 2017

(54) ANTI-GM-CSF ANTIBODIES

(75) Inventors: Stefan Steidl, Munich (DE); Elisabeth Thomassen-Wolf, Gauting (DE)

(73) Assignee: Morphosys AG, Martinsried (DE)

( * ) Notice: Subject to any disclaimer, the term of this patent is extended or adjusted under 35 U.S.C. 154(b) by 160 days.

This patent is subject to a terminal disclaimer.

(21) Appl. No.: 12/923,363

(22) Filed: Sep. 16, 2010

(65) Prior Publication Data

US 2011/0045000 A1    Feb. 24, 2011

Related U.S. Application Data

(63) Continuation of application No. 11/914,599, filed as application No. PCT/EP2006/004696 on May 17, 2006, now Pat. No. 7,867,495.

(60) Provisional application No. 60/682,009, filed on May 18, 2005.

(51) Int. Cl.
*C07K 16/24* (2006.01)
*A61K 39/395* (2006.01)
*A61K 39/00* (2006.01)

(52) U.S. Cl.
CPC ...... *C07K 16/243* (2013.01); *A61K 2039/505* (2013.01); *C07K 2317/21* (2013.01); *C07K 2317/33* (2013.01); *C07K 2317/52* (2013.01); *C07K 2317/55* (2013.01); *C07K 2317/565* (2013.01); *C07K 2317/73* (2013.01); *C07K 2317/76* (2013.01); *C07K 2317/92* (2013.01); *C07K 2319/00* (2013.01)

(58) Field of Classification Search
CPC .............. C07K 16/243; C07K 2316/52; A61K 2039/505
USPC .................... 424/141.1; 530/387.3, 388.1
See application file for complete search history.

(56) References Cited

U.S. PATENT DOCUMENTS

| | | | |
|---|---|---|---|
| 5,530,101 A * | 6/1996 | Queen et al. ............... | 530/387.3 |
| 5,747,032 A | 5/1998 | Metcalf et al. | |
| 6,300,064 B1 | 10/2001 | Knappik et al. | |
| 7,427,401 B2 | 9/2008 | Lopez et al. | |
| 7,867,495 B2 * | 1/2011 | Steidl et al. ............... | 424/141.1 |

FOREIGN PATENT DOCUMENTS

| | | |
|---|---|---|
| WO | WO 97/08320 A | 3/1997 |
| WO | WO 03/068920 A2 | 8/2003 |
| WO | WO 2004/046330 A2 | 6/2004 |
| WO | WO 2005/105844 A2 | 11/2005 |

OTHER PUBLICATIONS

Lederman et al., Molecular Immunology, 1991, vol. 28, pp. 1171-1181.*
Li et al., Proc. Natl. Acad. Sci. USA, vol. 77, pp. 3211-3214.*
Alvaro-Gracia et al., "Cytokines in chronic inflammatory arthritis. VI. Analysis of the synovial cells involved in granulocyte-macrophage colony-stimulating factor production and gene expression in rheumatoid arthritis and its regulation by IL-1 and tumor necrosis factor-α," J Immunol., May 15, 1991, 146(10):3365-3371.
Babior, B., "Phagocytes and oxidative stress," Am. J. Med., Jul. 2000, 109:33-44.
Bonfield et al., "Anti-GM-CSF titer predicts response to GM-CSF therapy in pulmonary alveolar proteinosis," Clin. Immunol., Dec. 2002, 105(3):342-350.
Bozinovski et al., "Innate immune responses to lipopolysaccharide in mouse lung are suppressed and reversed by neutralization of GM-CSF via repression of TLR-4," Am. J. Physiol. Lung Cell Mol. Physiol., 2004, 286:L877-L885.
Broide et al., "Endobronchial allergen challenge in asthma. Demonstration of cellular source of granulocyte macrophage colony-stimulating factor by in situ hybridization," J. Clin. Invest., Sep. 1991, 88:1048-1053.
Broide et al., "Eosinophils express interleukin 5 and granulocyte macrophage-colony-stimulating factor mRNA at sites of allergic inflammation in asthmatics," J. Clin. Invest., Oct. 1992, 90:1414-1424.
Brown et al., "Mapping of human granulocyte-macrophage-colony-stimulating-factor domains interacting with the human granulocyte-macrophage-colony-stimulating-factor-receptor alpha-subunit," Eur. J. Biochem., 1994, 225:873-880.
Burmester et al., "Mononuclear phagocytes and rheumatoid synovitis. Mastermind or workhorse in arthritis?" Arthritis & Rheumatism, Jan. 1997, 40(1)5-18.
Campbell et al., "Collagen-induced arthritis in C57BL/6 (H-2$^b$) mice: new insights into an important disease model of rheumatoid arthritis," Eur. J. Immunol., 2000, 30:1568-1575.
Campbell et al., "Granulocyte-macrophage colony stimulating factor exacerbates collagen induced arthritis in mice," Ann. Rheum. Dis., 1997, 56:364-368.
Campbell et al., "Human articular cartilage and chondrocytes produce hemopoietic colony-stimulating factors in culture in response to IL-1$^1$," J. Immunology, Aug. 15, 1991, 147(4):1238-1246.
Campbell et al., "Production of macrophage colony-stimulating factor (M-CSF) by human articular cartilage and chondrocytes. Modulation by interleukin-1 and tumor necrosis factor α," Biochimica et Biophysica Acta, 1993, 1182:57-63.
Campbell et al., "Protection from collagen-induced arthritis in granulocyte-macrophage colony-stimulating factor-deficient mice," J. Immunol., 1998, 161:3639-3644.

(Continued)

*Primary Examiner* — Prema Mertz
(74) *Attorney, Agent, or Firm* — Foley & Lardner LLP

(57) ABSTRACT

The present invention provides recombinant antigen-binding regions, antibodies and functional fragments thereof that are specific for GM-CSF, which plays an integral role in various disorders or conditions. These antibodies, accordingly, can be used to treat, for example, inflammatory diseases such as rheumatoid arthritis. Antibodies of the invention also can be used in the diagnostics field, as well as for further investigating the role of GM-CSF in the progression of various disorders. The invention also provides nucleic acid sequences encoding the foregoing antibodies, vectors containing the same, pharmaceutical compositions and kits with instructions for use.

5 Claims, 21 Drawing Sheets

(56) References Cited

OTHER PUBLICATIONS

Campbell et al., "The colony-stimulating factors and collagen-induced arthritis: exacerbation of disease by M-CSF and G-CSF and requirement for endogenous M-CSF," Journal of Leukocyte Biology, Jul. 2000, 68:144-150.
Carrieri et al., "Profile of cerebrospinal fluid and serum cytokines in patients with relapsing-remitting multiple sclerosis: a correlation with clinical activity," Immunopharmacol. Immunotoxicol., 1998, 20(3):373-382.
Cebon et al., "Granulocyte-macrophage stimulating factor from human lymphocytes," J. Biol. Chem., Mar. 15, 1990, 265(8):4483-4491.
Chantry et al,. "Granulocyte-macrophage colony stimulating factor induces both HLA-DR expression and cytokine production by human monocytes," Cytokine, Jan. 1990, 2(1):60-67.
Chen et al., "Selection and analysis of an optimized anti-VEGF antibody: crystal structure of an affinity-matured Fab in complex with antigen," J. Mol. Biol. , 1999, 293:865-81.
Cheng et al., "Granulocyte-macrophage colony stimulating factor up-regulates CCR1 in human neutrophils," J. Immunol., 2001, 166:1178-1184.
Clark et al., "The human hematopoietic colony-stimulating factors," Science, Jun. 5, 1987, 236:1229-1237.
Cook et al., "Blockade of collagen-induced arthritis post-onset by antibody to granulocyte-macrophage colony-stimulating factor (GM-CSF): requirement for GM-CSF in the effector phase of disease," Arthritis Research, 2001, 3:293-298.
de Groot et al., "Regulation of proliferation, differentiation and survival by the IL-3/IL-5/GM-CSF receptor family," Cell. Signal, 1998, 10(9):619-628.
de Vries et al., "Flare-up of rheumatoid arthritis during GM-CSF treatment after chemotherapy," Lancet, Aug. 24, 1991, 338:517-518.
Diederichs et al., "Novel fold and putative receptor binding site of granulocyte-macrophage colony-stimulating factor," Science, Dec. 20, 1991, 254:1779-1782.
Drake et al., "Characterizing high-affinity antigen/antibody complexes by kinetic- and equilibrium-based methods," Anal. Biochem. 2004, 328:35-43.
Dranoff et al., "Involvement of granulocyte-macrophage colony-stimulating factor in pulmonary homeostasis," Science, Apr. 29, 1994, 264:713-716.
Finkelman et al., "Anti-Cytokine Antibodies as Carrier Proteins," J. Immunology, Aug. 1, 1993, 151(3):1235-1244.
Firestein et al., "Cytokines in Chronic Inflammatory Arthritis," J. Exp. Med., Nov. 1988, 168:1573-1586.
Friguet et al., "Measurements of the true affinity constant in solution of antigen-antibody complexes by enzyme-linked immunosorbent assay," J. Immunol. Methods, 1985, 77:305-19.
Gasson et al., "High-affinity binding of granulocyte-macrophage colony-stimulating factor to normal and leukemic human myeloid cells," Proc .Natl .Acad. Sci. U S A., Feb. 1986, 83:669-673.
Gasson et al., "Human granulocyte-macrophage colony-stimulating factor (GM-CSF): regulation of expression," Hematopoietic Growth Factors in Transfusion Medicine, 1990:27-41.
Gasson et al., "The biology of human granulocyte-macrophage colony-stimulating factor (GM-CSF)," The Biology of Hematopoieses, 1990:375-384.
Gearing et al., "Expression cloning of a receptor for human granulocyte-macrophage colony-stimulating factor," EMBO J., 1989, 8(12):3667-3676.
Gomez-Cambronero et al., "Granulocyte-macrophage colony-stimulating factor is a chemoattractant cytokine for human neutrophils: involvement of the ribosomal p70 S6 kinase signaling pathway," J. Immunol., 2003, 171:6846-6855.
Grossman, H.B., "Clinical Applications of Monoclonal Antibody Technology," Urologic Clinics of North America, Aug. 1986, 13(3):465-474.

Haenel et al., "Characterization of high-affinity antibodies by electrochemiluminescence-based equilibrium titration," Analytical Biochemistry, 2005, 339(1):182-184.
Hamilton et al., "Regulation of Macrophage Colony-Stimulating Factor (M-CSF) Production in Cultured Human Synovial Fibroblasts," Growth Factors, 1993, 9:157-165.
Hamilton,J.A., "GM-CSF in inflammation and autoimmunity," Trends Immunol., Aug. 2002, 23(8):403-408.
Hamilton,J.A., "Rheumatoid arthritis: opposing actions of hemopoietic growth factors and slow acting anti-rheumatic drugs," Lancet, Aug. 28, 1993, 342:536-539.
Hart et al., "Synergistic activation of human monocytes by granulocyte-macrophage colony-stimulating factor and IFN-gamma. Increased TNF-alpha but not IL-1 activity," J. Immunol., Sep. 1, 1998, 141(5):1516-1521.
Haworth et al., "Expression of granulocyte-macrophage colony-stimulating factor in rheumatoid arthritis: regulation by tumor necrosis factor-α," Eur. J. Immunol., 1991, 21:2575-2579.
Hayashida et al., "Molecular cloning of a second subunit of the receptor for human granulocyte-macrophage colony-stimulating factor (GM-CSF): reconstitution of a high-affinity GM-CSF receptor," Proc. Natl. Acad. Sci. U S A, Dec. 1990, 87:9655-9659.
Hazenberg et al., "Correction of granulocytopeani in Felty's Syndrome by granulocyte-macrophage colony-stimulating factor. Simultaneous induction of interleukin-6 release and flare-up of the arthritis," Blood, Dec. 1989, 74(8):2769-2770.
Hercus et al., "Specific human granulocyte-macrophage colony-stimulating factor antagonists," PNAS, Jun. 1994, 91:5838-5842.
Kastelein et al., "GM-CSF receptor: interactions and activation," Oncogene, 1993, 8:231-236.
Kaufman et al., "Effects of human GM-CSF on neutrophil degranulation in vitro," Exp. Hematol., 1989, 17:800-804.
Khaw et al., "Myocardial Infarct Imaging of Antibodies to Canine Cardiac Myosin with Indium-111-Diethylenetriamine Pentaacetic Acid," Science, Jul. 11, 1980, 208:295-297.
Khorana et al., "Studies on Polynucleotides: CIII. Total Synthesis of the Structural Gene for an Alanine Transfer Ribonucleic Acid from Yeast," J. Mol. Biol., 1972, 72:209-217.
Kinne et al., "Macrophages in rheumatoid arthritis," Arthritis Research, 2000, 2(3):189-202.
Kitamura et al., "Establishment and characterization of a unique human cell line that proliferates dependently on GM-CSF, IL-3, or erythropoietin," J. Cell. Physiol., 1989, 140:323-34.
Kitamura et al., "Expression cloning of the human IL-3 receptor cDNA reveals a shared beta subunit for the human IL-3 and GM-CSF receptors," Cell, Sep. 20, 1991, 66:1165-1174.
Kitamura et al., "Idiopathic pulmonary alveolar proteinosis as an autoimmune disease with neutralizing antibody against granulocyte/macrophage colony-stimulating factor," J .Exp. Med., Sep. 20, 1999, 190(6):875-880.
Knappik et al., "Fully synthetic human combinatorial antibody libraries (HuCAL) based on modular consensus frameworks and CDRs randomized with trinucleotides," J. Mol. Biol., 2000, 296:57-86.
Krebs et al., High-throughput generation and engineering of recombinant human antibodies, J. Immunol. Methods, 2001, 254:67-84.
Krinner et al., "A human monoclonal IgG1 potently neutralizing the pro-inflammatory cytokine GM-CSF," Molecular Immunology, Feb. 2007, 44(5):916-925.
Leizer et al., "Cytokine Regulation of Colony-Stimulating Factor Production in Cultured Human Synovial Fibroblasts: I. Induction of GM-CSF and G-CSF Production by Interleukin-1 and Tumor Necrosis Factor," Blood, Nov. 15, 1990, 76(10):1989-1996.
Lopez et al., "Recombinant human granulocyte-macrophage colony-stimulating factor stimulates in vitro mature human neutrophil and eosinophil function, surface receptor expression, and survival," J. Clin. Invest., Nov. 1986, 78:1220-1228.
McQualter et al., "Granulocyte macrophage colony-stimulating factor: a new putative therapeutic target in multiple sclerosis," J. Exp. Med., Oct. 1, 2001, 194(7):873-881.

(56) References Cited

OTHER PUBLICATIONS

Meager et al., "Spontaneously occurring neutralizing antibodies against granulocyte-macrophage colony-stimulating factor in patients with autoimmune disease," Immunology, 1999, 97:526-532.
Metcalf et al., "Biologic properties in vitro of a recombinant human granulocyte-macrophage colony-stimulating factor," Blood, Jan. 1986, 67(1):37-45.
Metcalf, Donald, "The Florey Lecture, 1991: The Colony-Stimulating Factors: Discovery to Clinical Use," Philosophical Transactions: Biological Sciences, Jul. 29, 1991, 333(1266):147-173.
Mulherin et al., "Synovial tissue macrophage populations and articular damage in rheumatoid arthritis.," Arthritis & Rheumatism, Jan. 1996, 39(1):115-124.
Nagy et al., "Fully human, HLA-DR-specific monoclonal antibodies efficiently induce programmed death of malignant lymphoid cells," Nature Medicine, Aug. 2002, 8(8):801-807.
Olver et al., "A phase I study of the GM-CSF antagonist E21R," Cancer Chemother. Pharmacol., 2002, 50:171-178.
Paine III et al., "Impaired functional activity of alveolar macrophages from GM-CSF-deficient mice," Am. J. Physiol. Lung Cell Mol. Physiol., 2001, 281:L1210-L1218.
Plenz et al., "Alterations in the vascular extracellular matrix of granulocyte-macrophage colony-stimulating factor (GM-CSF)-deficient mice," Faseb J., Aug. 2003, 17:1451-1457.
Rapoport et al., "Granulocyte-macrophage colony-stimulating factor (GM-CSF) and granulocyte colony-stimulating factor (G-CSF): receptor biology, signal transduction, and neutrophil activation," Blood Reviews, 1992, 6:43-57.
Rauchenberger et al., "Human combinatorial Fab Library yielding specific and functional antibodies against the human fibroblast growth factor receptor 3.," J. Biol. Chem., Oct. 3, 2003, 278(40):38194-38205.
Robertson et al., "Granulocyte-macrophage colony stimulating factor gene expression and function during tumor promotion," Carcinogenesis, 1994, 15(5):1017-1029.
Santiago-Schwarz et al., "Dendritic cells (DCs) in rheumatoid arthritis (RA): progenitor cells and soluble factors contained in RA synovial fluid yield a subset of myeloid DCs that preferentially activate Th1 inflammatory-type responses," J. Immunol., 2001, 167:1758-1768.
Sato et al., "Signal transduction by the high-affinity GM-CSF receptor: two distinct cytoplasmic regions of the common beta subunit responsible for different signaling," EMBO J., 1993, 12(11):4181-4189.
Schier et al., "Isolation of picomolar affinity anti-c-erbB-2 single-chain Fv by molecular evolution of the complementarity determining regions in the center of the antibody binding site,". J. Mol. Biol., 1996, 263:551-67.
Shanafelt et al., "Identification of critical amino acid residues in human and mouse granulocyte-macrophage colony-stimulating factor and their involvement in species specificity," J. Biol. Chem., Jul. 25, 1991, 266(21):13804-13810.
Shanafelt et al., "The amino-terminal helix of GM-CSF and IL-5 governs high affinity binding to their receptors," EMBO J., 1991, 10(13):4105-4112.

Shibata et al., "GM-CSF regulates alveolar macrophage differentiation and innate immunity in the lung through PU.1," Immunity, Oct. 2001, 15:557-567.
Sisson et al., "Production of interleukin-1 alpha, interleukin-1 beta and tumor necrosis factor by human mononuclear cells stimulated with granulocyte-macrophage colony-stimulating factor," Blood, Oct. 1988, 72(4):1368-1374.
Stanley et al., "Granulocyte/macrophage colony-stimulating factor-deficient mice show no major perturbation of hematopoiesis but develop a characteristic pulmonary pathology," Proc. Natl. Acad. Sci. U S A, Jun. 1994, 91:5592-5596.
Trapnell et al., "GM-CSF regulates pulmonary surfactant homeostasis and alveolar macrophage-mediated innate host defense," Annu. Rev. Physiol., 2002, 64:775-802.
Uchida et al., "High-affinity autoantibodies specifically eliminate granulocyte-macrophage colony-stimulating factor activity in the lungs of patients with idiopathic pulmonary alveolar proteinosis," Blood, Feb. 1, 2004, 103(3):1089-1098.
Unger et al., "Magnetic Resonance Imaging Using Gadolinium Labeled Monoclonal Antibody," Investigative Radiology, Oct. 1985, 20:693-700.
Vasunia et al., "Granulocyte-macrophage colony-stimulating factor (GM-CSF) is expressed in mouse skin in response to tumor-promoting agents and modulates dermal inflammation and epidermal dark cell numbers," Carcinogenesis, 1994, 15(4):653-660.
Virnekäs et al., "Trinucleotide phosphoramidites: ideal reagents for the synthesis of mixed oligonucleotides for random mutagenesis," Nucleic Acids Research, 1994, 22(25):5600-5607.
Williamson et al., "The detection and initial characterization of colony-stimulating factors in synovial fluid," Clin. Exp. Immunol., 1988, 72:67-73.
Xu et al., "Cytokines in chronic inflammatory arthritis. II. Granulocyte-macrophage colony-stimulating factor in rheumatoid synovial effusions," J. Clin. Invest., Mar. 1989, 83:876-882.
Yamashita et al., "Attenuation of airway hyperresponsiveness in a murine asthma model by neutralization of GM-CSF," Cellular Immunology, 2002, 219:92-97.
Yang et al., "CDR walking mutagenesis for the affinity maturation of a potent human anti-HIV-1 antibody into the picomolar range," J. Mol. Biol., 1995, 254:392-403.
Zhang et al., "Differential regulation of monocyte matrix metalloproteinase and TIMP-1 production by TNF-alpha, granulocyte-macrophage CSF, and IL-1 beta through prostaglandin-dependent and—independent mechanisms," J. Immunol., 1998, 161:3071-3076.
Brown et al., "Two neutralizing monoclonal antibodies against human granulocyte-macrophage conoly-stimulating factor recognize the receptor binding domain of the molecule," J. Immunology, Mar. 15, 1990, 144(6):2184-2189.
Eberhardt et al., "Identification of two potential receptor-binding sites for hGM-CSF," Brazilian Journal of Chemical Engineering, Jan./Mar. 2003, 20(1):6 pages.
Kanakura et al., "Identification of Functionally Distinct Domains of Human Granulocyte-Macrophage Colony-Stimulating Factor Using Monoclonal Antibodies," Blood, Mar. 1, 1991, 77(5):1033-1043.

* cited by examiner

FIG 1A

Variable Heavy Chain DNA

3684_ VH3 (SEQ ID NO: 1):

CAGGTGCAATTGGTGGAAAGCGGCGGCGGCCTGGTGCAACCGGGCGGCAGCCTGCGT
CTGAGCTGCGCGGCCTCCGGATTTACCTTTTCTTCTCATTGGATGTCTTGGGTGCGCCA
AGCCCCTGGGAAGGGTCTCGAGTGGGTGAGCAATGGTATCTTTTCTGATGGTAGCGCT
ACCTATTATGCGGATAGCGTGAAAGGCCGTTTTACCATTTCACGTGATAATTCGAAAAAC
ACCCTGTATCTGCAAATGAACAGCCTGCGTGCGGAAGATACGGCCGTGTATTATTGCGC
GCGTTTTCAGGGTTATGGTGGTGGTTTTGATTATTGGGGCCAAGGCACCCTGGTGACG
GTTAGCTCA

4251_VH3 (SEQ ID NO: 2):

CAGGTGCAATTGGTGGAAAGCGGCGGCGGCCTGGTGCAACCGGGCGGCAGCCTGCGT
CTGAGCTGCGCGGCCTCCGGATTTACCTTTTCTTCTCATTGGATGTCTTGGGTGCGCCA
AGCCCCTGGGAAGGGTCTCGAGTGGGTGAGCAATATTTGGCGTGGTCCTTATATTTATT
ATGCTGATTCTGTTAAGGGTCGTTTTACCATTTCACGTGATAATTCGAAAAACACCCTGT
ATCTGCAAATGAACAGCCTGCGTGCGGAAGATACGGCCGTGTATTATTGCGCGCGTTTT
CAGGGTTATGGTGGTGGTTTTGATTATTGGGGCCAAGGCACCCTGGTGACGGTTAGCT
CA

3929_ VH3 (SEQ ID NO: 3):

CAGGTGCAATTGGTGGAAAGCGGCGGCGGCCTGGTGCAACCGGGCGGCAGCCTGCGT
CTGAGCTGCGCGGCCTCCGGATTTACCTTTTCTTCTTATTGGATGAATTGGGTGCGCCA
AGCCCCTGGGAAGGGTCTCGAGTGGGTGAGCGGTATCTCTTATTCTGGTAGCGAGACC
TATTATGCGGATAGCGTGAAAGGCCGTTTTACCATTTCACGTGATAATTCGAAAAACACC
CTGTATCTGCAAATGAACAGCCTGCGTGCGGAAGATACGGCCGTGTATTATTGCGCGC
GTGGTTTTGGTACTGATTTTTGGGGCCAAGGCACCCTGGTGACGGTTAGCTCA

FIG 1A (continued)

4252_VH 3 (SEQ ID NO: 4):

CAGGTGCAATTGGTGGAAAGCGGCGGCGGCCTGGTGCAACCGGGCGGCAGCCTGCGT
CTGAGCTGCGCGGCCTCCGGATTTACCTTTTCTTCTTATTGGATGAATTGGGTGCGCCA
AGCCCCTGGGAAGGGTCTCGAGTGGGTGAGCGGTATTGAGAATAAGTATGCTGGTGGT
GCTACTTATTATGCTGCTTCTGTTAAGGGTCGTTTTACCATTTCACGTGATAATTCGAAAA
ACACCCTGTATCTGCAAATGAACAGCCTGCGTGCGGAAGATACGGCCGTGTATTATTGC
GCGCGTGGTTTTGGTACTGATTTTTGGGGCCAAGGCACCCTGGTGACGGTTAGCTCA

4287_ VH3 (SEQ ID NO: 5):

CAGGTGCAATTGGTGGAAAGCGGCGGCGGCCTGGTGCAACCGGGCGGCAGCCTGCGT
CTGAGCTGCGCGGCCTCCGGATTTACCTTTTCTTCTTATTGGATGAATTGGGTGCGCCA
AGCCCCTGGGAAGGGTCTCGAGTGGGTGAGCGGTATTGAGAATAAGCGTGCTGGTGGT
GCTACTTTTTATGCTGCTTCCGTTAAGGGTCGTTTTACCATTTCACGTGATAATTCGAAAA
ACACCCTGTATCTGCAAATGAACAGCCTGCGTGCGGAAGATACGGCCGTGTATTATTGC
GCGCGTGGTTTTGGTACTGATTTTTGGGGCCAAGGCACCCTGGTGACGGTTAGCTCA

4290_ VH3 (SEQ ID NO: 6):

CAGGTGCAATTGGTGGAAAGCGGCGGCGGCCTGGTGCAACCGGGCGGCAGCCTGCGT
CTGAGCTGCGCGGCCTCCGGATTTACCTTTTCTTCTTATTGGATGAATTGGGTGCGCCA
AGCCCCTGGGAAGGGTCTCGAGTGGGTGAGCGGTATTGAGTCTAAGTGGGCTGGTGGT
GCTACTTATTATGCTGCTGGTGTTAAGGGTCGTTTTACCATTTCACGTGATAATTCGAAA
AACACCCTGTATCTGCAAATGAACAGCCTGCGTGCGGAAGATACGGCCGTGTATTATTG
CGCGCGTGGTTTTGGTACTGATTTTTGGGGCCAAGGCACCCTGGTGACGGTTAGCTCA

4302_VH3 (SEQ ID NO: 7):

CAGGTGCAATTGGTGGAAAGCGGCGGCGGCCTGGTGCAACCGGGCGGCAGCCTGCGT
CTGAGCTGCGCGGCCTCCGGATTTACCTTTTCTTCTTATTGGATGAATTGGGTGCGCCA
AGCCCCTGGGAAGGGTCTCGAGTGGGTGAGCGGTATCTCTTATTCTGGTAGCGAGACC
TATTATGCGGATAGCGTGAAAGGCCGTTTTACCATTTCACGTGATAATTCGAAAAACACC
CTGTATCTGCAAATGAACAGCCTGCGTGCGGAAGATACGGCCGTGTATTATTGCGCGC
GTGGTTTTGGTACTGATTTTTGGGGCCAAGGCACCCTGGTGACGGTTAGCTCA

FIG 1A (continued)

4350_ VH3 (SEQ ID NO: 8):

CAGGTGCAATTGGTGGAAAGCGGCGGCGGCCTGGTGCAACCGGGCGGCAGCCTGCGT
CTGAGCTGCGCGGCCTCCGGATTTACCTTTTCTTCTTATTGGATGAATTGGGTGCGCCA
AGCCCCTGGGAAGGGTCTCGAGTGGGTGAGCGGTATTGAGAATAAGCGTGCTGGTGGT
GCTACTTTTTATGCTGCTTCCGTTAAGGGTCGTTTTACCATTTCACGTGATAATTCGAAAA
ACACCCTGTATCTGCAAATGAACAGCCTGCGTGCGGAAGATACGGCCGTGTATTATTGC
GCGCGTGGTTTTGGTACTGATTTTTGGGGCCAAGGCACCCTGGTGACGGTTAGCTCA

4354_ VH3 (SEQ ID NO: 9):

CAGGTGCAATTGGTGGAAAGCGGCGGCGGCCTGGTGCAACCGGGCGGCAGCCTGCGT
CTGAGCTGCGCGGCCTCCGGATTTACCTTTTCTTCTTATTGGATGAATTGGGTGCGCCA
AGCCCCTGGGAAGGGTCTCGAGTGGGTGAGCGGTATTGAGTCTAAGTGGGCTGGTGGT
GCTACTTATTATGCTGCTGGTGTTAAGGGTCGTTTTACCATTTCACGTGATAATTCGAAA
AACACCCTGTATCTGCAAATGAACAGCCTGCGTGCGGAAGATACGGCCGTGTATTATTG
CGCGCGTGGTTTTGGTACTGATTTTTGGGGCCAAGGCACCCTGGTGACGGTTAGCTCA

4357_ VH3 (SEQ ID NO: 10):

CAGGTGCAATTGGTGGAAAGCGGCGGCGGCCTGGTGCAACCGGGCGGCAGCCTGCGT
CTGAGCTGCGCGGCCTCCGGATTTACCTTTTCTTCTTATTGGATGAATTGGGTGCGCCA
AGCCCCTGGGAAGGGTCTCGAGTGGGTGAGCGGTATTGAGAATAAGTATGCTGGTGGT
GCTACTTATTATGCTGCTTCTGTTAAGGGTCGTTTTACCATTTCACGTGATAATTCGAAAA
ACACCCTGTATCTGCAAATGAACAGCCTGCGTGCGGAAGATACGGCCGTGTATTATTGC
GCGCGTGGTTTTGGTACTGATTTTTGGGGCCAAGGCACCCTGGTGACGGTTAGCTCA

FIG 1A (continued)

3682_VH1A (SEQ ID NO: 44)

CAGGTGCAATTGGTTCAGTCTGGCGCGGAAGTGAAAAAACCGGGCAGCAGCGT
GAAAGTGAGCTGCAAAGCCTCCGGAGGCACTTTTAATTCTTTTCTTATTTCTTGG
GTGCGCCAAGCCCCTGGGCAGGGTCTCGAGTGGATGGGCGGTATCATTCCGAT
TTTTGGCACTGCGAATTACGCGCAGAAGTTTCAGGGCCGGGTGACCATTACCGC
GGATGAAAGCACCAGCACCGCGTATATGGAACTGAGCAGCCTGCGTAGCGAAG
ATACGGCCGTGTATTATTGCGCGCGTAAGTTTATTTCTGATTCTTGGGGCCAAG
GCACCCTGGTGACGGTTAGCTCA

4283_VH1A (SEQ ID NO: 45)

CAGGTGCAATTGGTTCAGTCTGGCGCGGAAGTGAAAAAACCGGGCAGCAGCGT
GAAAGTGAGCTGCAAAGCCTCCGGAGGCACTTTTAATTCTTTTCTTATTTCTTGG
GTGCGCCAAGCCCCTGGGCAGGGTCTCGAGTGGATGGGCGCTATTTCTCCTTG
GGATGGTGTTACTGGTTATGCTCAGAAGTTTCAGGGTCGGGTGACCATTACCGC
GGATGAAAGCACCAGCACCGCGTATATGGAACTGAGCAGCCTGCGTAGCGAAG
ATACGGCCGTGTATTATTGCGCGCGTAAGTTTATTTCTGATTCTTGGGGCCAAG
GCACCCTGGTGACGGTTAGCTCA

4297_VH1A (SEQ ID NO: 46)

CAGGTGCAATTGGTTCAGTCTGGCGCGGAAGTGAAAAAACCGGGCAGCAGCGT
GAAAGTGAGCTGCAAAGCCTCCGGAGGCACTTTTAATTCTTTTCTTATTTCTTGG
GTGCGCCAAGCCCCTGGGCAGGGTCTCGAGTGGATGGGCGGTATCATTCCGAT
TTTTGGCACTGCGAATTACGCGCAGAAGTTTCAGGGCCGGGTGACCATTACCGC
GGATGAAAGCACCAGCACCGCGTATATGGAACTGAGCAGCCTGCGTAGCGAAG
ATACGGCCGTGTATTATTGCGCGCGTAAGTTTATTTCTGATTCTTGGGGCCAAG
GCACCCTGGTGACGGTTAGCTCA

FIG 1A (continued)

4342_VH1A (SEQ ID NO: 47)

CAGGTGCAATTGGTTCAGTCTGGCGCGGAAGTGAAAAAACCGGGCAGCAGCGT
GAAAGTGAGCTGCAAAGCCTCCGGAGGCACTTTTAATTCTTTTCTTATTTCTTGG
GTGCGCCAAGCCCCTGGGCAGGGTCTCGAGTGGATGGGCGCTATTTCTCCTTG
GGATGGTGTTACTGGTTATGCTCAGAAGTTTCAGGGTCGGGTGACCATTACCGC
GGATGAAAGCACCAGCACCGCGTATATGGAACTGAGCAGCCTGCGTAGCGAAG
ATACGGCCGTGTATTATTGCGCGCGTAAGTTTATTTCTGATTCTTGGGGCCAAG
GCACCCTGGTGACGGTTAGCTCA

4357_VH codon-optimized (SEQ ID NO: 48)

CAGGTGCAGCTGGTCGAGTCTGGCGGCGGACTGGTGCAGCCTGGCGGCAGCC
TGAGACTGAGCTGTGCCGCCAGCGGCTTCACCTTCAGCAGCTACTGGATGAAC
TGGGTGAGGCAGGCCCCTGGCAAGGGCCTGGAGTGGGTGTCCGGCATCGAGA
ACAAGTATGCCGGCGGAGCCACCTACTACGCCGCCAGCGTGAAGGGCCGGTTC
ACCATCAGCCGGGACAACAGCAAGAACACCCTGTACCTGCAGATGAACAGCCT
GAGGGCCGAGGACACCGCCGTGTACTACTGTGCCAGGGGCTTCGGCACCGATT
TCTGGGGCCAGGGCACCCTGGTGACAGTCAGCTCA

FIG 1B

Variable Heavy Chain Peptide

(CDR Regions in Bold)

3684_ VH3 (SEQ ID NO: 11):

QVQLVESGGGLVQPGGSLRLSCAASGFTFSSHWMSWVRQAPGKGLEWVSNGIFSDGSAT YYADSVKGRFTISRDNSKNTLYLQMNSLRAEDTAVYYCARFQGYGGGFDYWGQGTLVTVS S

4251_VH3 (SEQ ID NO: 12):

QVQLVESGGGLVQPGGSLRLSCAASGFTFSSHWMSWVRQAPGKGLEWVSNIWRGPYIYY ADSVKGRFTISRDNSKNTLYLQMNSLRAEDTAVYYCARFQGYGGGFDYWGQGTLVTVSS

3929_ VH3 (SEQ ID NO: 13):

QVQLVESGGGLVQPGGSLRLSCAASGFTFSSYWMNWVRQAPGKGLEWVSGISYSGSETY YADSVKGRFTISRDNSKNTLYLQMNSLRAEDTAVYYCARGFGTDFWGQGTLVTVSS

4252_VH 3 (SEQ ID NO: 14):

QVQLVESGGGLVQPGGSLRLSCAASGFTFSSYWMNWVRQAPGKGLEWVSGIENKYAGG ATYYAASVKGRFTISRDNSKNTLYLQMNSLRAEDTAVYYCARGFGTDFWGQGTLVTVSS

4287_VH 3 (SEQ ID NO: 15):

QVQLVESGGGLVQPGGSLRLSCAASGFTFSSYWMNWVRQAPGKGLEWVSGIENKRAGG ATFYAASVKGRFTISRDNSKNTLYLQMNSLRAEDTAVYYCARGFGTDFWGQGTLVTVSS

4290_VH 3 (SEQ ID NO: 16):

QVQLVESGGGLVQPGGSLRLSCAASGFTFSSYWMNWVRQAPGKGLEWVSGIESKWAGG ATYYAAGVKGRFTISRDNSKNTLYLQMNSLRAEDTAVYYCARGFGTDFWGQGTLVTVSS

FIG 1B (continued)

4302_VH 3 (SEQ ID NO: 17):

QVQLVESGGGLVQPGGSLRLSCAASGFTFSSYWMNWVRQAPGKGLEWVSGISYSGSETY YADSVKGRFTISRDNSKNTLYLQMNSLRAEDTAVYYCARGFGTDFWGQGTLVTVSS

4350_VH 3 (SEQ ID NO: 18):
QVQLVESGGGLVQPGGSLRLSCAASGFTFSSYWMNWVRQAPGKGLEWVSGIENKRAGG ATFYAASVKGRFTISRDNSKNTLYLQMNSLRAEDTAVYYCARGFGTDFWGQGTLVTVSS

4354_VH 3 (SEQ ID NO: 19):

QVQLVESGGGLVQPGGSLRLSCAASGFTFSSYWMNWVRQAPGKGLEWVSGIESKWAGG ATYYAAGVKGRFTISRDNSKNTLYLQMNSLRAEDTAVYYCARGFGTDFWGQGTLVTVSS

4357_VH 3 (SEQ ID NO: 20):

QVQLVESGGGLVQPGGSLRLSCAASGFTFSSYWMNWVRQAPGKGLEWVSGIENKYAGG ATYYAASVKGRFTISRDNSKNTLYLQMNSLRAEDTAVYYCARGFGTDFWGQGTLVTVSS

3682_VH1A (SEQ ID NO: 49)

QVQLVQSGAEVKKPGSSVKVSCKASGGTFNSFLISWVRQAPGQGLEWMGGIIPIFG TANYAQKFQGRVTITADESTSTAYMELSSLRSEDTAVYYCARKFISDSWGQGTLVT VSS

4283_VH1A (SEQ ID NO: 50)

QVQLVQSGAEVKKPGSSVKVSCKASGGTFNSFLISWVRQAPGQGLEWMGAISPW DGVTGYAQKFQGRVTITADESTSTAYMELSSLRSEDTAVYYCARKFISDSWGQGTL VTVSS

FIG 1B (continued)

4297_VH1A (SEQ ID NO: 51)

QVQLVQSGAEVKKPGSSVKVSCKASGGTFNSFLISWVRQAPGQGLEWMGGIIPIFG TANYAQKFQGRVTITADESTSTAYMELSSLRSEDTAVYYCARKFISDSWGQGTLVT VSS

4342_VH1A (SEQ ID NO: 52)

QVQLVQSGAEVKKPGSSVKVSCKASGGTFNSFLISWVRQAPGQGLEWMGAISPW DGVTGYAQKFQGRVTITADESTSTAYMELSSLRSEDTAVYYCARKFISDSWGQGTL VTVSS

FIG 2A

Variable Light Chain DNA

3684_ VL lambda 3 (SEQ ID NO: 21):

GATATCGAACTGACCCAGCCGCCTTCAGTGAGCGTTGCACCAGGTCAGACCGCGCGTA
TCTCGTGTAGCGGCGATAATCTTCCTGGTAAGTATGTTCATTGGTACCAGCAGAAACCC
GGGCAGGCGCCAGTTCTTGTGATTTATTATGATTCTAATCGTCCCTCAGGCATCCCGGA
ACGCTTTAGCGGATCCAACAGCGGCAACACCGCGACCCTGACCATTAGCGGCACTCAG
GCGGAAGACGAAGCGGATTATTATTGCCAGTCTCGTACTCAGACTACTATTGTGTTTGG
CGGCGGCACGAAGTTAACCGTTCTTGGCCAG

4251_ VL lambda 3 (SEQ ID NO: 22):

GATATCGAACTGACCCAGCCGCCTTCAGTGAGCGTTGCACCAGGTCAGACCGCGCGTA
TCTCGTGTAGCGGCGATAATCTTCCTGGTAAGTATGTTCATTGGTACCAGCAGAAACCC
GGGCAGGCGCCAGTTCTTGTGATTTATTATGATTCTAATCGTCCCTCAGGCATCCCGGA
ACGCTTTAGCGGATCCAACAGCGGCAACACCGCGACCCTGACCATTAGCGGCACTCAG
GCGGAAGACGAAGCGGATTATTATTGCCAGTCTCGTACTCAGACTACTATTGTGTTTGG
CGGCGGCACGAAGTTAACCGTTCTTGGCCAG

3929_VL lambda 3 (SEQ ID NO: 23):

GATATCGAACTGACCCAGCCGCCTTCAGTGAGCGTTGCACCAGGTCAGACCGCGCGTA
TCTCGTGTAGCGGCGATTCTATTGGTAAGAAGTATGCTTATTGGTACCAGCAGAAACCC
GGGCAGGCGCCAGTTCTTGTGATTTATAAGAAGCGTCCCTCAGGCATCCCGGAACGCT
TTAGCGGATCCAACAGCGGCAACACCGCGACCCTGACCATTAGCGGCACTCAGGCGGA
AGACGAAGCGGATTATTATTGCTCTTCTTGGGATTCTACTGGTCTTGTGTTTGGCGGCG
GCACGAAGTTAACCGTTCTTGGCCAG

4252_VL lambda 3 (SEQ ID NO: 24):

GATATCGAACTGACCCAGCCGCCTTCAGTGAGCGTTGCACCAGGTCAGACCGCGCGTA
TCTCGTGTAGCGGCGATTCTATTGGTAAGAAGTATGCTTATTGGTACCAGCAGAAACCC
GGGCAGGCGCCAGTTCTTGTGATTTATAAGAAGCGTCCCTCAGGCATCCCGGAACGCT
TTAGCGGATCCAACAGCGGCAACACCGCGACCCTGACCATTAGCGGCACTCAGGCGGA
AGACGAAGCGGATTATTATTGCTCTTCTTGGGATTCTACTGGTCTTGTGTTTGGCGGCG
GCACGAAGTTAACCGTTCTTGGCCAG

FIG 2A (continued)

4287_VL lambda 3 (SEQ ID NO: 25):

GATATCGAACTGACCCAGCCGCCTTCAGTGAGCGTTGCACCAGGTCAGACCGCGCGTA
TCTCGTGTAGCGGCGATTCTATTGGTAAGAAGTATGCTTATTGGTACCAGCAGAAACCC
GGGCAGGCGCCAGTTCTTGTGATTTATAAGAAGCGTCCCTCAGGCATCCCGGAACGCT
TTAGCGGATCCAACAGCGGCAACACCGCGACCCTGACCATTAGCGGCACTCAGGCGGA
AGACGAAGCGGATTATTATTGCTCTTCTTGGGATTCTACTGGTCTTGTGTTTGGCGGCG
GCACGAAGTTAACCGTTCTTGGCCAG

4290_VL lambda 3 (SEQ ID NO: 26):

GATATCGAACTGACCCAGCCGCCTTCAGTGAGCGTTGCACCAGGTCAGACCGCGCGTA
TCTCGTGTAGCGGCGATTCTATTGGTAAGAAGTATGCTTATTGGTACCAGCAGAAACCC
GGGCAGGCGCCAGTTCTTGTGATTTATAAGAAGCGTCCCTCAGGCATCCCGGAACGCT
TTAGCGGATCCAACAGCGGCAACACCGCGACCCTGACCATTAGCGGCACTCAGGCGGA
AGACGAAGCGGATTATTATTGCTCTTCTTGGGATTCTACTGGTCTTGTGTTTGGCGGCG
GCACGAAGTTAACCGTTCTTGGCCAG

4302_VL lambda 3 (SEQ ID NO: 27):

GATATCGAACTGACCCAGCCGCCTTCAGTGAGCGTTGCACCAGGTCAGACCGCGCGTA
TCTCGTGTAGCGGCGATTCTATTGGTAAGAAGTATGCTTATTGGTACCAGCAGAAACCC
GGGCAGGCGCCAGTTCTTGTGATTTATAAGAAGCGTCCCTCAGGCATCCCGGAACGCT
TTAGCGGATCCAACAGCGGCAACACCGCGACCCTGACCATTAGCGGCACTCAGGCGGA
AGACGAAGCGGATTATTATTGCTCTGCTTGGGGTGATAAGGGTATGGTGTTTGGCGGCG
GCACGAAGTTAACCGTTCTTGGCCAG

4350_VL lambda 3 (SEQ ID NO: 28):

GATATCGAACTGACCCAGCCGCCTTCAGTGAGCGTTGCACCAGGTCAGACCGCGCGTA
TCTCGTGTAGCGGCGATTCTATTGGTAAGAAGTATGCTTATTGGTACCAGCAGAAACCC
GGGCAGGCGCCAGTTCTTGTGATTTATAAGAAGCGTCCCTCAGGCATCCCGGAACGCT
TTAGCGGATCCAACAGCGGCAACACCGCGACCCTGACCATTAGCGGCACTCAGGCGGA
AGACGAAGCGGATTATTATTGCTCTGCTTGGGGTGATAAGGGTATGGTGTTTGGCGGCG
GCACGAAGTTAACCGTTCTTGGCCAG

FIG 2A (continued)

4354_VL lambda 3 (SEQ ID NO: 29):

GATATCGAACTGACCCAGCCGCCTTCAGTGAGCGTTGCACCAGGTCAGACCGCGCGTA
TCTCGTGTAGCGGCGATTCTATTGGTAAGAAGTATGCTTATTGGTACCAGCAGAAACCC
GGGCAGGCGCCAGTTCTTGTGATTTATAAGAAGCGTCCCTCAGGCATCCCGGAACGCT
TTAGCGGATCCAACAGCGGCAACACCGCGACCCTGACCATTAGCGGCACTCAGGCGGA
AGACGAAGCGGATTATTATTGCTCTGCTTGGGGTGATAAGGGTATGGTGTTTGGCGGCG
GCACGAAGTTAACCGTTCTTGGCCAG

4357_VL lambda 3 (SEQ ID NO: 30):

GATATCGAACTGACCCAGCCGCCTTCAGTGAGCGTTGCACCAGGTCAGACCGCGCGTA
TCTCGTGTAGCGGCGATTCTATTGGTAAGAAGTATGCTTATTGGTACCAGCAGAAACCC
GGGCAGGCGCCAGTTCTTGTGATTTATAAGAAGCGTCCCTCAGGCATCCCGGAACGCT
TTAGCGGATCCAACAGCGGCAACACCGCGACCCTGACCATTAGCGGCACTCAGGCGGA
AGACGAAGCGGATTATTATTGCTCTGCTTGGGGTGATAAGGGTATGGTGTTTGGCGGCG
GCACGAAGTTAACCGTTCTTGGCCAG

3682_VL kappa 1 (SEQ ID NO: 53)

GATATCCAGATGACCCAGAGCCCGTCTAGCCTGAGCGCGAGCGTGGGTGATCG
TGTGACCATTACCTGCAGAGCGAGCCAGACTATTAATAATTATCTGAATTGGTAC
CAGCAGAAACCAGGTAAAGCACCGAAACTATTAATTTATACTGCTTCTAATTTGC
AAAGCGGGGTCCCGTCCCGTTTTAGCGGCTCTGGATCCGGCACTGATTTTACCC
TGACCATTAGCAGCCTGCAACCTGAAGACTTTGCGGTTTATTATTGCCAGCAGTA
TTCTGGTTCTCCTATGACCTTTGGCCAGGGTACGAAAGTTGAAATTAAACGTACG

FIG 2A (continued)

4283_VL kappa 1 (SEQ ID NO: 54)

GATATCCAGATGACCCAGAGCCCGTCTAGCCTGAGCGCGAGCGTGGGTGATCG
TGTGACCATTACCTGCAGAGCGAGCCAGACTATTAATAATTATCTGAATTGGTAC
CAGCAGAAACCAGGTAAAGCACCGAAACTATTAATTTATACTGCTTCTAATTTGC
AAAGCGGGGTCCCGTCCCGTTTTAGCGGCTCTGGATCCGGCACTGATTTTACCC
TGACCATTAGCAGCCTGCAACCTGAAGACTTTGCGGTTTATTATTGCCAGCAGTA
TTCTGGTTCTCCTATGACCTTTGGCCAGGGTACGAAAGTTGAAATTAAACGTACG

4297_VL kappa 1 (SEQ ID NO: 55)

GATATCCAGATGACCCAGAGCCCGTCTAGCCTGAGCGCGAGCGTGGGTGATCG
TGTGACCATTACCTGCAGAGCGAGCCAGACTATTAATAATTATCTGAATTGGTAC
CAGCAGAAACCAGGTAAAGCACCGAAACTATTAATTTATACTGCTTCTAATTTGC
AAAGCGGGGTCCCGTCCCGTTTTAGCGGCTCTGGATCCGGCACTGATTTTACCC
TGACCATTAGCAGCCTGCAACCTGAAGACTTTGCGACCTATTATTGCCAGCAGT
ATTCTTGGGTTCCTCATACCTTTGGCCAGGGTACGAAAGTTGAAATTAAACGTAC
G

4342_VL kappa 1 (SEQ ID NO: 56)

GATATCCAGATGACCCAGAGCCCGTCTAGCCTGAGCGCGAGCGTGGGTGATCG
TGTGACCATTACCTGCAGAGCGAGCCAGACTATTAATAATTATCTGAATTGGTAC
CAGCAGAAACCAGGTAAAGCACCGAAACTATTAATTTATACTGCTTCTAATTTGC
AAAGCGGGGTCCCGTCCCGTTTTAGCGGCTCTGGATCCGGCACTGATTTTACCC
TGACCATTAGCAGCCTGCAACCTGAAGACTTTGCGACCTATTATTGCCAGCAGT
ATTCTTGGGTTCCTCATACCTTTGGCCAGGGTACGAAAGTTGAAATTAAACGTAC
G

FIG 2A (continued)

4357_VL codon-optimized (SEQ ID NO: 57)

GACATCGAGCTGACCCAGCCCCCCAGCGTGTCTGTGGCCCCTGGCCAGACCG
CCCGGATCAGCTGCTCCGGCGACAGCATCGGCAAGAAGTACGCCTACTGGTAT
CAGCAGAAGCCCGGCCAGGCCCCCGTGCTGGTGATCTACAAGAAGCGGCCCA
GCGGCATCCCCGAGCGGTTCAGCGGCAGCAACAGCGGCAACACCGCCACCCT
GACCATCAGCGGCACCCAGGCCGAGGACGAGGCCGACTACTACTGCTCCGCCT
GGGGCGACAAGGGCATGGTGTTTGGCGGCGGAACAAAGTTAACCGTGCTGGG
GCAG

FIG 2B

Variable Light Chain Peptide (CDR Regions in Bold)

3684_ VL lambda 3 (SEQ ID NO: 31):

DIELTQPPSVSVAPGQTARISCSGDNLPGKYVHWYQQKPGQAPVLVIYYDSNRPSGIPERFSGSNSGNTATLTISGTQAEDEADYYCQSRTQTTIVFGGGTKLTVLGQ

4251_ VL lambda 3 (SEQ ID NO: 32):

DIELTQPPSVSVAPGQTARISCSGDNLPGKYVHWYQQKPGQAPVLVIYYDSNRPSGIPERFSGSNSGNTATLTISGTQAEDEADYYCQSRTQTTIVFGGGTKLTVLGQ

3929_VL lambda 3 (SEQ ID NO: 33):

DIELTQPPSVSVAPGQTARISCSGDSIGKKYAYWYQQKPGQAPVLVIYKKRPSGIPERFSGSNSGNTATLTISGTQAEDEADYYCSSWDSTGLVFGGGTKLTVLGQ

4252_VL lambda 3 (SEQ ID NO: 34):

DIELTQPPSVSVAPGQTARISCSGDSIGKKYAYWYQQKPGQAPVLVIYKKRPSGIPERFSGSNSGNTATLTISGTQAEDEADYYCSSWDSTGLVFGGGTKLTVLGQ

4287_VL lambda 3 (SEQ ID NO: 35):

DIELTQPPSVSVAPGQTARISCSGDSIGKKYAYWYQQKPGQAPVLVIYKKRPSGIPERFSGSNSGNTATLTISGTQAEDEADYYCSSWDSTGLVFGGGTKLTVLGQ

4290_VL lambda 3 (SEQ ID NO: 36):

DIELTQPPSVSVAPGQTARISCSGDSIGKKYAYWYQQKPGQAPVLVIYKKRPSGIPERFSGSNSGNTATLTISGTQAEDEADYYCSSWDSTGLVFGGGTKLTVLGQ

FIG 2B (continued)

4302_VL lambda 3 (SEQ ID NO: 37):

DIELTQPPSVSVAPGQTARISCSGDSIGKKYAYWYQQKPGQAPVLVIYKKRPSGIPERFSGS
NSGNTATLTISGTQAEDEADYYCSAWGDKGMVFGGGTKLTVLGQ

4350_VL lambda 3 (SEQ ID NO: 38):

DIELTQPPSVSVAPGQTARISCSGDSIGKKYAYWYQQKPGQAPVLVIYKKRPSGIPERFSGS
NSGNTATLTISGTQAEDEADYYCSAWGDKGMVFGGGTKLTVLGQ

4354_VL lambda 3 (SEQ ID NO: 39):

DIELTQPPSVSVAPGQTARISCSGDSIGKKYAYWYQQKPGQAPVLVIYKKRPSGIPERFSGS
NSGNTATLTISGTQAEDEADYYCSAWGDKGMVFGGGTKLTVLGQ

4357_VL lambda 3 (SEQ ID NO: 40):

DIELTQPPSVSVAPGQTARISCSGDSIGKKYAYWYQQKPGQAPVLVIYKKRPSGIPERFSGS
NSGNTATLTISGTQAEDEADYYCSAWGDKGMVFGGGTKLTVLGQ

3682_VL kappa 1 (SEQ ID NO: 58)

DIQMTQSPSSLSASVGDRVTITCRASQTINNYLNWYQQKPGKAPKLLIYTASNLQSGVPSRF
SGSGSGTDFTLTISSLQPEDFAVYYCQQYSGSPMTFGQGTKVEIKRT

4283_VL kappa 1 (SEQ ID NO: 59)

DIQMTQSPSSLSASVGDRVTITCRASQTINNYLNWYQQKPGKAPKLLIYTASNLQSGVPSRF
SGSGSGTDFTLTISSLQPEDFAVYYCQQYSGSPMTFGQGTKVEIKRT

4297_VL kappa 1 (SEQ ID NO: 60)

DIQMTQSPSSLSASVGDRVTITCRASQTINNYLNWYQQKPGKAPKLLIYTASNLQSGVPSRF
SGSGSGTDFTLTISSLQPEDFATYYCQQYSWVPHTFGQGTKVEIKRT

FIG 2B (continued)

4342 VL_kappa 1 (SEQ ID NO: 61)

DIQMTQSPSSLSASVGDRVTITCRASQTINNYLNWYQQKPGKAPKLLIYTASNLQSG
VPSRFSGSGSGTDFTLTISSLQPEDFATYYCQQYSWVPHTFGQGTKVEIKRT

FIG 3

Variable Heavy Chain Consensus Sequence (CDR Regions in Bold)

VH3 Consensus (SEQ ID NO: 41):

QVQLVESGGG LVQPGGSLRL SCAASGFTFS SYAMSWVRQA PGKGLEWVSA ISGSGGSTYY ADSVKGRFTI SRDNSKNTLY LQMNSLRAED TAVYYCARWG GDGFYAMDYW GQGTLVTVS S

FIG 4

Variable Light Chain Consensus Sequence (CDR Regions in Bold)

VL_λ3 Consensus (SEQ ID NO: 42):

DIELTQPPSV SVAPGQTARI SCSGDALGDK YASWYQQKPG QAPVLVIYDD SDRPSGIPER FSGSNSGNTA TLTISGTQAE DEADYYCQQH YTTPPVFGGG TKLTVLGQ

FIG 5

Example of DNA sequence of Fab expression vector pMORPH®X9_MOR03929_FH
SEQ ID NO: 43 atgaaaaagacagctatcgcgattgcagtggcactggctggtttcgctaccgtagcgcaggccgatatcgaactgacc
cagccgccttcagtgagcgttgcaccaggtcagaccgcgcgtatctcgtgtagcggcgattctattggtaagaagtatg
cttattggtaccagcagaaacccgggcaggcgccagttcttgtgatttataagaagcgtccctcaggcatcccggaac
gctttagcggatccaacagcggcaacaccgcgaccctgaccattagcggcactcaggcggaagacgaagcggatt
attattgctcttcttgggattctactggtcttgtgtttggcggcggcacgaagttaaccgttcttggccagccgaaagccgca
ccgagtgtgacgctgtttccgccgagcagcgaagaattgcaggcgaacaaagcgaccctggtgtgcctgattagcga
cttttatccgggagccgtgacagtggcctggaaggcagatagcagccccgtcaaggcgggagtggagaccaccac
accctccaaacaaagcaacaacaagtacgcggccagcagctatctgagcctgacgcctgagcagtggaagtccca
cagaagctacagctgccaggtcacgcatgaggggagcaccgtggaaaaaaccgttgcgccgactgaggcctgata
agcatgcgtaggagaaaataaaatgaaacaaagcactattgcactggcactcttaccgttgctcttcacccctgttacc
aaagcccaggtgcaattggtggaaagcggcggcggcctggtgcaaccgggcggcagcctgcgtctgagctgcgcg
gcctccggatttacctttcttcttattggatgaattgggtgcgccaagcccctgggaagggtctcgagtgggtgagcggt
atctcttattctggtagcgagacctattatgcggatagcgtgaaaggccgttttaccatttcacgtgataattcgaaaaaca
ccctgtatctgcaaatgaacagcctgcgtgcggaagatacggccgtgtattattgcgcgcgtggttttggtactgatttttg
gggccaaggcaccctggtgacggttagctcagcgtcgaccaaaggtccaagcgtgtttccgctggctccgagcagc
aaaagcaccagcggcggcacggctgccctgggctgcctggttaaagattatttcccggaaccagtcaccgtgagctg
gaacagcggggcgctgaccagcggcgtgcatacctttccggcggtgctgcaaagcagcggcctgtatagcctgagc
agcgttgtgaccgtgccgagcagcagcttaggcactcagacctatatttgcaacgtgaaccataaaccgagcaacac
caaagtggataaaaaagtggaaccgaaaagcgaattcgactataaagatgacgatgacaaaggcgcgccgcacc
atcatcaccatcactgataagcttgacctgtgaagtgaaaaatggcgcagattgtgcgacattttttgtctgccgtttaatt
aaaggggggggggggccggcctgggggggggtgtacatgaaattgtaaacgttaatattttgttaaaattcgcgttaa
atttttgttaaatcagctcatttttaaccataggccgaaatcggcaaaatcccttataaatcaaaagaatagaccgaga
tagggttgagtgttgttccagtttggaacaagagtccactattaaagaacgtggactccaacgtcaaagggcgaaaaa
ccgtctatcagggcgatggcccactacgagaaccatcaccctaatcaagttttttggggtcgaggtgccgtaaagcact
aaatcggaaccctaaagggagcccccgatttagagcttgacggggaaagccggcgaacgtggcgagaaaggaa
gggaagaaagcgaaaggagcgggcgctagggcgctggcaagtgtagcggtcacgctgcgcgtaaccaccacac
ccgccgcgcttaatgcgccgctacagggcgcgtgctagactagtgtttaaaccggaccggggggggggcttaagtggg
ctgcaaaacaaaacggcctcctgtcaggaagccgcttttatcgggtagcctcactgcccgctttccagtcgggaaacct
gtcgtgccagctgcatcagtgaatcggccaacgcgcggggagaggcggtttgcgtattgggagccagggtggttttct
tttcaccagtgagacgggcaacagctgattgcccttcaccgcctggccctgagagagttgcagcaagcggtccacgct
ggtttgccccagcaggcgaaaatcctgtttgatggtggtcagcggcgggatataacatgagctgtcctcggtatcgtcgt
atcccactaccgagatgtccgcaccaacgcgcagcccggactcggtaatggcacgcattgcgcccagcgccatctg
atcgttggcaaccagcatcgcagtgggaacgatgccctcattcagcatttgcatggtttgttgaaaaccggacatggca
ctccagtcgccttcccgttccgctatcggctgaatttgattgcgagtgagatatttatgccagccagccagacgcagacg
cgccgagacagaacttaatgggccagctaacagcgcgatttgctggtggcccaatgcgaccagatgctccacgccc
agtcgcgtaccgtcctcatgggagaaaataatactgttgatgggtgtctggtcagagacatcaagaaataacgccgga
acattagtgcaggcagcttccacagcaatagcatcctggtcatccagcggatagttaataatcagcccactgacacgtt
gcgcgagaagattgtgcaccgccgctttacaggcttcgacgccgcttcgttctaccatcgacacgaccacgctggcac
ccagttgatcggcgcgagatttaatcgccgcgacaatttgcgacggcgcgtgcagggccagactggaggtggcaac
gccaatcagcaacgactgtttgcccgccagttgttgtgccacgcggttaggaatgtaattcagctccgccatcgccgctt
ccacttttcccgcgttttcgcagaaacgtggctggcctggttcaccacgcgggaaacggtctgataagagacaccgg
catactctgcgacatcgtataacgttactggtttcacattcaccaccctgaattgactctcttccgggcgctatcatgccata
ccgcgaaaggttttgcgccattcgatgctagccatgtgagcaaaaggccagcaaaaggccaggaaccgtaaaaag
gccgcgttgctggcgtttttccataggctccgcccccctgacgagcatcacaaaaatcgacgctcaagtcagaggtgg
cgaaacccgacaggactataaagataccaggcgtttccccctggaagctccctcgtgcgctctcctgttccgaccctgc
cgcttaccggatacctgtccgcctttctcccttcgggaagcgtggcgctttctcatagctcacgctgtaggtatctcagttcg

FIG 5 (continued)

gtgtaggtcgttcgctccaagctgggctgtgtgcacgaaccccccgttcagcccgaccgctgcgccttatccggtaact
atcgtcttgagtccaacccggtaagacacgacttatcgccactggcagcagccactggtaacaggattagcagagcg
aggtatgtaggcggtgctacagagttcttgaagtggtggcctaactacggctacactagaagaacagtatttggtatctg
cgctctgctgtagccagttaccttcggaaaaagagttggtagctcttgatccggcaaacaaaccaccgctggtagcggt
ggttttttttgtttgcaagcagcagattacgcgcagaaaaaaaggatctcaagaagatcctttgatcttttctacggggtctg
acgctcagtggaacgaaaactcacgttaagggattttggtcagatctagcaccaggcgtttaagggcaccaataactg
ccttaaaaaaattacgccccgccctgccactcatcgcagtactgttgtaattcattaagcattctgccgacatggaagcc
atcacaaacggcatgatgaacctgaatcgccagcggcatcagcaccttgtcgccttgcgtataatatttgcccatagtg
aaaacgggggcgaagaagttgtccatattggctacgtttaaatcaaaactggtgaaactcacccagggattggctga
gacgaaaaacatattctcaataaacccttagggaaataggccaggttttcaccgtaacacgccacatcttgcgaatat
atgtgtagaaactgccggaaatcgtcgtggtattcactccagagcgatgaaaacgtttcagtttgctcatggaaaacggt
gtaacaagggtgaacactatcccatatcaccagctcaccgtctttcattgccatacggaactccgggtgagcattcatc
aggcgggcaagaatgtgaataaaggccggataaaacttgtgcttattttctttacggtctttaaaaaggccgtaatatcc
agctgaacggtctggttataggtacattgagcaactgactgaaatgcctcaaaatgttctttacgatgccattgggatata
tcaacggtggtatatccagtgatttttttctccattttagcttccttagctcctgaaaatctcgataactcaaaaaatacgccc
ggtagtgatcttatttcattatggtgaaagttggaacctcacccgacgtctaatgtgagttagctcactcattaggcacccc
aggctttacactttatgcttccggctcgtatgttgtgtggaattgtgagcggataacaatttcacacaggaaacagctatga
ccatgattacgaatttctagataacgagggcaaaaa

SEQUENCE LISTING

<160> NUMBER OF SEQ ID NOS: 65

<210> SEQ ID NO 1
<211> LENGTH: 360
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 1

```
caggtgcaat tggtggaaag cggcggcggc ctggtgcaac cgggcggcag cctgcgtctg      60
agctgcgcgg cctccggatt tacctttcct tctcattgga tgtcttgggt gcgccaagcc     120
cctgggaagg gtctcgagtg ggtgagcaat ggtatctttt ctgatggtag cgctacctat     180
tatgcggata gcgtgaaagg ccgttttacc atttcacgtg ataattcgaa aaacaccctg     240
tatctgcaaa tgaacagcct gcgtgcggaa gatacggccg tgtattattg cgcgcgtttt     300
cagggttatg gtggtggttt tgattattgg ggccaaggca ccctggtgac ggttagctca     360
```

<210> SEQ ID NO 2
<211> LENGTH: 354
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 2

```
caggtgcaat tggtggaaag cggcggcggc ctggtgcaac cgggcggcag cctgcgtctg      60
agctgcgcgg cctccggatt tacctttcct tctcattgga tgtcttgggt gcgccaagcc     120
cctgggaagg gtctcgagtg ggtgagcaat atttggcgtg gtccttatat ttattatgct     180
gattctgtta agggtcgttt taccatttca cgtgataatt cgaaaaacac cctgtatctg     240
caaatgaaca gcctgcgtgc ggaagatacg gccgtgtatt attgcgcgcg ttttcagggt     300
tatggtggtg gttttgatta ttggggccaa ggcaccctgg tgacggttag ctca           354
```

<210> SEQ ID NO 3
<211> LENGTH: 345
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 3

```
caggtgcaat tggtggaaag cggcggcggc ctggtgcaac cgggcggcag cctgcgtctg      60
agctgcgcgg cctccggatt tacctttcct tcttattgga tgaattgggt gcgccaagcc     120
cctgggaagg gtctcgagtg ggtgagcggt atctcttatt ctggtagcga gacctattat     180
gcggatagcg tgaaaggccg ttttaccatt tcacgtgata attcgaaaaa caccctgtat     240
ctgcaaatga acagcctgcg tgcggaagat acggccgtgt attattgcgc gcgtggtttt     300
ggtactgatt tttggggcca aggcaccctg gtgacggtta gctca                     345
```

<210> SEQ ID NO 4
<211> LENGTH: 351
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 4

| caggtgcaat tggtggaaag cggcggcggc ctggtgcaac cgggcggcag cctgcgtctg | 60 |
| agctgcgcgg cctccggatt tacctttcct tcttattgga tgaattgggt gcgccaagcc | 120 |
| cctgggaagg gtctcgagtg ggtgagcggt attgagaata agtatgctgg tggtgctact | 180 |
| tattatgctg cttctgttaa gggtcgtttt accatttcac gtgataattc gaaaaacacc | 240 |
| ctgtatctgc aaatgaacag cctgcgtgcg gaagatacgg ccgtgtatta ttgcgcgcgt | 300 |
| ggttttggta ctgattttg gggccaaggc accctggtga cggttagctc a | 351 |

<210> SEQ ID NO 5
<211> LENGTH: 351
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 5

| caggtgcaat tggtggaaag cggcggcggc ctggtgcaac cgggcggcag cctgcgtctg | 60 |
| agctgcgcgg cctccggatt tacctttcct tcttattgga tgaattgggt gcgccaagcc | 120 |
| cctgggaagg gtctcgagtg ggtgagcggt attgagaata agcgtgctgg tggtgctact | 180 |
| ttttatgctg cttccgttaa gggtcgtttt accatttcac gtgataattc gaaaaacacc | 240 |
| ctgtatctgc aaatgaacag cctgcgtgcg gaagatacgg ccgtgtatta ttgcgcgcgt | 300 |
| ggttttggta ctgattttg gggccaaggc accctggtga cggttagctc a | 351 |

<210> SEQ ID NO 6
<211> LENGTH: 351
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 6

| caggtgcaat tggtggaaag cggcggcggc ctggtgcaac cgggcggcag cctgcgtctg | 60 |
| agctgcgcgg cctccggatt tacctttcct tcttattgga tgaattgggt gcgccaagcc | 120 |
| cctgggaagg gtctcgagtg ggtgagcggt attgagtcta agtgggctgg tggtgctact | 180 |
| tattatgctg ctggtgttaa gggtcgtttt accatttcac gtgataattc gaaaaacacc | 240 |
| ctgtatctgc aaatgaacag cctgcgtgcg gaagatacgg ccgtgtatta ttgcgcgcgt | 300 |
| ggttttggta ctgattttg gggccaaggc accctggtga cggttagctc a | 351 |

<210> SEQ ID NO 7
<211> LENGTH: 345
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 7

| caggtgcaat tggtggaaag cggcggcggc ctggtgcaac cgggcggcag cctgcgtctg | 60 |
| agctgcgcgg cctccggatt tacctttcct tcttattgga tgaattgggt gcgccaagcc | 120 |
| cctgggaagg gtctcgagtg ggtgagcggt atctcttatt ctggtagcga gacctattat | 180 |
| gcggatagcg tgaaaggccg ttttaccatt tcacgtgata attcgaaaaa caccctgtat | 240 |

```
ctgcaaatga acagcctgcg tgcggaagat acggccgtgt attattgcgc gcgtggtttt    300
ggtactgatt tttggggcca aggcaccctg gtgacggtta gctca                    345
```

<210> SEQ ID NO 8
<211> LENGTH: 351
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 8

```
caggtgcaat tggtggaaag cggcggcggc ctggtgcaac cgggcggcag cctgcgtctg    60
agctgcgcgg cctccggatt tacctttcct tcttattgga tgaattgggt gcgccaagcc   120
cctgggaagg gtctcgagtg ggtgagcggt attgagaata agcgtgctgg tgttgctact   180
ttttatgctg cttccgttaa gggtcgtttt accatttcac gtgataattc gaaaaacacc   240
ctgtatctgc aaatgaacag cctgcgtgcg gaagatacgg ccgtgtatta ttgcgcgcgt   300
ggttttggta ctgattttg gggccaaggc accctggtga cggttagctc a              351
```

<210> SEQ ID NO 9
<211> LENGTH: 351
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 9

```
caggtgcaat tggtggaaag cggcggcggc ctggtgcaac cgggcggcag cctgcgtctg    60
agctgcgcgg cctccggatt tacctttcct tcttattgga tgaattgggt gcgccaagcc   120
cctgggaagg gtctcgagtg ggtgagcggt attgagtcta agtgggctgg tgttgctact   180
tattatgctg ctggtgttaa gggtcgtttt accatttcac gtgataattc gaaaaacacc   240
ctgtatctgc aaatgaacag cctgcgtgcg gaagatacgg ccgtgtatta ttgcgcgcgt   300
ggttttggta ctgatttttg gggccaaggc accctggtga cggttagctc a             351
```

<210> SEQ ID NO 10
<211> LENGTH: 351
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 10

```
caggtgcaat tggtggaaag cggcggcggc ctggtgcaac cgggcggcag cctgcgtctg    60
agctgcgcgg cctccggatt tacctttcct tcttattgga tgaattgggt gcgccaagcc   120
cctgggaagg gtctcgagtg ggtgagcggt attgagaata agtatgctgg tgttgctact   180
tattatgctg cttctgttaa gggtcgtttt accatttcac gtgataattc gaaaaacacc   240
ctgtatctgc aaatgaacag cctgcgtgcg gaagatacgg ccgtgtatta ttgcgcgcgt   300
ggttttggta ctgatttttg gggccaaggc accctggtga cggttagctc a             351
```

<210> SEQ ID NO 11
<211> LENGTH: 120
<212> TYPE: PRT
<213> ORGANISM: Artificial Sequence

```
<220> FEATURE:
<223> OTHER INFORMATION: Description of Artificial Sequence: Synthetic
      construct

<400> SEQUENCE: 11

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Trp Met Ser Trp Val Arg Gln Ala Pro Gly Lys Gly Leu Glu Trp Val
        35                  40                  45

Ser Asn Gly Ile Phe Ser Asp Gly Ser Ala Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Phe Gln Gly Tyr Gly Gly Gly Phe Asp Tyr Trp Gly Gln
            100                 105                 110

Gly Thr Leu Val Thr Val Ser Ser
        115                 120

<210> SEQ ID NO 12
<211> LENGTH: 118
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 12

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Trp Met Ser Trp Val Arg Gln Ala Pro Gly Lys Gly Leu Glu Trp Val
        35                  40                  45

Ser Asn Ile Trp Arg Gly Pro Tyr Ile Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Phe Gln Gly Tyr Gly Gly Gly Phe Asp Tyr Trp Gly Gln Gly Thr
            100                 105                 110

Leu Val Thr Val Ser Ser
        115

<210> SEQ ID NO 13
<211> LENGTH: 115
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 13

Gln Val Gln Leu Val Glu Ser Gly Gly Gly Leu Val Gln Pro Gly Gly
1               5                   10                  15
```

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
            35                  40                  45

Ser Gly Ile Ser Tyr Ser Gly Ser Glu Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Phe Gly Thr Asp Phe Trp Gly Gln Gly Thr Leu Val Thr
            100                 105                 110

Val Ser Ser
        115

<210> SEQ ID NO 14
<211> LENGTH: 117
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 14

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
            35                  40                  45

Ser Gly Ile Glu Asn Lys Tyr Ala Gly Gly Ala Thr Tyr Tyr Ala Ala
 50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                85                  90                  95

Tyr Cys Ala Arg Gly Phe Gly Thr Asp Phe Trp Gly Gln Gly Thr Leu
            100                 105                 110

Val Thr Val Ser Ser
        115

<210> SEQ ID NO 15
<211> LENGTH: 117
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 15

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
            35                  40                  45

Ser Gly Ile Glu Asn Lys Arg Ala Gly Gly Ala Thr Phe Tyr Ala Ala
 50                  55                  60

```
Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Arg Gly Phe Gly Thr Asp Phe Trp Gly Gln Gly Thr Leu
            100                 105                 110

Val Thr Val Ser Ser
            115

<210> SEQ ID NO 16
<211> LENGTH: 117
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 16

Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Trp Met Asn Trp Val Arg Gln Ala Pro Gly Lys Gly Leu Glu Trp Val
         35                  40                  45

Ser Gly Ile Glu Ser Lys Trp Ala Gly Ala Thr Tyr Tyr Ala Ala
 50                  55                  60

Gly Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Arg Gly Phe Gly Thr Asp Phe Trp Gly Gln Gly Thr Leu
            100                 105                 110

Val Thr Val Ser Ser
            115

<210> SEQ ID NO 17
<211> LENGTH: 115
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 17

Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Trp Met Asn Trp Val Arg Gln Ala Pro Gly Lys Gly Leu Glu Trp Val
         35                  40                  45

Ser Gly Ile Ser Tyr Ser Gly Ser Glu Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Phe Gly Thr Asp Phe Trp Gly Gln Gly Thr Leu Val Thr
            100                 105                 110
```

Val Ser Ser
        115

<210> SEQ ID NO 18
<211> LENGTH: 117
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 18

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
        35                  40                  45

Ser Gly Ile Glu Asn Lys Arg Ala Gly Ala Thr Phe Tyr Ala Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Gly Phe Gly Thr Asp Phe Trp Gly Gln Gly Thr Leu
            100                 105                 110

Val Thr Val Ser Ser
        115

<210> SEQ ID NO 19
<211> LENGTH: 117
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 19

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
        35                  40                  45

Ser Gly Ile Glu Ser Lys Trp Ala Gly Gly Ala Thr Tyr Tyr Ala Ala
    50                  55                  60

Gly Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Gly Phe Gly Thr Asp Phe Trp Gly Gln Gly Thr Leu
            100                 105                 110

Val Thr Val Ser Ser
        115

<210> SEQ ID NO 20
<211> LENGTH: 117
<212> TYPE: PRT
<213> ORGANISM: Artificial Sequence
<220> FEATURE:

<223> OTHER INFORMATION: Description of Artificial Sequence: Synthetic
      construct

<400> SEQUENCE: 20

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
        35                  40                  45

Ser Gly Ile Glu Asn Lys Tyr Ala Gly Gly Ala Thr Tyr Tyr Ala Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Gly Phe Gly Thr Asp Phe Trp Gly Gln Gly Thr Leu
            100                 105                 110

Val Thr Val Ser Ser
        115

<210> SEQ ID NO 21
<211> LENGTH: 324
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 21
gatatcgaac tgacccagcc gccttcagtg agcgttgcac aggtcagac cgcgcgtatc      60 tcgtgtagcg gcgataatct tcctggtaag tatgttcatt ggtaccagca gaaacccggg    120
caggcgccag ttcttgtgat ttattatgat tctaatcgtc cctcaggcat cccggaacgc    180
tttagcggat ccaacagcgg caacaccgcg accctgacca ttagcggcac tcaggcggaa    240
gacgaagcgg attattattg ccagtctcgt actcagacta ctattgtgtt tggcggcggc    300
acgaagttaa ccgttcttgg ccag                                            324

<210> SEQ ID NO 22
<211> LENGTH: 324
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 22
gatatcgaac tgacccagcc gccttcagtg agcgttgcac aggtcagac cgcgcgtatc      60 tcgtgtagcg gcgataatct tcctggtaag tatgttcatt ggtaccagca gaaacccggg    120
caggcgccag ttcttgtgat ttattatgat tctaatcgtc cctcaggcat cccggaacgc    180
tttagcggat ccaacagcgg caacaccgcg accctgacca ttagcggcac tcaggcggaa    240
gacgaagcgg attattattg ccagtctcgt actcagacta ctattgtgtt tggcggcggc    300
acgaagttaa ccgttcttgg ccag                                            324

<210> SEQ ID NO 23
<211> LENGTH: 318
<212> TYPE: DNA

<213> ORGANISM: Artificial Sequence
<220> FEATURE:
<223> OTHER INFORMATION: Description of Artificial Sequence: Synthetic
      construct

<400> SEQUENCE: 23

| | | | | | |
|---|---|---|---|---|---|
| gatatcgaac | tgacccagcc | gccttcagtg | agcgttgcac | caggtcagac | cgcgcgtatc | 60 |
| tcgtgtagcg | gcgattctat | tggtaagaag | tatgcttatt | ggtaccagca | gaaacccggg | 120 |
| caggcgccag | ttcttgtgat | ttataagaag | cgtccctcag | gcatcccgga | acgctttagc | 180 |
| ggatccaaca | gcggcaacac | cgcgaccctg | accattagcg | gcactcaggc | ggaagacgaa | 240 |
| gcggattatt | attgctcttc | ttgggattct | actggtcttg | tgtttggcgg | cggcacgaag | 300 |
| ttaaccgttc | ttggccag | | | | | 318 |

<210> SEQ ID NO 24
<211> LENGTH: 318
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 24

| | | | | | |
|---|---|---|---|---|---|
| gatatcgaac | tgacccagcc | gccttcagtg | agcgttgcac | caggtcagac | cgcgcgtatc | 60 |
| tcgtgtagcg | gcgattctat | tggtaagaag | tatgcttatt | ggtaccagca | gaaacccggg | 120 |
| caggcgccag | ttcttgtgat | ttataagaag | cgtccctcag | gcatcccgga | acgctttagc | 180 |
| ggatccaaca | gcggcaacac | cgcgaccctg | accattagcg | gcactcaggc | ggaagacgaa | 240 |
| gcggattatt | attgctcttc | ttgggattct | actggtcttg | tgtttggcgg | cggcacgaag | 300 |
| ttaaccgttc | ttggccag | | | | | 318 |

<210> SEQ ID NO 25
<211> LENGTH: 318
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 25

| | | | | | |
|---|---|---|---|---|---|
| gatatcgaac | tgacccagcc | gccttcagtg | agcgttgcac | caggtcagac | cgcgcgtatc | 60 |
| tcgtgtagcg | gcgattctat | tggtaagaag | tatgcttatt | ggtaccagca | gaaacccggg | 120 |
| caggcgccag | ttcttgtgat | ttataagaag | cgtccctcag | gcatcccgga | acgctttagc | 180 |
| ggatccaaca | gcggcaacac | cgcgaccctg | accattagcg | gcactcaggc | ggaagacgaa | 240 |
| gcggattatt | attgctcttc | ttgggattct | actggtcttg | tgtttggcgg | cggcacgaag | 300 |
| ttaaccgttc | ttggccag | | | | | 318 |

<210> SEQ ID NO 26
<211> LENGTH: 318
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 26

| | | | | | |
|---|---|---|---|---|---|
| gatatcgaac | tgacccagcc | gccttcagtg | agcgttgcac | caggtcagac | cgcgcgtatc | 60 |
| tcgtgtagcg | gcgattctat | tggtaagaag | tatgcttatt | ggtaccagca | gaaacccggg | 120 |

```
caggcgccag ttcttgtgat ttataagaag cgtccctcag gcatcccgga acgctttagc      180
ggatccaaca gcggcaacac cgcgaccctg accattagcg gcactcaggc ggaagacgaa      240
gcggattatt attgctcttc ttgggattct actggtcttg tgtttggcgg cggcacgaag      300
ttaaccgttc ttggccag                                                    318

<210> SEQ ID NO 27
<211> LENGTH: 318
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 27
gatatcgaac tgacccagcc gccttcagtg agcgttgcac caggtcagac cgcgcgtatc       60
tcgtgtagcg gcgattctat tggtaagaag tatgcttatt ggtaccagca gaaacccggg      120
caggcgccag ttcttgtgat ttataagaag cgtccctcag gcatcccgga acgctttagc      180
ggatccaaca gcggcaacac cgcgaccctg accattagcg gcactcaggc ggaagacgaa      240
gcggattatt attgctctgc ttggggtgat aagggtatgg tgtttggcgg cggcacgaag      300
ttaaccgttc ttggccag                                                    318

<210> SEQ ID NO 28
<211> LENGTH: 318
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 28
gatatcgaac tgacccagcc gccttcagtg agcgttgcac caggtcagac cgcgcgtatc       60
tcgtgtagcg gcgattctat tggtaagaag tatgcttatt ggtaccagca gaaacccggg      120
caggcgccag ttcttgtgat ttataagaag cgtccctcag gcatcccgga acgctttagc      180
ggatccaaca gcggcaacac cgcgaccctg accattagcg gcactcaggc ggaagacgaa      240
gcggattatt attgctctgc ttggggtgat aagggtatgg tgtttggcgg cggcacgaag      300
ttaaccgttc ttggccag                                                    318

<210> SEQ ID NO 29
<211> LENGTH: 318
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 29
gatatcgaac tgacccagcc gccttcagtg agcgttgcac caggtcagac cgcgcgtatc       60
tcgtgtagcg gcgattctat tggtaagaag tatgcttatt ggtaccagca gaaacccggg      120
caggcgccag ttcttgtgat ttataagaag cgtccctcag gcatcccgga acgctttagc      180
ggatccaaca gcggcaacac cgcgaccctg accattagcg gcactcaggc ggaagacgaa      240
gcggattatt attgctctgc ttggggtgat aagggtatgg tgtttggcgg cggcacgaag      300
ttaaccgttc ttggccag                                                    318
```

```
<210> SEQ ID NO 30
<211> LENGTH: 318
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 30
gatatcgaac tgacccagcc gccttcagtg agcgttgcac caggtcagac cgcgcgtatc      60
tcgtgtagcg gcgattctat tggtaagaag tatgcttatt ggtaccagca gaaacccggg     120
caggcgccag ttcttgtgat ttataagaag cgtccctcag gcatcccgga acgctttagc     180
ggatccaaca gcggcaacac cgcgaccctg accattagcg gcactcaggc ggaagacgaa     240
gcggattatt attgctctgc ttggggtgat aagggtatgg tgtttggcgg cggcacgaag     300
ttaaccgttc ttggccag                                                   318

<210> SEQ ID NO 31
<211> LENGTH: 108
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 31

Asp Ile Glu Leu Thr Gln Pro Pro Ser Val Ser Val Ala Pro Gly Gln
  1               5                  10                  15

Thr Ala Arg Ile Ser Cys Ser Gly Asp Asn Leu Pro Gly Lys Tyr Val
             20                  25                  30

His Trp Tyr Gln Gln Lys Pro Gly Gln Ala Pro Val Leu Val Ile Tyr
         35                  40                  45

Tyr Asp Ser Asn Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Ser Arg Thr Gln Thr Thr Ile Val
                 85                  90                  95

Phe Gly Gly Gly Thr Lys Leu Thr Val Leu Gly Gln
            100                 105

<210> SEQ ID NO 32
<211> LENGTH: 108
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 32

Asp Ile Glu Leu Thr Gln Pro Pro Ser Val Ser Val Ala Pro Gly Gln
  1               5                  10                  15

Thr Ala Arg Ile Ser Cys Ser Gly Asp Asn Leu Pro Gly Lys Tyr Val
             20                  25                  30

His Trp Tyr Gln Gln Lys Pro Gly Gln Ala Pro Val Leu Val Ile Tyr
         35                  40                  45

Tyr Asp Ser Asn Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Glu
 65                  70                  75                  80
```

Asp Glu Ala Asp Tyr Tyr Cys Gln Ser Arg Thr Gln Thr Thr Ile Val
                85                  90                  95

Phe Gly Gly Gly Thr Lys Leu Thr Val Leu Gly Gln
            100                 105

<210> SEQ ID NO 33
<211> LENGTH: 106
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 33

Asp Ile Glu Leu Thr Gln Pro Pro Ser Val Ser Val Ala Pro Gly Gln
1               5                   10                  15

Thr Ala Arg Ile Ser Cys Ser Gly Asp Ser Ile Gly Lys Lys Tyr Ala
            20                  25                  30

Tyr Trp Tyr Gln Gln Lys Pro Gly Gln Ala Pro Val Leu Val Ile Tyr
        35                  40                  45

Lys Lys Arg Pro Ser Gly Ile Pro Glu Arg Phe Ser Gly Ser Asn Ser
    50                  55                  60

Gly Asn Thr Ala Thr Leu Thr Ile Ser Gly Thr Gln Ala Glu Asp Glu
65                  70                  75                  80

Ala Asp Tyr Tyr Cys Ser Ser Trp Asp Ser Thr Gly Leu Val Phe Gly
                85                  90                  95

Gly Gly Thr Lys Leu Thr Val Leu Gly Gln
            100                 105

<210> SEQ ID NO 34
<211> LENGTH: 106
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 34

Asp Ile Glu Leu Thr Gln Pro Pro Ser Val Ser Val Ala Pro Gly Gln
1               5                   10                  15

Thr Ala Arg Ile Ser Cys Ser Gly Asp Ser Ile Gly Lys Lys Tyr Ala
            20                  25                  30

Tyr Trp Tyr Gln Gln Lys Pro Gly Gln Ala Pro Val Leu Val Ile Tyr
        35                  40                  45

Lys Lys Arg Pro Ser Gly Ile Pro Glu Arg Phe Ser Gly Ser Asn Ser
    50                  55                  60

Gly Asn Thr Ala Thr Leu Thr Ile Ser Gly Thr Gln Ala Glu Asp Glu
65                  70                  75                  80

Ala Asp Tyr Tyr Cys Ser Ser Trp Asp Ser Thr Gly Leu Val Phe Gly
                85                  90                  95

Gly Gly Thr Lys Leu Thr Val Leu Gly Gln
            100                 105

<210> SEQ ID NO 35
<211> LENGTH: 106
<212> TYPE: PRT
<213> ORGANISM: Artificial Sequence
<220> FEATURE:
<223> OTHER INFORMATION: Description of Artificial Sequence: Synthetic
      construct -continued

<400> SEQUENCE: 35

Asp Ile Glu Leu Thr Gln Pro Pro Ser Val Ser Val Ala Pro Gly Gln
1               5                   10                  15

Thr Ala Arg Ile Ser Cys Ser Gly Asp Ser Ile Gly Lys Lys Tyr Ala
            20                  25                  30

Tyr Trp Tyr Gln Gln Lys Pro Gly Gln Ala Pro Val Leu Val Ile Tyr
        35                  40                  45

Lys Lys Arg Pro Ser Gly Ile Pro Glu Arg Phe Ser Gly Ser Asn Ser
    50                  55                  60

Gly Asn Thr Ala Thr Leu Thr Ile Ser Gly Thr Gln Ala Glu Asp Glu
65                  70                  75                  80

Ala Asp Tyr Tyr Cys Ser Ser Trp Asp Ser Thr Gly Leu Val Phe Gly
                85                  90                  95

Gly Gly Thr Lys Leu Thr Val Leu Gly Gln
            100                 105

<210> SEQ ID NO 36
<211> LENGTH: 106
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 36

Asp Ile Glu Leu Thr Gln Pro Pro Ser Val Ser Val Ala Pro Gly Gln
1               5                   10                  15

Thr Ala Arg Ile Ser Cys Ser Gly Asp Ser Ile Gly Lys Lys Tyr Ala
            20                  25                  30

Tyr Trp Tyr Gln Gln Lys Pro Gly Gln Ala Pro Val Leu Val Ile Tyr
        35                  40                  45

Lys Lys Arg Pro Ser Gly Ile Pro Glu Arg Phe Ser Gly Ser Asn Ser
    50                  55                  60

Gly Asn Thr Ala Thr Leu Thr Ile Ser Gly Thr Gln Ala Glu Asp Glu
65                  70                  75                  80

Ala Asp Tyr Tyr Cys Ser Ser Trp Asp Ser Thr Gly Leu Val Phe Gly
                85                  90                  95

Gly Gly Thr Lys Leu Thr Val Leu Gly Gln
            100                 105

<210> SEQ ID NO 37
<211> LENGTH: 106
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 37

Asp Ile Glu Leu Thr Gln Pro Pro Ser Val Ser Val Ala Pro Gly Gln
1               5                   10                  15

Thr Ala Arg Ile Ser Cys Ser Gly Asp Ser Ile Gly Lys Lys Tyr Ala
            20                  25                  30

Tyr Trp Tyr Gln Gln Lys Pro Gly Gln Ala Pro Val Leu Val Ile Tyr
        35                  40                  45

Lys Lys Arg Pro Ser Gly Ile Pro Glu Arg Phe Ser Gly Ser Asn Ser
    50                  55                  60

Gly Asn Thr Ala Thr Leu Thr Ile Ser Gly Thr Gln Ala Glu Asp Glu
65                  70                  75                  80

Ala Asp Tyr Tyr Cys Ser Ala Trp Gly Asp Lys Gly Met Val Phe Gly
                85                  90                  95

Gly Gly Thr Lys Leu Thr Val Leu Gly Gln
            100                 105

<210> SEQ ID NO 38
<211> LENGTH: 106
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 38

Asp Ile Glu Leu Thr Gln Pro Pro Ser Val Ser Val Ala Pro Gly Gln
1               5                   10                  15

Thr Ala Arg Ile Ser Cys Ser Gly Asp Ser Ile Gly Lys Lys Tyr Ala
            20                  25                  30

Tyr Trp Tyr Gln Gln Lys Pro Gly Gln Ala Pro Val Leu Val Ile Tyr
        35                  40                  45

Lys Lys Arg Pro Ser Gly Ile Pro Glu Arg Phe Ser Gly Ser Asn Ser
    50                  55                  60

Gly Asn Thr Ala Thr Leu Thr Ile Ser Gly Thr Gln Ala Glu Asp Glu
65                  70                  75                  80

Ala Asp Tyr Tyr Cys Ser Ala Trp Gly Asp Lys Gly Met Val Phe Gly
                85                  90                  95

Gly Gly Thr Lys Leu Thr Val Leu Gly Gln
            100                 105

<210> SEQ ID NO 39
<211> LENGTH: 106
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 39

Asp Ile Glu Leu Thr Gln Pro Pro Ser Val Ser Val Ala Pro Gly Gln
1               5                   10                  15

Thr Ala Arg Ile Ser Cys Ser Gly Asp Ser Ile Gly Lys Lys Tyr Ala
            20                  25                  30

Tyr Trp Tyr Gln Gln Lys Pro Gly Gln Ala Pro Val Leu Val Ile Tyr
        35                  40                  45

Lys Lys Arg Pro Ser Gly Ile Pro Glu Arg Phe Ser Gly Ser Asn Ser
    50                  55                  60

Gly Asn Thr Ala Thr Leu Thr Ile Ser Gly Thr Gln Ala Glu Asp Glu
65                  70                  75                  80

Ala Asp Tyr Tyr Cys Ser Ala Trp Gly Asp Lys Gly Met Val Phe Gly
                85                  90                  95

Gly Gly Thr Lys Leu Thr Val Leu Gly Gln
            100                 105

<210> SEQ ID NO 40
<211> LENGTH: 106
<212> TYPE: PRT
<213> ORGANISM: Artificial Sequence
<220> FEATURE:

<223> OTHER INFORMATION: Description of Artificial Sequence: Synthetic
      construct

<400> SEQUENCE: 40

Asp Ile Glu Leu Thr Gln Pro Pro Ser Val Ser Val Ala Pro Gly Gln
1               5                   10                  15

Thr Ala Arg Ile Ser Cys Ser Gly Asp Ser Ile Gly Lys Lys Tyr Ala
            20                  25                  30

Tyr Trp Tyr Gln Gln Lys Pro Gly Gln Ala Pro Val Leu Val Ile Tyr
        35                  40                  45

Lys Lys Arg Pro Ser Gly Ile Pro Glu Arg Phe Ser Gly Ser Asn Ser
    50                  55                  60

Gly Asn Thr Ala Thr Leu Thr Ile Ser Gly Thr Gln Ala Glu Asp Glu
65                  70                  75                  80

Ala Asp Tyr Tyr Cys Ser Ala Trp Gly Asp Lys Gly Met Val Phe Gly
                85                  90                  95

Gly Gly Thr Lys Leu Thr Val Leu Gly Gln
            100                 105

<210> SEQ ID NO 41
<211> LENGTH: 120
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 41

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 42
<211> LENGTH: 108
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 42

Asp Ile Glu Leu Thr Gln Pro Pro Ser Val Ser Val Ala Pro Gly Gln
1               5                   10                  15

Thr Ala Arg Ile Ser Cys Ser Gly Asp Ala Leu Gly Asp Lys Tyr Ala
            20                  25                  30

Ser Trp Tyr Gln Gln Lys Pro Gly Gln Ala Pro Val Leu Val Ile Tyr

```
                   35                  40                  45
Asp Asp Ser Asp Arg Pro Ser Gly Ile Pro Glu Arg Phe Ser Gly Ser
               50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Gln His Tyr Thr Thr Pro Pro Val
                 85                  90                  95

Phe Gly Gly Gly Thr Lys Leu Thr Val Leu Gly Gln
               100                 105

<210> SEQ ID NO 43
<211> LENGTH: 4986
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 43
atgaaaaaga cagctatcgc gattgcagtg gcactggctg gtttcgctac cgtagcgcag     60
gccgatatcg aactgaccca gccgccttca gtgagcgttg caccaggtca gaccgcgcgt    120
atctcgtgta gcggcgattc tattggtaag aagtatgctt attggtacca gcagaaaccc    180
gggcaggcgc cagttcttgt gatttataag aagcgtccct caggcatccc ggaacgcttt    240
agcggatcca acagcggcaa caccgcgacc ctgaccatta gcggcactca ggcggaagac    300
gaagcggatt attattgctc ttcttgggat tctactggtc ttgtgtttgg cggcggcacg    360
aagttaaccg ttcttggcca gccgaaagcc gcaccgagtg tgacgctgtt ccgccgagc    420 agcgaagaat gcaggcgaa caaagcgacc ctggtgtgcc tgattagcga cttttatccg    480
ggagccgtga cagtggcctg gaaggcagat agcagcccg tcaaggcggg agtggagacc    540
accacaccct ccaaacaaag caacaacaag tacgcggcca gcagctatct gagcctgacg    600
cctgagcagt ggaagtccca cagaagctac agctgccagg tcacgcatga ggggagcacc    660
gtggaaaaaa ccgttgcgcc gactgaggcc tgataagcat gcgtaggaga aaataaaatg    720
aaacaaagca ctattgcact ggcactctta ccgttgctct tcaccctgt taccaaagcc    780 caggtgcaat tggtggaaag cggcggcggc ctggtgcaac cgggcggcag cctgcgtctg    840
agctgcgcgg cctccggatt tacctttct tcttattgga tgaattgggt gcgccaagcc    900
cctgggaagg gtctcgagtg ggtgagcggt atctcttatt ctggtagcga gacctattat    960
gcggatagcg tgaaaggccg ttttaccatt tcacgtgata attcgaaaaa cacctgtat   1020 ctgcaaatga acagcctgcg tgcggaagat acggccgtgt attattgcgc gcgtggtttt   1080
ggtactgatt ttggggcca aggcaccctg gtgacggtta gctcagcgtc gaccaaaggt   1140
ccaagcgtgt tccgctggc tccgagcagc aaaagcacca gcggcggcac ggctgccctg   1200
ggctgcctgg ttaaagatta tttcccggaa ccagtcaccg tgagctggaa cagcggggcg   1260
ctgaccagcg gcgtgcatac cttccggcg gtgctgcaaa gcagcggcct gtatagcctg   1320
agcagcgttg tgaccgtgcc gagcagcagc ttaggcactc agacctatat ttgcaacgtg   1380
aaccataaac cgagcaacac caaagtggat aaaaagtgg aaccgaaaag cgaattcgac   1440
tataaagatg acgatgacaa aggcgcgccg caccatcatc accatcactg ataagcttga   1500
cctgtgaagt gaaaaatggc gcagattgtg cgacatttt tttgtctgcc gtttaattaa   1560
aggggggggg gggccggcct ggggggggt gtacatgaaa ttgtaaacgt taatattttg   1620
```

```
ttaaaattcg cgttaaattt ttgttaaatc agctcatttt ttaaccaata ggccgaaatc    1680
ggcaaaatcc cttataaatc aaaagaatag accgagatag ggttgagtgt tgttccagtt    1740
tggaacaaga gtccactatt aaagaacgtg gactccaacg tcaaagggcg aaaaaccgtc    1800
tatcagggcg atggcccact acgagaacca tcaccctaat caagtttttt ggggtcgagg    1860
tgccgtaaag cactaaatcg gaaccctaaa gggagccccc gatttagagc ttgacgggga    1920
aagccggcga acgtggcgag aaaggaaggg aagaaagcga aaggagcggg cgctagggcg    1980
ctggcaagtg tagcggtcac gctgcgcgta accaccacac ccgccgcgct taatgcgccg    2040
ctacagggcg cgtgctagac tagtgtttaa accggaccgg gggggggctt aagtgggctg    2100
caaaacaaaa cggcctcctg tcaggaagcc gcttttatcg ggtagcctca ctgcccgctt    2160
tccagtcggg aaacctgtcg tgccagctgc atcagtgaat cggccaacgc gcggggagag    2220
gcggtttgcg tattgggagc cagggtggtt tttcttttca ccagtgagac gggcaacagc    2280
tgattgccct tcaccgcctg gccctgagag agttgcagca agcggtccac gctggtttgc    2340
cccagcaggc gaaaatcctg tttgatggtg gtcagcggcg ggatataaca tgagctgtcc    2400
tcggtatcgt cgtatcccac taccgagatg tccgcaccaa cgcgcagccc ggactcggta    2460
atggcacgca ttgcgcccag cgccatctga tcgttggcaa ccagcatcgc agtgggaacg    2520
atgccctcat tcagcatttg catggttttgt tgaaaaccgg acatggcact ccagtcgcct    2580
tcccgttccg ctatcggctg aatttgattg cgagtgagat atttatgcca gccagccaga    2640
cgcagacgcg ccgagacaga acttaatggg ccagctaaca gcgcgatttg ctggtggccc    2700
aatgcgacca gatgctccac gcccagtcgc gtaccgtcct catgggagaa aataatactg    2760
ttgatgggtg tctggtcaga gacatcaaga ataacgccg gaacattagt gcaggcagct    2820
tccacagcaa tagcatcctg gtcatccagc ggatagttaa taatcagccc actgacacgt    2880
tgcgcgagaa gattgtgcac cgccgcttta caggcttcga cgccgcttcg ttctaccatc    2940
gacacgacca cgctggcacc cagttgatcg gcgcgagatt taatcgccgc gacaatttgc    3000
gacggcgcgt gcagggccag actggaggtg gcaacgccaa tcagcaacga ctgtttgccc    3060
gccagttgtt gtgccacgcg gttaggaatg taattcagct ccgccatcgc cgcttccact    3120
ttttcccgcg ttttcgcaga aacgtggctg gcctggttca ccacgcggga aacggtctga    3180
taagagacac cggcatactc tgcgacatcg tataacgtta ctggtttcac attcaccacc    3240
ctgaattgac tctcttccgg cgctatcat gccataccgc gaaaggtttt gcgccattcg    3300
atgctagcca tgtgagcaaa aggccagcaa aaggccagga accgtaaaaa ggccgcgttg    3360
ctggcgtttt tccataggct ccgcccccct gacgagcatc acaaaaatcg acgctcaagt    3420
cagaggtggc gaaacccgac aggactataa agataccagg cgtttccccc tggaagctcc    3480
ctcgtgcgct ctcctgttcc gaccctgccg cttaccggat acctgtccgc ctttctccct    3540
tcgggaagcg tggcgctttc tcatagctca cgctgtaggt atctcagttc ggtgtaggtc    3600
gttcgctcca agctgggctg tgtgcacgaa ccccccgttc agcccgaccg ctgcgcctta    3660
tccggtaact atcgtcttga gtccaacccg gtaagacacg acttatcgcc actggcagca    3720
gccactggta acaggattag cagagcgagg tatgtaggcg gtgctacaga gttcttgaag    3780
tggtggccta actacggcta cactagaaga acagtatttg gtatctgcgc tctgctgtag    3840
ccagttacct tcggaaaaag agttggtagc tcttgatccg gcaaacaaac caccgctggt    3900
agcggtggtt tttttgtttg caagcagcag attacgcgca gaaaaaaagg atctcaagaa    3960
gatcctttga tcttttctac ggggtctgac gctcagtgga acgaaaactc acgttaaggg    4020
```

```
attttggtca gatctagcac caggcgttta agggcaccaa taactgcctt aaaaaaatta    4080
cgccccgccc tgccactcat cgcagtactg ttgtaattca ttaagcattc tgccgacatg    4140
gaagccatca caaacggcat gatgaacctg aatcgccagc ggcatcagca ccttgtcgcc    4200
ttgcgtataa tatttgccca tagtgaaaac gggggcgaag aagttgtcca tattggctac    4260
gtttaaatca aaactggtga aactcaccca gggattggct gagacgaaaa acatattctc    4320
aataaaccct ttagggaaat aggccaggtt ttcaccgtaa cacgccacat cttgcgaata    4380
tatgtgtaga aactgccgga aatcgtcgtg gtattcactc cagagcgatg aaaacgtttc    4440
agtttgctca tggaaaacgg tgtaacaagg gtgaacacta tcccatatca ccagctcacc    4500
gtctttcatt gccatacgga actccgggtg agcattcatc aggcgggcaa gaatgtgaat    4560
aaaggccgga taaaacttgt gcttattttt ctttacggtc tttaaaaagg ccgtaatatc    4620
cagctgaacg gtctggttat aggtacattg agcaactgac tgaaatgcct caaaatgttc    4680
tttacgatgc cattgggata tatcaacggt ggtatatcca gtgatttttt tctccatttt    4740
agcttcctta gctcctgaaa atctcgataa ctcaaaaaat acgcccggta gtgatcttat    4800
ttcattatgg tgaaagttgg aacctcaccc gacgtctaat gtgagttagc tcactcatta    4860 ggcacccag gctttacact ttatgcttcc ggctcgtatg ttgtgtggaa ttgtgagcgg    4920
ataacaattt cacacaggaa acagctatga ccatgattac gaatttctag ataacgaggg    4980
caaaaa                                                              4986

<210> SEQ ID NO 44
<211> LENGTH: 345
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 44
caggtgcaat tggttcagtc tggcgcggaa gtgaaaaaac cgggcagcag cgtgaaagtg     60
agctgcaaag cctccggagg cacttttaat tcttttctta tttcttgggt gcgccaagcc    120
cctgggcagg gtctcgagtg gatgggcggt atcattccga ttttggcac tgcgaattac    180 gcgcagaagt ttcagggccg ggtgaccatt accgcggatg aaagcaccag caccgcgtat    240
atggaactga gcagcctgcg tagcgaagat acggccgtgt attattgcgc gcgtaagttt    300
atttctgatt cttggggcca aggcacccctg gtgacggtta gctca                   345

<210> SEQ ID NO 45
<211> LENGTH: 345
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 45
caggtgcaat tggttcagtc tggcgcggaa gtgaaaaaac cgggcagcag cgtgaaagtg     60
agctgcaaag cctccggagg cacttttaat tcttttctta tttcttgggt gcgccaagcc    120
cctgggcagg gtctcgagtg gatgggcgct atttctcctt gggatggtgt tactggttat    180
gctcagaagt ttcagggtcg ggtgaccatt accgcggatg aaagcaccag caccgcgtat    240
atggaactga gcagcctgcg tagcgaagat acggccgtgt attattgcgc gcgtaagttt    300
```

```
atttctgatt cttggggcca aggcaccctg gtgacggtta gctca              345
```

<210> SEQ ID NO 46
<211> LENGTH: 345
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 46

```
caggtgcaat tggttcagtc tggcgcggaa gtgaaaaaac cgggcagcag cgtgaaagtg    60
agctgcaaag cctccggagg cactttaat tcttttctta tttcttgggt gcgccaagcc   120
cctgggcagg gtctcgagtg gatgggcggt atcattccga tttttggcac tgcgaattac   180
gcgcagaagt ttcagggccg ggtgaccatt accgcggatg aaagcaccag caccgcgtat   240
atggaactga gcagcctgcg tagcgaagat acggccgtgt attattgcgc gcgtaagttt   300
atttctgatt cttggggcca aggcaccctg gtgacggtta gctca                  345
```

<210> SEQ ID NO 47
<211> LENGTH: 345
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 47

```
caggtgcaat tggttcagtc tggcgcggaa gtgaaaaaac cgggcagcag cgtgaaagtg    60
agctgcaaag cctccggagg cacttttaat tcttttctta tttcttgggt gcgccaagcc   120
cctgggcagg gtctcgagtg gatgggcgct atttctcctt gggatggtgt tactggttat   180
gctcagaagt ttcagggtcg ggtgaccatt accgcggatg aaagcaccag caccgcgtat   240
atggaactga gcagcctgcg tagcgaagat acggccgtgt attattgcgc gcgtaagttt   300
atttctgatt cttggggcca aggcaccctg gtgacggtta gctca                  345
```

<210> SEQ ID NO 48
<211> LENGTH: 351
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 48

```
caggtgcagc tggtcgagtc tggcggcgga ctggtgcagc ctggcggcag cctgagactg    60
agctgtgccg ccagcggctt caccttcagc agctactgga tgaactgggt gaggcaggcc   120
cctggcaagg gcctggagtg ggtgtccggc atcgagaaca gtatgccgg cggagccacc   180
tactacgccg ccagcgtgaa gggccggttc accatcagcc gggacaacag caagaacacc   240
ctgtacctgc agatgaacag cctgagggcc gaggacaccg ccgtgtacta ctgtgccagg   300
ggcttcggca ccgatttctg gggccagggc accctggtga cagtcagctc a            351
```

<210> SEQ ID NO 49
<211> LENGTH: 115
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 49

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ser Phe
            20                  25                  30

Leu Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Lys Phe Ile Ser Asp Ser Trp Gly Gln Gly Thr Leu Val Thr
            100                 105                 110

Val Ser Ser
        115

<210> SEQ ID NO 50
<211> LENGTH: 115
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 50

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ser Phe
            20                  25                  30

Leu Ile Ser Trp Val Arg Gln Ala Pro Gly Gln Gly Leu Glu Trp Met
        35                  40                  45

Gly Ala Ile Ser Pro Trp Asp Gly Val Thr Gly Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Lys Phe Ile Ser Asp Ser Trp Gly Gln Gly Thr Leu Val Thr
            100                 105                 110

Val Ser Ser
        115

<210> SEQ ID NO 51
<211> LENGTH: 115
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 51

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ser Phe
            20                  25                  30

Leu Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Lys Phe Ile Ser Asp Ser Trp Gly Gln Gly Thr Leu Val Thr
                100                 105                 110

Val Ser Ser
        115

<210> SEQ ID NO 52
<211> LENGTH: 115
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 52

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Asn Ser Phe
                 20                  25                  30

Leu Ile Ser Trp Val Arg Gln Ala Pro Gly Gln Gly Leu Glu Trp Met
            35                  40                  45

Gly Ala Ile Ser Pro Trp Asp Gly Val Thr Gly Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Lys Phe Ile Ser Asp Ser Trp Gly Gln Gly Thr Leu Val Thr
                100                 105                 110

Val Ser Ser
        115

<210> SEQ ID NO 53
<211> LENGTH: 327
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 53
gatatccaga tgacccagag cccgtctagc ctgagcgcga gcgtgggtga tcgtgtgacc        60
attacctgca gcgagcca gactattaat aattatctga ttggtacca gcagaaacca       120 ggtaaagcac cgaaactatt aatttatact gcttctaatt tgcaaagcgg ggtcccgtcc       180
cgttttagcg gctctggatc cggcactgat tttaccctga ccattagcag cctgcaacct       240
gaagactttg cggtttatta ttgccagcag tattctggtt ctcctatgac ctttggccag       300
ggtacgaaag ttgaaattaa acgtacg                                          327

<210> SEQ ID NO 54
<211> LENGTH: 327

```
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 54
gatatccaga tgacccagag cccgtctagc ctgagcgcga gcgtgggtga tcgtgtgacc      60
attacctgca gagcgagcca gactattaat aattatctga attggtacca gcagaaacca     120
ggtaaagcac cgaaactatt aatttatact gcttctaatt tgcaaagcgg ggtcccgtcc     180
cgttttagcg gctctggatc cggcactgat tttaccctga ccattagcag cctgcaacct     240
gaagactttg cggtttatta ttgccagcag tattctggtt ctcctatgac ctttggccag     300
ggtacgaaag ttgaaattaa acgtacg                                          327

<210> SEQ ID NO 55
<211> LENGTH: 327
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 55
gatatccaga tgacccagag cccgtctagc ctgagcgcga gcgtgggtga tcgtgtgacc      60
attacctgca gagcgagcca gactattaat aattatctga attggtacca gcagaaacca     120
ggtaaagcac cgaaactatt aatttatact gcttctaatt tgcaaagcgg ggtcccgtcc     180
cgttttagcg gctctggatc cggcactgat tttaccctga ccattagcag cctgcaacct     240
gaagactttg cgacctatta ttgccagcag tattcttggg ttcctcatac ctttggccag     300
ggtacgaaag ttgaaattaa acgtacg                                          327

<210> SEQ ID NO 56
<211> LENGTH: 327
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 56
gatatccaga tgacccagag cccgtctagc ctgagcgcga gcgtgggtga tcgtgtgacc      60
attacctgca gagcgagcca gactattaat aattatctga attggtacca gcagaaacca     120
ggtaaagcac cgaaactatt aatttatact gcttctaatt tgcaaagcgg ggtcccgtcc     180
cgttttagcg gctctggatc cggcactgat tttaccctga ccattagcag cctgcaacct     240
gaagactttg cgacctatta ttgccagcag tattcttggg ttcctcatac ctttggccag     300
ggtacgaaag ttgaaattaa acgtacg                                          327

<210> SEQ ID NO 57
<211> LENGTH: 318
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 57
gacatcgagc tgacccagcc ccccagcgtg tctgtggccc ctggccagac cgcccggatc      60
```

-continued

```
agctgctccg gcgacagcat cggcaagaag tacgcctact ggtatcagca gaagcccggc    120
caggcccccg tgctggtgat ctacaagaag cggcccagcg gcatccccga gcggttcagc    180
ggcagcaaca gcggcaacac cgccaccctg accatcagcg gcacccaggc cgaggacgag    240
gccgactact actgctccgc ctggggcgac aagggcatgg tgtttggcgg cggaacaaag    300
ttaaccgtgc tggggcag                                                  318
```

<210> SEQ ID NO 58
<211> LENGTH: 109
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 58

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Asn Asn Tyr
            20                  25                  30

Leu Asn Trp Tyr Gln Gln Lys Pro Gly Lys Ala Pro Lys Leu Leu Ile
        35                  40                  45

Tyr Thr Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Ser Gly Ser Pro Met
                85                  90                  95

Thr Phe Gly Gln Gly Thr Lys Val Glu Ile Lys Arg Thr
            100                 105
```

<210> SEQ ID NO 59
<211> LENGTH: 109
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 59

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Asn Asn Tyr
            20                  25                  30

Leu Asn Trp Tyr Gln Gln Lys Pro Gly Lys Ala Pro Lys Leu Leu Ile
        35                  40                  45

Tyr Thr Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Ser Gly Ser Pro Met
                85                  90                  95

Thr Phe Gly Gln Gly Thr Lys Val Glu Ile Lys Arg Thr
            100                 105
```

<210> SEQ ID NO 60
<211> LENGTH: 109
<212> TYPE: PRT
<213> ORGANISM: Artificial Sequence

```
<220> FEATURE:
<223> OTHER INFORMATION: Description of Artificial Sequence: Synthetic
      construct

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Asn Asn Tyr
            20                  25                  30

Leu Asn Trp Tyr Gln Gln Lys Pro Gly Lys Ala Pro Lys Leu Leu Ile
        35                  40                  45

Tyr Thr Ala Ser Asn Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Trp Val Pro His
                85                  90                  95

Thr Phe Gly Gln Gly Thr Lys Val Glu Ile Lys Arg Thr
            100                 105

<210> SEQ ID NO 61
<211> LENGTH: 109
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Asn Asn Tyr
            20                  25                  30

Leu Asn Trp Tyr Gln Gln Lys Pro Gly Lys Ala Pro Lys Leu Leu Ile
        35                  40                  45

Tyr Thr Ala Ser Asn Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Trp Val Pro His
                85                  90                  95

Thr Phe Gly Gln Gly Thr Lys Val Glu Ile Lys Arg Thr
            100                 105

<210> SEQ ID NO 62
<211> LENGTH: 127
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (99)..(116)
<223> OTHER INFORMATION: Variable amino acid

<400> SEQUENCE: 62

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30
```

```
Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Xaa Xaa Xaa Xaa Xaa Xaa Xaa Xaa Xaa Xaa Xaa Xaa Xaa Xaa
            100                 105                 110

Xaa Xaa Xaa Xaa Trp Gly Gln Gly Thr Leu Val Thr Val Ser Ser
            115                 120                 125

<210> SEQ ID NO 63
<211> LENGTH: 109
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (85)
<223> OTHER INFORMATION: Thr or Val
<220> FEATURE:
<221> NAME/KEY: MOD_RES
<222> LOCATION: (89)..(96)
<223> OTHER INFORMATION: Variable amino acid

<400> SEQUENCE: 63

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Xaa Tyr Tyr Cys Xaa Xaa Xaa Xaa Xaa Xaa Xaa Xaa
                85                  90                  95

Thr Phe Gly Gln Gly Thr Lys Val Glu Ile Lys Arg Thr
            100                 105

<210> SEQ ID NO 64
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ttctctggat ccgccaccat gcttctcctg gtgacaagcc                              40

<210> SEQ ID NO 65
<211> LENGTH: 34
<212> TYPE: DNA
<213> ORGANISM: Artificial Sequence
<220> FEATURE:
<223> OTHER INFORMATION: Description of Artificial Sequence: Synthetic
```

-continued

```
    primer
<400> SEQUENCE: 65
accctccaat tgtcaggtaa tttccttcac ggtc                                      34
```

ANTI-GM-CSF ANTIBODIES

CROSS-REFERENCE TO RELATED APPLICATIONS

This application is a Continuation of U.S. application Ser. No. 11/914,599, which is the US National Stage application of PCT/EP2006/004696, filed May 17, 2006, which claims priority from U.S. Provisional Application 60/682,009, filed May 18, 2005. The entire contents of each of the aforementioned applications are incorporated herein by reference.

BACKGROUND OF THE INVENTION

Granulocyte-macrophage colony stimulating factor, GM-CSF, was originally identified as a hemopoietic growth factor. It is produced by a number of cell types including lymphocytes, monocytes, endothelial cells, fibroblasts and some malignant cells (Metcalf et al., 1986; Clark and Kamen, 1987; Hart et al., 1988; Metcalf et al., 1986). In addition to having a function of growth stimulation and differentiation on hemopoietic precursor cells, GM-CSF also was discovered as having a variety of effects on cells of the immune system expressing the GM-CSF receptor (for review see: Hamilton, 2002; de Groot et al., 1998). The most important of these functions is the activation of monocytes, macrophages and granulocytes in several immune and inflammatory processes (Gasson et al., 1990b; Gasson et al., 1990a; Hart et al., 1988; Rapoport et al., 1992).

Mature GM-CSF is a monomeric protein of 127 amino acids with two glycosylation sites. The variable degree of glycosylation results in a molecular weight range between 14 kDa and 35 kDa. Non-glycosylated and glycosylated GM-CSF show similar activity in vitro (Cebon et al., 1990). The crystallographic analysis of GM-CSF revealed a barrel-shaped structure composed of four short alpha helices (Diederichs et al., 1991). The overall folding is similar to other growth factors like growth hormone, interleukin-2 and interleukin-4.

GM-CSF exerts its biological activity by binding to its receptor (Kastelein and Shanafelt, 1993; Sisson and Dinarello, 1988). The most important sites of GM-CSF receptor (GM-CSF-R) expression are on the cell surface of myeloid cells and endothelial cells, whereas lymphocytes are GM-CSF-R negative. The native receptor is composed of at least two subunits, alpha and beta. The alpha subunit imparts ligand specificity and binds GM-CSF with nanomolar affinity (Gearing et al., 1989; Gasson et al., 1986). The beta subunit is also part of the interleukin-3 and interleukin-5 receptor complexes and, in association with the GM-CSF receptor alpha subunit and GM-CSF, leads to the formation of a complex with picomolar binding affinity (Hayashida et al., 1990). The binding domains on GM-CSF for the receptor have been mapped: GM-CSF interacts with the beta subunit of its receptor via a very restricted region in the first alpha helix of GM-CSF (Shanafelt et al., 1991b; Shanafelt et al., 1991a; Lopez et al., 1991). Binding to the alpha subunit could be mapped to the third alpha helix, helix C, the initial residues of the loop joining helices C and D, and to the carboxyterminal tail of GM-CSF (Brown et al., 1994).

Formation of the GM-CSF trimeric receptor complex leads to the activation of complex signaling cascades involving molecules of the JAK/STAT families, Shc, Ras, Raf, the MAP kinases, phosphatidylinositol-3-kinase and NFkB, finally leading to transcription of c-myc, c-fos and c-jun. Activation is mainly induced by the beta subunit of the receptor (Hayashida et al., 1990; Kitamura et al., 1991; Sato et al., 1993). The shared beta subunit is also responsible for the overlapping functions exerted by IL-3, IL-5 and GM-CSF (for review see: de Groot et al., 1998).

Apart from its hemopoietic growth and differentiation stimulating activity, GM-CSF functions especially as a proinflammatory cytokine. Macrophages and monocytes as well as neutrophils and eosinophils become activated by GM-CSF, resulting in the release of other cytokines and chemokines, matrix degrading proteases, increased HLA expression and increased expression of cell adhesion molecules or receptors for CC-chemokines. The latter, in turn, leads to increased chemotaxis of inflammatory cells into inflamed tissue (Chantry et al., 1990; Hamilton, 2002; Sisson and Dinarello, 1988; Zhang et al., 1998; Hamilton et al., 1993; Lopez et al., 1986; Cheng et al., 2001; Gomez-Cambronero et al., 2003). Often, GM-CSF exerts its activity in synergy with other inflammatory stimulating factors like other cytokines or LPS, e.g. neutrophils treated with GM-CSF in combination with e.g. LPS will show increased oxidative burst (Kaufman et al., 1989; Rapoport et al., 1992).

GM-CSF as Target for Anti-Inflammatory Therapy:

Due to its diverse activating functions in the immune system, GM-CSF can be considered as a target for anti-inflammatory therapy. Chronic and acute inflammatory diseases like rheumatoid arthritis (RA), multiple sclerosis (MS), Crohn's disease, psoriasis, asthma, atopic dermatitis or shock may well benefit from the blocking of GM-CSF activity and subsequent reduction of harmful activities of GM-CSF responsive cells (Hamilton, 1993; Zhang et al., 1998; Hamilton, 2002).

Arthritis:

Several groups showed that GM-CSF, as well as its receptor, are present in the synovial joint of arthritis patients (Alvaro-Gracia et al., 1991; Xu et al., 1989; Haworth et al., 1991). Additionally, GM-CSF was shown to cause flare's of rheumatoid arthritis in patients treated with GM-CSF for neutropenia in Felty's syndrome (Hazenberg et al., 1989) or after chemotherapy (de Vries et al., 1991).

First hints on the usefulness of antibodies blocking GM-CSF for the treatment of arthritis came from mouse in vivo studies (Campbell et al., 1997; Campbell et al., 1998; Cook et al., 2001). Specifically, Cook et al. showed that neutralizing antibodies to GM-CSF showed efficacy in a collagen-induced arthritis model. Blocking of GM-CSF led to a reduction of disease severity concerning inflammation, cartilage destruction and progression of disease in initially affected limbs or progression to other limbs.

There are several effects of an anti-GM-CSF therapy from which the patients with rheumatoid arthritis or with other inflammatory diseases could benefit.

Blocking GM-CSF is expected to inhibit or reduce:

a) the activation and number of mature monocytes, macrophages, and neutrophils. Especially neutrophils and macrophages are abundant in synovial fluid and membrane. The macrophage number in the synovium has been shown to correlate with the degree of erosion in RA joints (Mulherin et al., 1996; Burmester et al., 1997). Macrophages are the source of a variety of other proinflammatory cytokines and matrix degrading proteases. Production of $H_2O_2$ by neutrophils is part of the destructive processes taking place in the arthritic joints (Babior, 2000).

b) the differentiation of myeloid dendritic cells (DCs) and activation of synovial DCs (=synoviocytes). GM-CSF upregulates and maintains HLA class II expression on DCs and RA synoviocytes (Alvaro-Gracia J M et al., 1991). DCs are instructed within the joint to acquire functions associated with the selective activation of inflammatory T-cells. Specific HLA-DR alleles have been linked to susceptibility to RA, and activation of T-cells via antigen presentation of DC's may play a crucial role in this type of immune disease (Santiago-Schwarz et al., 2001).

Multiple Sclerosis:

In multiple sclerosis, elevated levels of GM-CSF correlate with the active phase of MS (Carrieri et al., 1998; McQualter et al., 2001) and GM-CSF-/- mice fail to develop disease in the model system for MS, experimental encephalomyelitis, EAE (McQualter et al., 2001).

Asthma:

In asthma, increased amounts of GM-CSF in the lung have been reported (Broide and Firestein, 1991). At the same time eosinophils are elevated, on which GM-CSF in synergy with interleukin-5 acts in three ways: i) it stimulates the differentiation from progenitor cells into eosinophils, ii) it stimulates their functional activation, and iii) it prolongs the survival of eosinophils in the lung (Broide et al., 1992; Yamashita et al., 2002). Thus, reduction of the survival of eosinophils in asthmatic airways by blocking GM-CSF is likely to ameliorate disease. The usefulness of anti-GM-CSF neutralizing antibodies was further shown in a model for murine asthma where the administration of such antibodies led to significant reduction of airway hyperresponsiveness and airway inflammation (Yamashita et al., 2002).

In a different mouse model, LPS-dependent inflammation of the lung could be reduced by application of anti-GM-CSF antibody 22E9 in the mouse (Bozinovski et al., 2003).

Toxic Effects:

Mice homozygous for a disrupted granulocyte/macrophage colony-stimulating factor (GM-CSF) gene develop normally and show no major perturbation of hematopoiesis up to 12 weeks of age. While most GM-CSF-deficient mice are superficially healthy and fertile, all develop a disorganized vascular extracellular matrix with disrupted and reduced collagen bundles and abnormal lungs with impaired pulmonary surfactant clearance and reduced resistance to microbial pathogens in the lung. Features of the latter pathology resemble the human disorder pulmonary alveolar proteinosis (PAP). GM-CSF does, not seem to be essential for the maintenance of normal levels of the major types of mature hematopoietic cells and their precursors in blood, marrow, and spleen. However, they implicate GM-CSF as being essential for normal vascular development, pulmonary physiology, and for resistance to local infection (Stanley et al., 1994; Dranoff et al., 1994; Plenz et al., 2003; Shibata et al., 2001). Recently, a strong association of auto-antibodies to GM-CSF with PAP has additionally implicated GM-CSF signaling abnormalities in the pathogenesis of PAP in humans. Together, these observations demonstrate that GM-CSF has a critical role in regulation of surfactant homeostasis and alveolar macrophage innate immune functions in the lung (Bonfield et al., 2002; Trapnell and Whitsett, 2002; Uchida et al., 2004; Kitamura et al., 1999).

High titers of autoantibodies with blocking activity to GM-CSF have been described in patients with myasthenia gravis. These patients did not show any other autoimmune phenomena or hemopoietic deficiencies or "other obvious clinical correlates" (Meager et al., 1999).

The compound E21R, a modified form of GM-CSF that antagonizes the function of GM-CSF, had been evaluated in a phase I safety trial and was found to have a good safety profile in cancer patients (Olver et al., 2002).

Thus, apart from the lung function, which should be monitored closely, other side effects are not expected when applying an anti-GM-CSF therapy.

So far, only antibodies derived from non-human species with GM-CSF neutralizing function have been generated. For example, EP 0499161 A1 describes an antibody generated by immunization of mice with oligopeptides, the sequence of which is derived from a GM-CSF. Furthermore, the application discloses a method of alleviating in a mammal in need thereof an undesirable effect of GM-CSF, which comprises administering to said mammal a GM-CSF-inhibiting amount of an immunoglobulin. However, that antibody is a murine antibody, rendering it unsuitable for human administration.

Additionally, WO 03/068920 discloses an inhibitory chimeric mouse/human IgG1 antibody. Antibodies that contain non-human sequences are likely to elicit an immune response in the human patient and are not appropriate for the therapeutic administration. For instance, in diseases where long-term treatment is required (e.g. chronic inflammatory diseases like rheumatoid arthritis, asthma and multiple sclerosis), continued administration of a non-human therapeutic agent increases the likelihood of a severe inflammatory reaction and the production of human antibodies that may neutralize the therapeutic agent.

Correspondingly, in light of the great potential for anti-GM-CSF antibody therapy, there is a high need for human anti-GM-CSF antibodies with high affinity that effectively block the GM-CSF/GM-CSF receptor interaction. Additionally, it would be advantageous to have one or more antibodies that can cross-react with GM-CSF of one or more non-human species in order to test their efficacy in animal-based in vivo models.

The present invention satisfies these and other needs by providing fully highly efficacious anti-GM-CSF antibodies, which are described below.

SUMMARY OF THE INVENTION

It is an object of the invention to provide human and humanized antibodies that can effectively block the GM-CSF/GM-CSF receptor interaction.

It is another object of the invention to provide antibodies that are safe for human administration.

It is also an object of the present invention to provide methods for treating disease or and/or conditions associated with the presence of GM-CSF by using one or more antibodies of the invention. These and other objects of the invention are more fully described herein.

In one aspect, the invention provides an antigen-binding region that is specific for human GM-CSF, where the isolated human or humanized antibody or functional fragment thereof is able (i) to block interaction of 0.5 µg/ml human GM-CSF with the alpha chain of human GM-CSF receptor expressed on about $2 \times 10^5$ CHO-K1 cells by at least 50% under the following conditions: (a) the concentration of the human GM-CSF receptor alpha chain expressed on the CHO-K1 cells is similar to the concentration of human GM-CSF receptor alpha chain expressed on about $2 \times 10^5$ CHO-GMRa#11 cells, and (b) the concentration of the isolated human or humanized antibody or functional fragment thereof is about 5 µg/ml; and (ii) to neutralize 0.25 ng/ml human GM-CSF in a TF-1 proliferation assay with an at least five-fold lower $IC_{50}$ value than reference antibody BVD2-21C11 and/or reference antibody MAB215. As used herein, a "TF-1 proliferation assay" is defined as the assay essentially as described in Example 5B. The skilled worker can obtain CHO-K1 cells expressing human GM-CSF receptor alpha chain at a concentration similar to that which is expressed on about 2×10⁵ CHO-GMRa#11 cells by following the teachings provided herein.

The invention additionally provides an isolated human or humanized antibody or functional antibody fragment that contains an antigen-binding region as disclosed herein. Such an antibody or functional fragment thereof may contain an antigen-binding region that contains an H-CDR3 region depicted in SEQ ID NO: 11, 12, 13, 14, 15, 16, 17, 18, 19, 20, 49, 50, 51 or 52; the antigen-binding region may further include an H-CDR2 region depicted in SEQ ID NO: 11, 12, 13, 14, 15, 16, 17, 18, 19, 20, 49, 50, 51 or 52; and the antigen-binding region also may contain an H-CDR1 region depicted in SEQ ID NO: 11, 12, 13, 14, 15, 16, 17, 18, 19, 20, 49, 50, 51 or 52. Such an antibody or functional fragment thereof may contain an antigen-binding region that contains a variable heavy chain depicted in SEQ ID NO: 11, 12, 13, 14, 15, 16, 17, 18, 19, 20, 49, 50, 51 or 52. Such a GM-CSF-specific antibody of the invention may contain an antigen-binding region that contains an L-CDR3 region depicted in SEQ ID NO: 31, 32, 33, 34, 35, 36, 37, 38, 39, 40, 58, 59, 60 or 61; the antigen-binding region may further include an L-CDR2 region depicted in SEQ ID NO: 31, 32, 33, 34, 35, 36, 37, 38, 39, 40, 58, 59, 60 or 61; and the antigen-binding region also may contain an L-CDR1 region depicted in SEQ ID NO: 31, 32, 33, 34, 35, 36, 37, 38, 39, 40, 58, 59, 60 or 61. Such an antibody or functional fragment thereof may contain an antigen-binding region that contains a variable light chain depicted in SEQ ID NO: 31, 32, 33, 34, 35, 36, 37, 38, 39, 40, 58, 59, 60 or 61.

Peptide variants of the sequences disclosed herein are also embraced by the present invention. Accordingly, the invention includes anti-GM-CSF antibodies having a heavy chain amino acid sequence with: at least 60 percent sequence identity in the CDR regions with the CDR regions depicted in SEQ ID NO: 11, 12, 13, 14, 15, 16, 17, 18, 19, 20, 49, 50, 51 or 52; and or at least 80 percent sequence homology in the CDR regions with the CDR regions depicted in SEQ ID NO: 11, 12, 13, 14, 15, 16, 17, 18, 19, 20, 49, 50, 51 or 52. Further included are anti-GM-CSF antibodies having a light chain amino acid sequence with: at least 60 percent sequence identity in the CDR regions with the CDR regions depicted in SEQ ID NO: 31, 32, 33, 34, 35, 36, 37, 38, 39, 40, 58, 59, 60 or 61; and or at least 80 percent sequence homology in the CDR regions with the CDR regions depicted in SEQ ID NO: 31, 32, 33, 34, 35, 36, 37, 38, 39, 40, 58, 59, 60 or 61.

An antibody of the invention may be an IgG (e.g., IgG₁), while an antibody fragment may be a Fab or scFv, for example. An inventive antibody fragment, accordingly, may be, or may contain, an antigen-binding region that behaves in one or more ways as described herein.

The invention also is related to isolated nucleic acid sequences, each of which can encode an antigen-binding region of a human or humanized antibody or a functional antibody fragment that is specific for GM-CSF. Such a nucleic acid sequence may encode a variable heavy chain of an isolated human or humanized antibody or functional fragment thereof comprising SEQ ID NO: 1, 2, 3, 4, 5, 6, 7, 8, 9, 10, 44, 45, 46, 47 or 48, or a nucleic acid sequence that hybridizes under high stringency conditions to the complementary strand of SEQ ID NO: 1, 2, 3, 4, 5, 6, 7, 8, 9, 10, 44, 45, 46, 47 or 48. The nucleic acid might encode a variable light chain of an isolated human or humanized antibody or functional fragment thereof comprising SEQ ID NO: 21, 22, 23, 24, 25, 26, 27, 28, 29, 30, 53, 54, 55, 56 or 57, or a nucleic acid sequence that hybridizes under high stringency conditions to the complementary strand of SEQ ID NO: 21, 22, 23, 24, 25, 26, 27, 28, 29, 30, 53, 54, 55, 56 or 57.

The nucleic acid sequence might encode an antigen-binding region of a human or humanized antibody or a functional antibody fragment that is specific for human GM-CSF, where the antibody or functional fragment thereof is able (i) to block interaction of 0.5 µg/ml human GM-CSF with the alpha chain of human GM-CSF receptor expressed on 2×10⁵ CHO-K1 cells by at least 50% under the following conditions: (a) the concentration of said human GM-CSF receptor alpha chain expressed on said CHO-K1 cells is similar to the concentration of human GM-CSF receptor alpha chain expressed on 2×10⁵ CHO-GMRa#11 cells and (b) the concentration of said isolated human or humanized antibody or functional fragment thereof is about 5 µg/ml, and (ii) to neutralize 0.25 ng/ml human GM-CSF in a TF-1 proliferation assay with an at least five-fold lower $IC_{50}$ value than the reference antibody BVD2-21C11 and/or reference antibody MAB215.

Nucleic acids of the invention are suitable for recombinant production. Thus, the invention also relates to vectors and host cells containing a nucleic acid sequence of the invention. Such host cells might be bacterial or eukaryotic cells.

Compositions of the invention may be used for therapeutic or prophylactic applications. The invention, therefore, includes a pharmaceutical composition containing an inventive antibody (or functional antibody fragment) and a pharmaceutically acceptable carrier or excipient therefor. In a related aspect, the invention provides a method for treating a disorder or condition associated with the undesired presence of GM-CSF or GM-CSF expressing cells. Such method contains the steps of administering to a subject in need thereof an effective amount of the pharmaceutical composition that contains an inventive antibody as described or contemplated herein. Such a disorder or condition might be an inflammatory disease, such as rheumatoid arthritis, multiple sclerosis, Crohn's disease, psoriasis, asthma, atopic dermatitis and shock.

Human or humanized antibodies (and functional fragments thereof) of the present invention may be cross-reactive with rat and/or rhesus (macaca) GM-CSF, as determined by solution equilibrium titration (SET), and/or TF1 proliferation assay.

BRIEF DESCRIPTION OF THE FIGURES

FIG. 1a provides nucleic acid sequences of various novel antibody variable heavy chain regions.

FIG. 1b provides amino acid sequences of various novel antibody variable heavy chain regions. CDR regions HCDR1, HCDR2 and HCDR3 are designated from N- to C-terminus in boldface.

FIG. 2a provides nucleic acid sequences of various novel antibody variable light chain regions.

FIG. 2b provides amino acid sequences of various novel antibody variable light chain regions. CDR regions LCDR1, LCDR2 and LCDR3 are designated from N- to C-terminus in boldface.

FIG. 3 provides amino acid sequences of variable heavy chain regions of consensus-based HuCAL® antibody master gene sequences. CDR regions HCDR1, HCDR2 and HCDR3 are designated from N- to C-terminus in boldface.

FIG. 4 provides amino acid sequences of variable light chain regions of consensus-based HuCAL® antibody master gene sequences. CDR regions LCDR1, LCDR2 and LCDR3 are designated from N- to C-terminus in boldface.

FIG. 5 provides an example of a DNA sequence of pMORPH® X9_MOR03929_FH expression vector (SEQ ID NO: 43).

DETAILED DESCRIPTION OF THE INVENTION

Figure 6:
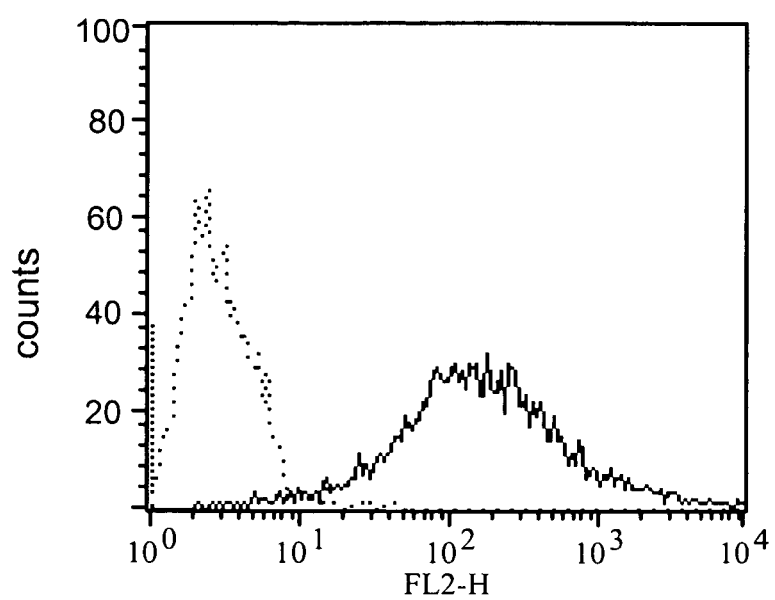
FIG. 6 provides expression level of GM-CSF receptor alpha, as determined by FACS analysis using the GM-CSF receptor alpha specific antibody MAB1006. CHO-GMRa#11 (solid line) is shown in comparison to CHO-K1 (dotted line). The x-axis represents the relative fluorescence value (RFL), measured in FL2 channel; the y-axis represents cell count.

The present invention is based on the discovery of novel antibodies that are specific to or have a high affinity for GM-CSF and possess one or more other novel properties. Preferably, an antibody of the invention can deliver a therapeutic benefit to a subject. The antibodies of the invention, which may be human or humanized, can be used in many contexts, which are more fully described herein.

A "human" antibody or functional human antibody fragment is hereby defined as one that is not chimeric (e.g., not "humanized") and not from (either in whole or in part) a non-human species. A human antibody or functional antibody fragment can be derived from a human or can be a synthetic human antibody. A "synthetic human antibody" is defined herein as an antibody having a sequence derived, in whole or in part, in silico from synthetic sequences that are based on the analysis of known human antibody sequences. In silico design of a human antibody sequence or fragment thereof can be achieved, for example, by analyzing a database of human antibody or antibody fragment sequences and devising a polypeptide sequence utilizing the data obtained therefrom. Another example of a human antibody or functional antibody fragment is one that is encoded by a nucleic acid isolated from a library of antibody sequences of human origin (i.e., such library being based on antibodies taken from a human natural source).

A "humanized antibody" or functional humanized antibody fragment is defined herein as one that is (i) derived from a non-human source (e.g., a transgenic mouse which bears a heterologous immune system), which antibody is based on a human germline sequence; or (ii) chimeric, wherein the variable domain is derived from a non-human origin and the constant domain is derived from a human origin or (iii) CDR-grafted, wherein the CDRs of the variable domain are from a non-human origin, while one or more frameworks of the variable domain are of human origin and the constant domain (if any) is of human origin.

As used herein, an antibody "binds specifically to," is "specific to/for" or "specifically recognizes" an antigen (here, GM-CSF) if such antibody is able to discriminate between such antigen and one or more reference antigen(s), since binding specificity is not an absolute, but a relative property. In its most general form (and when no defined reference is mentioned), "specific binding" is referring to the ability of the antibody to discriminate between the antigen of interest and an unrelated antigen, as determined, for example, in accordance with one of the following methods. Such methods comprise, but are not limited to Western blots, ELISA-, RIA-, ECL-, IRMA-tests and peptide scans. For example, a standard ELISA assay can be carried out. The scoring may be carried out by standard color development (e.g. secondary antibody with horseradish peroxide and tetramethyl benzidine with hydrogenperoxide). The reaction in certain wells is scored by the optical density, for example, at 450 nm. Typical background (=negative reaction) may be 0.1 OD; typical positive reaction may be 1 OD. This means the difference positive/negative can be more than 10-fold. Typically, determination of binding specificity is performed by using not a single reference antigen, but a set of about three to five unrelated antigens, such as milk powder, BSA, transferrin or the like.

However, "specific binding" also may refer to the ability of an antibody to discriminate between the target antigen and one or more closely related antigen(s), which are used as reference points, e.g. between GM-CSF and IL3, IL5, IL-4, IL13 or M-CSF. Additionally, "specific binding" may relate to the ability of an antibody to discriminate between different parts of its target antigen, e.g. different domains or regions of GM-CSF, or between one or more key amino acid residues or stretches of amino acid residues of GM-CSF.

Also, as used herein, an "immunoglobulin" (Ig) hereby is defined as a protein belonging to the class IgG, IgM, IgE, IgA, or IgD (or any subclass thereof), and includes all conventionally known antibodies and functional fragments thereof. A "functional fragment" of an antibody/immunoglobulin hereby is defined as a fragment of an antibody/immunoglobulin (e.g., a variable region of an IgG) that retains the antigen-binding region. An "antigen-binding region" of an antibody typically is found in one or more hypervariable region(s) of an antibody, i.e., the CDR-1, -2, and/or -3 regions; however, the variable "framework" regions can also play an important role in antigen binding, such as by providing a scaffold for the CDRs. Preferably, the "antigen-binding region" comprises at least amino acid residues 4 to 103 of the variable light (VL) chain and 5 to 109 of the variable heavy (VH) chain, more preferably amino acid residues 3 to 107 of VL and 4 to 111 of VH, and particularly preferred are the complete VL and VH chains (amino acid positions 1 to 109 of VL and 1 to 113 of VH; numbering according to WO 97/08320). A preferred class of immunoglobulins for use in the present invention is IgG. "Functional fragments" of the invention include the domain of a F(ab')$_2$ fragment, a Fab fragment, scFv or constructs comprising single immunoglobulin variable domains or single domain antibody polypeptides, e.g. single heavy chain variable domains or single light chain variable domains. The F(ab')$_2$ or Fab may be engineered to minimize or completely remove the intermolecular disulphide interactions that occur between the $C_{H1}$ and $C_L$ domains.

An antibody of the invention may be derived from a recombinant antibody library that is based on amino acid sequences that have been designed in silico and encoded by nucleic acids that are synthetically created. In silico design of an antibody sequence is achieved, for example, by analyzing a database of human sequences and devising a polypeptide sequence utilizing the data obtained therefrom. Methods for designing and obtaining in silico-created sequences are described, for example, in Knappik et al., J. Mol. Biol. (2000) 296:57; Krebs et al., J. Immunol. Methods. (2001) 254:67; and U.S. Pat. No. 6,300,064 issued to Knappik et al., which hereby are incorporated by reference in their entirety.

Antibodies of the Invention

Throughout this document, reference is made to the following representative antibodies of the invention: "antibody nos." or "MOR" 03684, 04251, 03929, 04252, 04287, 04290, 04302, 04350, 04354, 04357, 03682, 04283, 04297 and 04342. MOR03684 represents an antibody having a variable heavy region corresponding to SEQ ID NO: 1

(DNA)/SEQ ID NO: 11 (protein) and a variable light region corresponding to SEQ ID NO: 21 (DNA)/SEQ ID NO: 31 (protein). MOR04251 represents an antibody having a variable heavy region corresponding to SEQ ID NO: 2 (DNA)/SEQ ID NO: 12 (protein) and a variable light region corresponding to SEQ ID NO: 22 (DNA)/SEQ ID NO: 32 (protein). MOR03929 represents an antibody having a variable heavy region corresponding to SEQ ID NO: 3 (DNA)/SEQ ID NO: 13 (protein) and a variable light region corresponding to SEQ ID NO: 23 (DNA)/SEQ ID NO: 33 (protein). MOR04252 represents an antibody having a variable heavy region corresponding to SEQ ID NO: 4 (DNA)/SEQ ID NO: 14 (protein) and a variable light region corresponding to SEQ ID NO: 24 (DNA)/SEQ ID NO: 34 (protein). MOR04287 represents an antibody having a variable heavy region corresponding to SEQ ID NO: 5 (DNA)/SEQ ID NO: 15 (protein) and a variable light region corresponding to SEQ ID NO: 25 (DNA)/SEQ ID NO: 35 (protein). MOR04290 represents an antibody having a variable heavy region corresponding to SEQ ID NO: 6 (DNA)/SEQ ID NO: 16 (protein) and a variable light region corresponding to SEQ ID NO: 26 (DNA)/SEQ ID NO: 36 (protein). MOR04302 represents an antibody having a variable heavy region corresponding to SEQ ID NO: 7 (DNA)/SEQ ID NO: 17 (protein) and a variable light region corresponding to SEQ ID NO: 27 (DNA)/SEQ ID NO: 37 (protein). MOR04350 represents an antibody having a variable heavy region corresponding to SEQ ID NO: 8 (DNA)/SEQ ID NO: 18 (protein) and a variable light region corresponding to SEQ ID NO: 28 (DNA)/SEQ ID NO: 38 (protein). MOR04354 represents an antibody having a variable heavy region corresponding to SEQ ID NO: 9 (DNA)/SEQ ID NO: 19 (protein) and a variable light region corresponding to SEQ ID NO: 29 (DNA)/SEQ ID NO: 39 (protein). MOR04357 represents an antibody having a variable heavy region corresponding to SEQ ID NO: 10 or 48 (DNA)/SEQ ID NO: 20 (protein) and a variable light region corresponding to SEQ ID NO: 30 or 57 (DNA)/SEQ ID NO: 40 (protein). MOR03682 represents an antibody having a variable heavy region corresponding to SEQ ID NO: 44 (DNA)/SEQ ID NO: 49 (protein) and a variable light region corresponding to SEQ ID NO: 53 (DNA)/SEQ ID NO: 58 (protein). MOR04283 represents an antibody having a variable heavy region corresponding to SEQ ID NO: 45 (DNA)/SEQ ID NO: 50 (protein) and a variable light region corresponding to SEQ ID NO: 54 (DNA)/SEQ ID NO: 59 (protein). MOR04297 represents an antibody having a variable heavy region corresponding to SEQ ID NO: 46 (DNA)/SEQ ID NO: 51 (protein) and a variable light region corresponding to SEQ ID NO: 55 (DNA)/SEQ ID NO: 60 (protein). MOR04342 represents an antibody having a variable heavy region corresponding to SEQ ID NO: 47 (DNA)/SEQ ID NO: 52 (protein) and a variable light region corresponding to SEQ ID NO: 56 (DNA)/SEQ ID NO: 61 (protein).

In one aspect, the invention provides antibodies having an antigen-binding region that can bind specifically to or has a high affinity for GM-CSF. An antibody is said to have a "high affinity" for an antigen if the affinity measurement is at least 100 nM (monovalent affinity of Fab fragment). An inventive antibody or antigen-binding region preferably can bind to GM-CSF with an affinity of about less than 100 nM, more preferably less than about 60 nM, and still more preferably less than about 30 nM. Further preferred are antibodies that bind to GM-CSF with an affinity of less than about 10 nM, and more preferably less than about 3 nM. For instance, the affinity of an antibody of the invention against GM-CSF may be about 10.0 nM or 1 pM (monovalent affinity of Fab fragment).

Table 1 provides a summary of affinities of representative antibodies of the invention, as determined by surface plasmon resonance (Biacore) and Solution Equilibrium Titration (SET) analysis:

TABLE 1

Antibody Affinities

| MOR0 | Biacore $K_D$ (pM) | SET $K_D$ (pM) |
|---|---|---|
| 3684 | 6420 | 16000 |
| 4251 | 70 | 7.4 |
| 3929 | 4260 | 2000 |
| 4302 | 174 | 63.5 |
| 4287 | nd | 17.9 |
| 4252 | 55 | 6 |
| 4290 | 122 | 11.1 |
| 4350 | 19 | 1.1 |
| 4354 | 21 | 2.8 |
| 4357 | 7 | 0.4 |
| 3682 | nd | 11406 |
| 4283 | nd | 113 |
| 4297 | nd | 49.2 |
| 4342 | nd | 4.9 |

"nd": not determined

With reference to Table 1, the affinity of MOR03684, 04251, 03929, 04252, 04357, 04290, 04302, 04350 and 04354 was measured by surface plasmon resonance (Biacore) on immobilized recombinant GM-CSF. The Fab format of MOR03684, 04251, 03929, 04252, 04357, 04290, 04302, 04350 and 04354 exhibit a monovalent affinity range between about 6420 and 7 pM.

The Fab format was also used for the determination of the affinities by solution equilibrium titration (SET). The right column of Table 1 denotes the binding strength of between about 16000 and 0.4 pM of the MORs in this method.

An antibody of the invention preferably is species cross-reactive with humans and at least one other species, which may be a rodent species or a non-human primate. The non-human primate can be rhesus. The rodent species can be rat. An antibody that is cross reactive with at least one rodent species, for example, can provide greater flexibility and benefits over known anti-GM-CSF antibodies, for purposes of conducting in vivo studies in multiple species with the same antibody.

Preferably, an antibody of the invention not only is able to bind to GM-CSF, but also is able to block the interaction of human GM-CSF with the alpha chain of human GM-CSF receptor expressed on CHO-K1 cells by at least 25%, preferably by at least 50%, more preferably by at least 60%, more preferably by at least 70%, preferably by at least 85% and most preferably by at least 100%. In a preferred embodiment, an antibody of the invention is able to block interaction of 0.5 µg/ml human GM-CSF with the alpha chain of human GM-CSF receptor expressed on about $2 \times 10^5$ CHO-K1 cells by at least 50% under the following conditions: the concentration of the human GM-CSF receptor alpha chain expressed on the CHO-K1 cells is similar to the concentration of human GM-CSF receptor alpha chain expressed on about $2 \times 10^5$ CHO-GMRa#11 cells, and the concentration of the inventive antibody is about 5 µg/ml.

In this regard, the skilled worker can obtain CHO-K1 cells expressing human GM-CSF receptor alpha at a concentration similar to that which is expressed on about $2 \times 10^5$ CHO-GMRa#11 cells by, e.g., by transfecting a population of CHO-K1 cells with a suitable expression vector encoding GM-CSF receptor alpha to generate different stable cell lines expressing defined levels GM-CSF receptor alpha; then, the stable cell lines are analyzed in FACS analysis to determine GM-CSF receptor alpha expression levels according to the protocol essentially as described in Example 3C; a cell line that expresses human GM-CSF receptor alpha at a concentration similar to that which is expressed on about $2 \times 10^5$ CHO-GMRa#11 cells is identified by comparing the median fluorescence value (MFL) of such transfected cells to the MFL value set forth in Example 3C. As used herein, a cell line is defined as expressing GM-CSF receptor alpha at a concentration "similar" to that which is expressed on about $2 \times 10^5$ CHO-GMRa#11 cells" if the MFL value of the transfected cell line does not deviate by more than a two-fold factor from the MFL value for the CHO-GMRa#11 cell as set forth in Example 3C.

Furthermore, an antibody of the invention is able to neutralize human GM-CSF in a TF-1 proliferation assay with a lower $IC_{50}$ value than the reference antibody BVD2-21C11 and/or MAB215, preferably an at least five-fold lower $IC_{50}$ value, more preferably with an at least 10-fold lower $IC_{50}$ value than the reference antibody BVD2-21C11 and/or MAB215, more preferably with an at least 15-fold lower $IC_{50}$ value than the reference antibody BVD2-21C11 and/or MAB215, more preferably with an at least 20-fold lower $IC_{50}$ value than the reference antibody BVD2-21C11 and/or MAB215, more preferably with an at least 30-fold lower $IC_{50}$ value than the reference antibody BVD2-21C11 and/or MAB215, more preferably with an at least 50-fold lower $IC_{50}$ value than the reference antibody BVD2-21C11 and/or MAB215, more preferably with an at least 100-fold lower $IC_{50}$ value than the reference antibody BVD2-21C11 and/or MAB215 and most preferably with an at least 120-fold lower $IC_{50}$ value than the reference antibody BVD2-21C11 and/or MAB215.

Peptide Variants

Antibodies of the invention are not limited to the specific peptide sequences provided herein. Rather, the invention also embodies variants of these polypeptides. With reference to the instant disclosure and conventionally available technologies and references, the skilled worker will be able to prepare, test and utilize functional variants of the antibodies disclosed herein, while appreciating that variants having the ability to block the interaction of GM-CSF to the alpha chain of the GM-CSF receptor fall within the scope of the present invention. As used in this context, "ability to block the interaction of GM-CSF to the alpha chain of the GM-CSF receptor" means a functional characteristic ascribed to an anti-GM-CSF antibody of the invention.

A variant can include, for example, an antibody that has at least one altered complementarity determining region (CDR) (hyper-variable) and/or framework (FR) (variable) domain/position, vis-à-vis a peptide sequence disclosed herein. To better illustrate this concept, a brief description of antibody structure follows.

An antibody is composed of two peptide chains, each containing one (light chain) or three (heavy chain) constant domains and a variable region (VL, VH), the latter of which is in each case made up of four FR regions and three interspaced CDRs. The antigen-binding site is formed by one or more CDRs, yet the FR regions provide the structural framework for the CDRs and can also play an important role in antigen binding. By altering one or more amino acid residues in a CDR or FR region, the skilled worker routinely can generate mutated or diversified antibody sequences, which can be screened against the antigen, for new or improved properties, for example.

Tables 2a (VH) and 2b (VL) delineate the CDR and FR regions for certain antibodies of the invention and compare amino acids at a given position to each other and to corresponding consensus or "master gene" sequences (as described in U.S. Pat. No. 6,300,064):

TABLE 2a

VH Sequences

| VH | | VH sequences GM-CSF binders | | |
|---|---|---|---|---|
| | | Framework 1 | | CDR 1 |
| Position | | 1 | 2 | 3 |
| | | 1 2 3 4 5 6 7 8 9 0 1 2 3 4 5 6 7 8 9 0 1 2 3 4 5 | 6 7 8 9 0 1 a b 2 3 4 5 |
| | | MfeI | | BspEI |
| SEQ ID NO 41 | VH3 | Q V\|Q L\|V E S G G G L V Q P G G S L R L S C A A\|S | G\|F T F S S - - Y A M S |
| SEQ ID NO 11 | 3684 | Q V\|Q L\|V E S G G G L V Q P G G S L R L S C A A\|S | G\|F T F S S - - H W M S |
| SEQ ID NO 12 | 4251 | Q V\|Q L\|V E S G G G L V Q P G G S L R L S C A A\|S | G\|F T F S S - - H W M S |
| SEQ ID NO 13 | 3929 | Q V\|Q L\|V E S G G G L V Q P G G S L R L S C A A\|S | G\|F T F S S - - Y W M N |
| SEQ ID NO 17 | 4302 | Q V\|Q L\|V E S G G G L V Q P G G S L R L S C A A\|S | G\|F T F S S - - Y W M N |
| SEQ ID NO 16 | 4290 | Q V\|Q L\|V E S G G G L V Q P G G S L R L S C A A\|S | G\|F T F S S - - Y W M N |
| SEQ ID NO 19 | 4354 | Q V\|Q L\|V E S G G G L V Q P G G S L R L S C A A\|S | G\|F T F S S - - Y W M N |
| SEQ ID NO 15 | 4287 | Q V\|Q L\|V E S G G G L V Q P G G S L R L S C A A\|S | G\|F T F S S - - Y W M N |
| SEQ ID NO 18 | 4350 | Q V\|Q L\|V E S G G G L V Q P G G S L R L S C A A\|S | G\|F T F S S - - Y W M N |
| SEQ ID NO 14 | 4252 | Q V\|Q L\|V E S G G G L V Q P G G S L R L S C A A\|S | G\|F T F S S - - Y W M N |
| SEQ ID NO 20 | 4357 | Q V\|Q L\|V E S G G G L V Q P G G S L R L S C A A\|S | G\|F T F S S - - Y W M N |
| SEQ ID NO 62 | VH1A | Q V\|Q L\|V Q S G A E V K K P G S S V K V S C K A\|S | G\|G T F S S - - Y A I S |
| SEQ ID NO 49 | 3682 | Q V\|Q L\|V Q S G A E V K K P G S S V K V S C K A\|S | G\|G T F N S - - F L I S |
| SEQ ID NO 51 | 4297 | Q V\|Q L\|V Q S G A E V K K P G S S V K V S C K A\|S | G\|G T F N S - - F L I S |
| SEQ ID NO 50 | 4283 | Q V\|Q L\|V Q S G A E V K K P G S S V K V S C K A\|S | G\|G T F N S - - F L I S |
| SEQ ID NO 52 | 4342 | Q V\|Q L\|V Q S G A E V K K P G S S V K V S C K A\|S | G\|G T F N S - - F L I S |

TABLE 2a-continued

VH Sequences

| VH | | VH sequences GM-CSF binders | | |
|---|---|---|---|---|
| | | Framework 2 | | CDR 2 |
| Position | | 4 | 5 | 6 |
| | | 6 7 8 9 0 1 2 3 4 5 6 7 8 9 | 0 1 2 a b c 3 4 5 | 6 7 8 9 0 1 2 3 4 5 |
| | | MfeI    BstXI    XhoI | BspEI | |
| SEQ ID NO 41 | VH3 | W V R Q A P G K G L E W V S | A I S G - - S G G S | T Y Y A D S V K G |
| SEQ ID NO 11 | 3684 | W V R Q A P G K G L E W V S | N G I F S - D G S A | T Y Y A D S V K G |
| SEQ ID NO 12 | 4251 | W V R Q A P G K G L E W V S | N I W - - - R G P Y | I Y Y A D S V K G |
| SEQ ID NO 13 | 3929 | W V R Q A P G K G L E W V S | G I S Y - - S G S E | T Y Y A D S V K G |
| SEQ ID NO 17 | 4302 | W V R Q A P G K G L E W V S | G I S Y - - S G S E | T Y Y A D S V K G |
| SEQ ID NO 16 | 4290 | W V R Q A P G K G L E W V S | G I E S K W A G G A | T Y Y A A G V K G |
| SEQ ID NO 19 | 4354 | W V R Q A P G K G L E W V S | G I E S K W A G G A | T Y Y A A G V K G |
| SEQ ID NO 15 | 4287 | W V R Q A P G K G L E W V S | G I E N K R A G G A | T F Y A A S V K G |
| SEQ ID NO 18 | 4350 | W V R Q A P G K G L E W V S | G I E N K R A G G A | T F Y A A S V K G |
| SEQ ID NO 14 | 4252 | W V R Q A P G K G L E W V S | G I E N K Y A G G A | T Y Y A A S V K G |
| SEQ ID NO 20 | 4357 | W V R Q A P G K G L E W V S | G I E N K Y A G G A | T Y Y A A S V K G |
| SEQ ID NO 62 | VH1A | W V R Q A P G Q G L E W M G | G I I P - - I F G T | A N Y A Q K F Q G |
| SEQ ID NO 49 | 3682 | W V R Q A P G Q G L E W M G | G I I P - - I F G T | A N Y A Q K F Q G |
| SEQ ID NO 51 | 4297 | W V R Q A P G Q G L E W M G | G I I P - - I F G T | A N Y A Q K F Q G |
| SEQ ID NO 50 | 4283 | W V R Q A P G Q G L E W M G | A I S P - - W D G V | T G Y A Q K F Q G |
| SEQ ID NO 52 | 4342 | W V R Q A P G Q G L E W M G | A I S P - - W D G V | T G Y A Q K F Q G |

| VH | | VH sequences GM-CSF binders | | |
|---|---|---|---|---|
| | | Framework 3 | | CDR3 |
| Position | | 7 | 8 | 9 |
| | | 6 7 8 9 0 1 2 3 4 5 6 7 8 9 | 0 1 2 a b c 3 4 5 6 7 8 9 | 0 1 2 3 4 5 6 7 8 9 |
| | | | EagI | BssHII |
| SEQ ID NO 41 | VH3 | R F T I S R D N S K N T L Y | L Q M N S L R A E D T A V Y Y C A R | W G G D G |
| SEQ ID NO 11 | 3684 | R F T I S R D N S K N T L Y | L Q M N S L R A E D T A V Y Y C A R | F Q G Y G |
| SEQ ID NO 12 | 4251 | R F T I S R D N S K N T L Y | L Q M N S L R A E D T A V Y Y C A R | F Q G Y G |
| SEQ ID NO 13 | 3929 | R F T I S R D N S K N T L Y | L Q M N S L R A E D T A V Y Y C A R | G F G - - |
| SEQ ID NO 17 | 4302 | R F T I S R D N S K N T L Y | L Q M N S L R A E D T A V Y Y C A R | G F G - - |
| SEQ ID NO 16 | 4290 | R F T I S R D N S K N T L Y | L Q M N S L R A E D T A V Y Y C A R | G F G - - |
| SEQ ID NO 19 | 4354 | R F T I S R D N S K N T L Y | L Q M N S L R A E D T A V Y Y C A R | G F G - - |
| SEQ ID NO 15 | 4287 | R F T I S R D N S K N T L Y | L Q M N S L R A E D T A V Y Y C A R | G F G - - |
| SEQ ID NO 18 | 4350 | R F T I S R D N S K N T L Y | L Q M N S L R A E D T A V Y Y C A R | G F G - - |
| SEQ ID NO 14 | 4252 | R F T I S R D N S K N T L Y | L Q M N S L R A E D T A V Y Y C A R | G F G - - |
| SEQ ID NO 20 | 4257 | R F T I S R D N S K N T L Y | L Q M N S L R A E D T A V Y Y C A R | G F G - - |
| SEQ ID NO 62 | VH1A | R V T I T A D E S T S T A Y | M E L S S L R S E D T A V Y Y C A R | X X X X X |
| SEQ ID NO 49 | 3682 | R V T I T A D E S T S T A Y | M E L S S L R S E D T A V Y Y C A R | K F I - - |
| SEQ ID NO 51 | 4297 | R V T I T A D E S T S T A Y | M E L S S L R S E D T A V Y Y C A R | K F I - - |
| SEQ ID NO 50 | 4283 | R V T I T A D E S T S T A Y | M E L S S L R S E D T A V Y Y C A R | K F I - - |
| SEQ ID NO 52 | 4342 | R V T I T A D E S T S T A Y | M E L S S L R S E D T A V Y Y C A R | K F I - - |

TABLE 2a-continued

VH Sequences

VH sequences GM-CSF binders

|  |  |  | CDR3 | Framework 4 |
|---|---|---|---|---|
| Position | | | 10 ... 11 | |
| | | | 0 a b c d e f g h i j 1 2 3 | 4 5 6 7 8 9 0 1 2 3 |
| | | | StyI | BlpI |
| SEQ ID NO 41 | VH3 | | F Y A - - - - - - - - M D Y W G | Q G T L V T V S S |
| SEQ ID NO 11 | 3684 | | G G - - - - - - - - - F D Y W G | Q G T L V T V S S |
| SEQ ID NO 12 | 4251 | | G G - - - - - - - - - F D Y W G | Q G T L V T V S S |
| SEQ ID NO 13 | 3929 | | - - - - - - - - - - - T D F W G | Q G T L V T V S S |
| SEQ ID NO 17 | 4302 | | - - - - - - - - - - - T D F W G | Q G T L V T V S S |
| SEQ ID NO 16 | 4290 | | - - - - - - - - - - - T D F W G | Q G T L V T V S S |
| SEQ ID NO 19 | 4354 | | - - - - - - - - - - - T D F W G | Q G T L V T V S S |
| SEQ ID NO 15 | 4287 | | - - - - - - - - - - - T D F W G | Q G T L V T V S S |
| SEQ ID NO 18 | 4350 | | - - - - - - - - - - - T D F W G | Q G T L V T V S S |
| SEQ ID NO 14 | 4252 | | - - - - - - - - - - - T D F W G | Q G T L V T V S S |
| SEQ ID NO 20 | 4257 | | - - - - - - - - - - - T D F W G | Q G T L V T V S S |
| SEQ ID NO 62 | VH1A | | X X X X X X X X X X X X W G | Q G T L V T V S S |
| SEQ ID NO 49 | 3682 | | - - - - - - - - - - - S D S W G | Q G T L V T V S S |
| SEQ ID NO 51 | 4297 | | - - - - - - - - - - - S D S W G | Q G T L V T V S S |
| SEQ ID NO 50 | 4283 | | - - - - - - - - - - - S D S W G | Q G T L V T V S S |
| SEQ ID NO 52 | 4342 | | - - - - - - - - - - - S D S W G | Q G T L V T V S S |

TABLE 2b

VL Sequences

VL sequences GM-CSF binders

|  |  | Framework 1 | CDR 1 |
|---|---|---|---|
| Position | | 1 ... 2 | 3 |
| | | 1 2 3 4 5 6 7 8 9 0 1 2 3 4 5 6 7 8 9 0 1 2 3 | 4 5 6 7 8 9 0 a b c d e f 1 |
| | | EcnRV   SexAI   BssSI | |
| SEQ ID NO 42 | VLλ3 | D I E L T Q P P - S V S V A P G Q T A R I S C | S G D A L G D - - - - - - K |
| SEQ ID NO 31 | 3684 | D I E L T Q P P - S V S V A P G Q T A R I S C | S G D N L P G - - - - - - K |
| SEQ ID NO 32 | 4251 | D I E L T Q P P - S V S V A P G Q T A R I S C | S G D N L P G - - - - - - K |
| SEQ ID NO 33 | 3929 | D I E L T Q P P - S V S V A P G Q T A R I S C | S G D S I G K - - - - - - K |
| SEQ ID NO 36 | 4290 | D I E L T Q P P - S V S V A P G Q T A R I S C | S G D S I G K - - - - - - K |
| SEQ ID NO 35 | 4287 | D I E L T Q P P - S V S V A P G Q T A R I S C | S G D S I G K - - - - - - K |
| SEQ ID NO 34 | 4252 | D I E L T Q P P - S V S V A P G Q T A R I S C | S G D S I G K - - - - - - K |
| SEQ ID NO 37 | 4302 | D I E L T Q P P - S V S V A P G Q T A R I S C | S G D S I G K - - - - - - K |
| SEQ ID NO 38 | 4350 | D I E L T Q P P - S V S V A P G Q T A R I S C | S G D S I G K - - - - - - K |
| SEQ ID NO 39 | 4354 | D I E L T Q P P - S V S V A P G Q T A R I S C | S G D S I G K - - - - - - K |
| SEQ ID NO 40 | 4357 | D I E L T Q P P - S V S V A P G Q T A R I S C | S G D S I G K - - - - - - K |
| | | EcoRV   BanI                     PstI | |
| SEQ ID NO 63 | VLκ1 | D I Q M T Q S P S S L S A S V G D R V T I T C | R A S Q G I S - - - - - - S |
| SEQ ID NO 58 | 3682 | D I Q M T Q S P S S L S A S V G D R V T I T C | R A S Q T I N - - - - - - N |
| SEQ ID NO 59 | 4283 | D I Q M T Q S P S S L S A S V G D R V T I T C | R A S Q T I N - - - - - - N |
| SEQ ID NO 60 | 4297 | D I Q M T Q S P S S L S A S V G D R V T I T C | R A S Q T I N - - - - - - N |
| SEQ ID NO 61 | 4342 | D I Q M T Q S P S S L S A S V G D R V T I T C | R A S Q T I N - - - - - - N |

TABLE 2b-continued

VL Sequences

VL sequences GM-CSF binders

| | | | CDR 1 | Framework 2 | | | | | | | | | | | | | CDR 2 | | | | | |
|---|---|---|---|---|---|---|---|---|---|---|---|---|---|---|---|---|---|---|---|---|---|---|
| Position | | | | | | | | 4 | | | | | | | | | 5 | | | | | |
| | | | 2 3 4 | 5 6 7 8 9 | 0 | 1 2 3 | 4 5 | 6 7 8 9 | 0 1 2 3 4 5 6 |
| | | | KpnI | XmaI | BbeI | | | | su36I |
| SEQ ID NO 42 | VLλ3 | Y A S | W Y Q Q K | P G | Q A P | V L V I Y | D D S D R P S |
| SEQ ID NO 31 | 3684 | Y V H | W Y Q Q K | P G | Q A P | V L V I Y | Y D S N R P S |
| SEQ ID NO 32 | 4251 | Y V H | W Y Q Q K | P G | Q A P | V L V I Y | Y D S N R P S |
| SEQ ID NO 33 | 3929 | Y A Y | W Y Q Q K | P G | Q A P | V L V I Y | K K - - R P S |
| SEQ ID NO 36 | 4290 | Y A Y | W Y Q Q K | P G | Q A P | V L V I Y | K K - - R P S |
| SEQ ID NO 35 | 4287 | Y A Y | W Y Q Q K | P G | Q A P | V L V I Y | K K - - R P S |
| SEQ ID NO 34 | 4252 | Y A Y | W Y Q Q K | P G | Q A P | V L V I Y | K K - - R P S |
| SEQ ID NO 37 | 4302 | Y A Y | W Y Q Q K | P G | Q A P | V L V I Y | K K - - R P S |
| SEQ ID NO 38 | 4350 | Y A Y | W Y Q Q K | P G | Q A P | V L V I Y | K K - - R P S |
| SEQ ID NO 39 | 4354 | Y A Y | W Y Q Q K | P G | Q A P | V L V I Y | K K - - R P S |
| SEQ ID NO 40 | 4357 | Y A Y | W Y Q Q K | P G | Q A P | V L V I Y | K K - - R P S |
| | | | KpnI | SexAI | | | | | Ase1 |
| SEQ ID NO 63 | VLκ1 | Y L A | W Y Q Q K | P G | K A P K L | L I Y | A A S S L Q S |
| SEQ ID NO 58 | 3682 | Y L N | W Y Q Q K | P G | K A P K L | L I Y | T A S N L Q S |
| SEQ ID NO 59 | 4283 | Y L N | W Y Q Q K | P G | K A P K L | L I Y | T A S N L Q S |
| SEQ ID NO 60 | 4297 | Y L N | W Y Q Q K | P G | K A P K L | L I Y | T A S N L Q S |
| SEQ ID NO 61 | 4342 | Y L N | W Y Q Q K | P G | K A P K L | L I Y | T A S N L Q S |

VL sequences GM-CSF binders

| | | Framework 3 | | | | | | | | | | | | | | | | | | | | | | | | CDR3 | |
|---|---|---|---|---|---|---|---|---|---|---|---|---|---|---|---|---|---|---|---|---|---|---|---|---|---|---|---|
| Position | | 6 | | | | 7 | | | | 8 | | | | 9 | | | | |
| | | 7 8 9 0 1 2 3 4 5 6 7 8 9 0 1 2 3 4 5 6 7 8 9 0 1 2 3 4 5 6 7 8 9 0 1 2 3 4 5 a b 6 |
| | | BamHI | | | | | | | | | | | | | | | BbsI | | | | | | | | | | |
| SEQ ID NO 42 | VLλ3 | G I P E R F S G S N S G N T A T L T I S G T Q A E D E A D Y Y C Q Q H Y T T P - - P |
| SEQ ID NO 31 | 3684 | G I P E R F S G S N S G N T A T L T I S G T Q A E D E A D Y Y C Q S R T Q T T - - I |
| SEQ ID NO 32 | 4251 | G I P E R F S G S N S G N T A T L T I S G T Q A E D E A D Y Y C Q S R T Q T T - - I |
| SEQ ID NO 33 | 3929 | G I P E R F S G S N S G N T A T L T I S G T Q A E D E A D Y Y C S S W D S T G - - L |
| SEQ ID NO 36 | 4290 | G I P E R F S G S N S G N T A T L T I S G T Q A E D E A D Y Y C S S W D S T G - - L |
| SEQ ID NO 35 | 4287 | G I P E R F S G S N S G N T A T L T I S G T Q A E D E A D Y Y C S S W D S T G - - L |
| SEQ ID NO 34 | 4252 | G I P E R F S G S N S G N T A T L T I S G T Q A E D E A D Y Y C S S W D S T G - - L |
| SEQ ID NO 37 | 4302 | G I P E R F S G S N S G N T A T L T I S G T Q A E D E A D Y Y C S A W G D K G - - M |
| SEQ ID NO 38 | 4350 | G I P E R F S G S N S G N T A T L T I S G T Q A E D E A D Y Y C S A W G D K G - - M |
| SEQ ID NO 39 | 4354 | G I P E R F S G S N S G N T A T L T I S G T Q A E D E A D Y Y C S A W G D K G - - M |
| SEQ ID NO 40 | 4357 | G I P E R F S D S N S G N T A T L T I S G T Q A E D E A D Y Y C S A W G D K G - - M |
| | | SanDI | | BamHI | | | | | | | | | | | | BbsI | | | | | | | | | | |
| SEQ ID NO 63 | VLκ1 | G V P S R F S G S G S G T D F T L T I S S L Q P E D F AT/VY Y C X X X X X X X - - X |
| SEQ ID NO 58 | 3682 | G V P S R F S G S G S G T D F T L T I S S L Q P E D F A V Y Y C Q Q Y S G S P - - M |
| SEQ ID NO 59 | 4283 | G V P S R F S G S G S G T D F T L T I S S L Q P E D F A V Y Y C Q Q Y S G S P - - M |
| SEQ ID NO 60 | 4297 | G V P S R F S G S G S G T D F T L T I S S L Q P E D F A T Y Y C Q Q Y S W V P - - H |
| SEQ ID NO 61 | 4342 | G V P S R F S G S G S G T D F T L T I S S L Q P E D F A T Y Y C Q Q Y S W V P - - H |

TABLE 2b-continued

VL Sequences

|  |  |  | VL | VL sequences GM-CSF binders Framework 4 Position 10 |
|---|---|---|---|---|
|  |  |  |  | 7 8 9 0 1 2 3 4 5 6 7 8 9 |
|  |  |  |  | HpaI · · · · · · MscI |
| SEQ ID NO | 42 | VLλ3 | V F G G G T K\|L T\|V L\|G Q\| |
| SEQ ID NO | 31 | 3684 | V F G G G T K\|L T\|V L\|G Q\| |
| SEQ ID NO | 32 | 4251 | V F G G G T K\|L T\|V L\|G Q\| |
| SEQ ID NO | 33 | 3929 | V F G G G T K\|L T\|V L\|G Q\| |
| SEQ ID NO | 36 | 4302 | V F G G G T K\|L T\|V L\|G Q\| |
| SEQ ID NO | 35 | 4290 | V F G G G T K\|L T\|V L\|G Q\| |
| SEQ ID NO | 34 | 4354 | V F G G G T K\|L T\|V L\|G Q\| |
| SEQ ID NO | 37 | 4287 | V F G G G T K\|L T\|V L\|G Q\| |
| SEQ ID NO | 38 | 4350 | V F G G G T K\|L T\|V L\|G Q\| |
| SEQ ID NO | 39 | 4252 | V F G G G T K\|L T\|V L\|G Q\| |
| SEQ ID NO | 40 | 4257 | V F G G G T K\|L T\|V L\|G Q\| |
|  |  |  |  | MscI · · · · · · BslWI |
| SEQ ID NO | 63 | VLκ1 | T F\|G Q\|G T K V E I K\|R T\| |
| SEQ ID NO | 58 | 3682 | T F\|G Q\|G T K V E I K\|R T\| |
| SEQ ID NO | 59 | 4297 | T F\|G Q\|G T K V E I K\|R T\| |
| SEQ ID NO | 60 | 4283 | T F\|G Q\|G T K V E I K\|R T\| |
| SEQ ID NO | 61 | 4342 | T F\|G Q\|G T K V E I K\|R T\| |

The original HuCAL® master genes have been constructed with their authentic N-termini, e.g. VL lambda 3 contains the amino acids "SY" at position 1 and 2; and VH3 contains the amino acid "E" at position 1. During construction of the HuCAL® Fab libraries, including the HuCAL GOLD® library, the first two amino acids have been changed to "DI" in the VL lambda 3 chain; and the first amino acid has been changed to "Q" in the VH3 chain.

The skilled worker can use the data in Tables 2a and 2b to design peptide variants that are within the scope of the present invention. It is preferred that variants are constructed by changing amino acids within one or more CDR regions; a variant might also have one or more altered framework regions. With reference to a comparison of the novel antibodies to each other, candidate residues that can be changed include e.g. residues 27 or 51 of the variable light and e.g. residues 32 or 56 of the variable heavy chains of MOR04251, since these are positions of variance vis-à-vis each other. Alterations also may be made in the framework regions. For example, a peptide FR domain might be altered where there is a deviation in a residue compared to a germline sequence.

With reference to a comparison of the novel antibodies to the corresponding consensus or "master gene" sequence, candidate residues that can be changed include e.g. residues 27, 50 or 90 of the variable light chain of MOR04251 compared to VLλ3 and e.g. residues 33, 52 or 96 of the variable heavy chain of MOR04251 compared to VH3. Alternatively, the skilled worker could make the same analysis by comparing the amino acid sequences disclosed herein to known sequences of the same class of such antibodies, using, for example, the procedure described by Knappik et al. (2000), and U.S. Pat. No. 6,300,064 issued to Knappik et al. Furthermore, variants may be obtained by using one MOR as starting point for optimization by diversifying one or more amino acid residues in the MOR, preferably amino acid residues in one or more CDRs, and by screening the resulting collection of antibody variants for variants with improved properties. Particularly preferred is diversification of one or more amino acid residues in CDR-3 of VL, CDR-3 of VH, CDR-1 of VL and/or CDR-2 of VH. Diversification can be done by synthesizing a collection of DNA molecules using trinucleotide mutagenesis (TRIM) technology (Virnekäs et al., 1994).

Conservative Amino Acid Variants

Polypeptide variants may be made that conserve the overall molecular structure of an antibody peptide sequence described herein. Given the properties of the individual amino acids, some rational substitutions will be recognized by the skilled worker. Amino acid substitutions, i.e., "conservative substitutions," may be made, for instance, on the basis of similarity in polarity, charge, solubility, hydrophobicity, hydrophilicity, and/or the amphipathic nature of the residues involved.

For example, (a) nonpolar (hydrophobic) amino acids include alanine, leucine, isoleucine, valine, proline, phenylalanine, tryptophan, and methionine; (b) polar neutral amino acids include glycine, serine, threonine, cysteine, tyrosine, asparagine, and glutamine; (c) positively charged (basic) amino acids include arginine, lysine, and histidine; and (d) negatively charged (acidic) amino acids include aspartic acid and glutamic acid. Substitutions typically may be made within groups (a)-(d). In addition, glycine and proline may be substituted for one another based on their ability to disrupt α-helices. Similarly, certain amino acids, such as alanine, cysteine, leucine, methionine, glutamic acid, glutamine, histidine and lysine are more commonly found in α-helices, while valine, isoleucine, phenylalanine, tyrosine, tryptophan and threonine are more commonly found in β-pleated sheets. Glycine, serine, aspartic acid, asparagine, and proline are commonly found in turns. Some preferred substitutions may be made among the following groups: (i) S and T; (ii) P and G; and (iii) A, V, L and I. Given the known genetic code, and recombinant and synthetic DNA techniques, the skilled scientist readily can construct DNAs encoding the conservative amino acid variants.

As used herein, "sequence identity" between two polypeptide sequences, indicates the percentage of amino acids that are identical between the sequences. "Sequence homology", indicates the percentage of amino acids that either are identical or that represent conservative amino acid substitutions. Preferred polypeptide sequences of the invention have a sequence identity in the CDR regions of at least 60%, more preferably, at least 70% or 80%, still more preferably at least 90% and most preferably at least 95%. Preferred antibodies also have a sequence homology in the CDR regions of at least 80%, more preferably 90% and most preferably 95%.

DNA Molecules of the Invention

The present invention also relates to the DNA molecules that encode an antibody of the invention. These sequences include, but are not limited to, those DNA molecules set forth in FIGS. 1a and 2a.

DNA molecules of the invention are not limited to the sequences disclosed herein, but also include variants thereof. DNA variants within the invention may be described by reference to their physical properties in hybridization. The skilled worker will recognize that DNA can be used to identify its complement and, since DNA is double stranded, its equivalent or homolog, using nucleic acid hybridization techniques. It also will be recognized that hybridization can occur with less than 100% complementarity. However, given appropriate choice of conditions, hybridization techniques can be used to differentiate among DNA sequences based on their structural relatedness to a particular probe. For guidance regarding such conditions see, Sambrook et al., 1989 (Sambrook, J., Fritsch, E. F. and Maniatis, T. (1989) Molecular Cloning: A laboratory manual, Cold Spring Harbor Laboratory Press, Cold Spring Harbor, USA) and Ausubel et al., 1995 (Ausubel, F. M., Brent, R., Kingston, R. E., Moore, D. D., Sedman, J. G., Smith, J. A., & Struhl, K. eds. (1995). Current Protocols in Molecular Biology. New York: John Wiley and Sons).

Structural similarity between two polynucleotide sequences can be expressed as a function of "stringency" of the conditions under which the two sequences will hybridize with one another. As used herein, the term "stringency" refers to the extent that the conditions disfavor hybridization. Stringent conditions strongly disfavor hybridization, and only the most structurally related molecules will hybridize to one another under such conditions. Conversely, non-stringent conditions favor hybridization of molecules displaying a lesser degree of structural relatedness. Hybridization stringency, therefore, directly correlates with the structural relationships of two nucleic acid sequences. The following relationships are useful in correlating hybridization and relatedness (where $T_m$ is the melting temperature of a nucleic acid duplex):

a. $T_m = 69.3 + 0.41(G+C)$ %
b. The $T_m$ of a duplex DNA decreases by 1° C. with every increase of 1% in the number of mismatched base pairs.
c. $(T_m)_{\mu 2} - (T_m)_{\mu 1} = 18.5 \log_{10} \mu 2/\mu 1$
where $\mu 1$ and $\mu 2$ are the ionic strengths of two solutions.

Hybridization stringency is a function of many factors, including overall DNA concentration, ionic strength, temperature, probe size and the presence of agents which disrupt hydrogen bonding. Factors promoting hybridization include high DNA concentrations, high ionic strengths, low temperatures, longer probe size and the absence of agents that disrupt hydrogen bonding. Hybridization typically is performed in two phases: the "binding" phase and the "washing" phase.

First, in the binding phase, the probe is bound to the target under conditions favoring hybridization. Stringency is usually controlled at this stage by altering the temperature. For high stringency, the temperature is usually between 65° C. and 70° C., unless short (<20 nt) oligonucleotide probes are used. A representative hybridization solution comprises 6×SSC, 0.5% SDS, 5×Denhardt's solution and 100 µg of nonspecific carrier DNA. See Ausubel et al., section 2.9, supplement 27 (1994). Of course, many different, yet functionally equivalent, buffer conditions are known. Where the degree of relatedness is lower, a lower temperature may be chosen. Low stringency binding temperatures are between about 25° C. and 40° C. Medium stringency is between at least about 40° C. to less than about 65° C. High stringency is at least about 65° C.

Second, the excess probe is removed by washing. It is at this phase that more stringent conditions usually are applied. Hence, it is this "washing" stage that is most important in determining relatedness via hybridization. Washing solutions typically contain lower salt concentrations. One exemplary medium stringency solution contains 2×SSC and 0.1% SDS. A high stringency wash solution contains the equivalent (in ionic strength) of less than about 0.2×SSC, with a preferred stringent solution containing about 0.1×SSC. The temperatures associated with various stringencies are the same as discussed above for "binding." The washing solution also typically is replaced a number of times during washing. For example, typical high stringency washing conditions comprise washing twice for 30 minutes at 55° C. and three times for 15 minutes at 60° C.

Accordingly, the present invention includes nucleic acid molecules that hybridize to the molecules of set forth in FIGS. 1a and 2a under high stringency binding and washing conditions, where such nucleic molecules encode an antibody or functional fragment thereof having properties as described herein. Preferred molecules (from an mRNA perspective) are those that have at least 75% or 80% (preferably at least 85%, more preferably at least 90% and most preferably at least 95%) homology or sequence identity with one of the DNA molecules described herein.

Functionally Equivalent Variants

It is recognized that variants of DNA molecules provided herein can be constructed in several different ways. For example, they may be constructed as completely synthetic DNAs. Methods of efficiently synthesizing oligonucleotides in the range of 20 to about 150 nucleotides are widely available. See Ausubel et al., section 2.11, Supplement 21 (1993). Overlapping oligonucleotides may be synthesized and assembled in a fashion first reported by Khorana et al., J. Mol. Biol. 72:209-217 (1971); see also Ausubel et al., supra, Section 8.2. Synthetic DNAs preferably are designed with convenient restriction sites engineered at the 5' and 3' ends of the gene to facilitate cloning into an appropriate vector.

As indicated, a method of generating variants is to start with one of the DNAs disclosed herein and then to conduct site-directed mutagenesis. See Ausubel et al., supra, chapter 8, Supplement 37 (1997). In a typical method, a target DNA is cloned into a single-stranded DNA bacteriophage vehicle. Single-stranded DNA is isolated and hybridized with an oligonucleotide containing the desired nucleotide alteration(s). The complementary strand is synthesized and the double stranded phage is introduced into a host. Some of the resulting progeny will contain the desired mutant, which can be confirmed using DNA sequencing. In addition, various methods are available that increase the probability that the progeny phage will be the desired mutant. These methods are well known to those in the field and kits are commercially available for generating such mutants.

Recombinant DNA Constructs and Expression

The present invention further provides recombinant DNA constructs comprising one or more of the nucleotide sequences of the present invention. The recombinant constructs of the present invention are used in connection with a vector, such as a plasmid, phagemid, phage or viral vector, into which a DNA molecule encoding an antibody of the invention is inserted.

The encoded gene may be produced by techniques described in Sambrook et al., 1989, and Ausubel et al, 1989. Alternatively, the DNA sequences may be chemically synthesized using, for example, synthesizers. See, for example, the techniques described in OLIGONUCLEOTIDE SYNTHESIS (1984, Gait, ed., IRL Press, Oxford), which is incorporated by reference herein in its entirety. Recombinant constructs of the invention are comprised with expression vectors that are capable of expressing the RNA and/or protein products of the encoded DNA(s). The vector may further comprise regulatory sequences, including a promoter operably linked to the open reading frame (ORF). The vector may further comprise a selectable marker sequence. Specific initiation and bacterial secretory signals also may be required for efficient translation of inserted target gene coding sequences.

The present invention further provides host cells containing at least one of the DNAs of the present invention. The host cell can be virtually any cell for which expression vectors are available. It may be, for example, a higher eukaryotic host cell, such as a mammalian cell, a lower eukaryotic host cell, such as a yeast cell or a prokaryotic cell, such as a bacterial cell. Introduction of the recombinant construct into the host cell can be effected by calcium phosphate transfection, DEAE, dextran mediated transfection, electroporation or phage infection.

Bacterial Expression

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and, if desirable, to provide amplification within the host. Suitable prokaryotic hosts for transformation include *E. coli, Bacillus subtilis, Salmonella typhimurium* and various species within the genera *Pseudomonas, Streptomyces*, and *Staphylococcus*.

Bacterial vectors may be, for example, bacteriophage-, plasmid- or phagemid-based. These vectors can contain a selectable marker and bacterial origin of replication derived from commercially available plasmids typically containing elements of the well known cloning vector pBR322 (ATCC 37017). Following transformation of a suitable host strain and growth of the host strain to an appropriate cell density, the selected promoter is de-repressed/induced by appropriate means (e.g., temperature shift or chemical induction) and cells are cultured for an additional period. Cells are typically harvested by centrifugation, disrupted by physical or chemical means, and the resulting crude extract retained for further purification.

In bacterial systems, a number of expression vectors may be advantageously selected depending upon the use intended for the protein being expressed. For example, when a large quantity of such a protein is to be produced, for the generation of antibodies or to screen peptide libraries, for example, vectors which direct the expression of high levels of fusion protein products that are readily purified may be desirable.

Therapeutic Methods

Therapeutic methods involve administering to a subject in need of treatment a therapeutically effective amount of an antibody contemplated by the invention. A "therapeutically effective" amount hereby is defined as the amount of an antibody that is of sufficient quantity to effectively block the interaction between GM-CSF and its receptor in a treated area of a subject—either as a single dose or according to a multiple dose regimen, alone or in combination with other agents, which leads to the alleviation of an adverse condition, yet which amount is toxicologically tolerable. The subject may be a human or non-human animal (e.g., rat or rhesus).

An antibody of the invention might be co-administered with known medicaments, and in some instances the antibody might itself be modified. For example, an antibody could be conjugated to an immunotoxin or radioisotope to potentially further increase efficacy.

The inventive antibodies can be used as a therapeutic or a diagnostic tool in a variety of situations where GM-CSF is undesirably expressed or found. Disorders and conditions particularly suitable for treatment with an antibody of the inventions are inflammatory diseases such as rheumatoid arthritis (RA), multiple sclerosis, Crohn's disease, psoriasis, asthma, atopic dermatitis or shock.

To treat any of the foregoing disorders, pharmaceutical compositions for use in accordance with the present invention may be formulated in a conventional manner using one or more physiologically acceptable carriers or excipients. An antibody of the invention can be administered by any suitable means, which can vary, depending on the type of disorder being treated. Possible administration routes include parenteral (e.g., intramuscular, intravenous, intraarterial, intraperitoneal, or subcutaneous), intrapulmonary and intranasal, and, if desired for local immunosuppressive treatment, intralesional administration. In addition, an antibody of the invention might be administered by pulse infusion, with, e.g., declining doses of the antibody. Preferably, the dosing is given by injections, most preferably intravenous or subcutaneous injections, depending in part on whether the administration is brief or chronic. The amount to be administered will depend on a variety of factors such as the clinical symptoms, weight of the individual, whether other drugs are administered. The skilled artisan will recognize that the route of administration will vary depending on the disorder or condition to be treated.

Determining a therapeutically effective amount of the novel polypeptide, according to this invention, largely will depend on particular patient characteristics, route of administration, and the nature of the disorder being treated. General guidance can be found, for example, in the publications of the International Conference on Harmonisation and in REMINGTON'S PHARMACEUTICAL SCIENCES, chapters 27 and 28, pp. 484-528 (18th ed., Alfonso R. Gennaro, Ed., Easton, Pa.: Mack Pub. Co., 1990). More specifically, determining a therapeutically effective amount will depend on such factors as toxicity and efficacy of the medicament. Toxicity may be determined using methods well known in the art and found in the foregoing references. Efficacy may be determined utilizing the same guidance in conjunction with the methods described below in the Examples.

Diagnostic Methods

GM-CSF is expressed by various cell types including lymphocytes, monocytes, endothelial cells, fibroblasts and some malignant cells; thus, an anti-GM-CSF antibody of the invention may be employed in order to image or visualize a site of possible accumulation of GM-CSF in different tissues in a patient. In this regard, an antibody can be detectably labeled, through the use of radioisotopes, affinity labels (such as biotin, avidin, etc.) fluorescent labels, paramagnetic atoms, etc. Procedures for accomplishing such labeling are well known to the art. Clinical application of antibodies in diagnostic imaging are reviewed by Grossman, H. B., Urol. Clin. North Amer. 13:465-474 (1986)), Unger, E. C. et al., Invest. Radiol. 20:693-700 (1985)), and Khaw, B. A. et al., Science 209:295-297 (1980)).

The detection of foci of such detectably labeled antibodies might be indicative of a site of inflammation, for example. In one embodiment, this examination is done by removing samples of tissue or blood and incubating such samples in the presence of the detectably labeled antibodies. In a preferred embodiment, this technique is done in a non-invasive manner through the use of magnetic imaging, fluorography, etc. Such a diagnostic test may be employed in monitoring the success of treatment of diseases, where presence or absence of GM-CSF is a relevant indicator. The invention also contemplates the use of an anti-GM-CSF antibody, as described herein for diagnostics in an ex vivo setting.

Therapeutic and Diagnostic Compositions

The antibodies of the present invention can be formulated according to known methods to prepare pharmaceutically useful compositions, wherein an antibody of the invention (including any functional fragment thereof) is combined in a mixture with a pharmaceutically acceptable carrier vehicle. Suitable vehicles and their formulation are described, for example, in REMINGTON'S PHARMACEUTICAL SCIENCES (18th ed., Alfonso R. Gennaro, Ed., Easton, Pa.: Mack Pub. Co., 1990). In order to form a pharmaceutically acceptable composition suitable for effective administration, such compositions will contain an effective amount of one or more of the antibodies of the present invention, together with a suitable amount of carrier vehicle.

Preparations may be suitably formulated to give controlled-release of the active compound. Controlled-release preparations may be achieved through the use of polymers to complex or absorb anti-GM-CSF antibody. The controlled delivery may be exercised by selecting appropriate macromolecules (for example polyesters, polyamino acids, polyvinyl, pyrrolidone, ethylenevinyl-acetate, methylcellulose, carboxymethylcellulose, or protamine, sulfate) and the concentration of macromolecules as well as the methods of incorporation in order to control release. Another possible method to control the duration of action by controlled release preparations is to incorporate anti-GM-CSF antibody into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatine-microcapsules and poly(methylmethacylate) microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

The compounds may be formulated for parenteral administration by injection, e.g., by bolus injection or continuous infusion. Formulations for injection may be presented in unit dosage form, e.g., in ampules, or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compositions may, if desired, be presented in a pack or dispenser device, which may contain one or more unit dosage forms containing the active ingredient. The pack may for example comprise metal or plastic foil, such as a blister pack. The pack or dispenser device may be accompanied by instructions for administration.

The invention further is understood by reference to the following working examples, which are intended to illustrate and, hence, not limit the invention.

EXAMPLES

Example 1

Generation of Human GM-CSF Specific Antibodies from the HuCAL GOLD® Library

A. Phagemid Rescue, Phage Amplification and Purification

HuCAL GOLD® library was amplified in 2×YT medium containing 34 µg/ml chloramphenicol and 1% glucose (2×YT-CG). After helper phage infection (VCSM13) at an $OD_{600}$ of 0.5 (30 min at 37° C. without shaking; 30 min at 37° C. shaking at 250 rpm), cells were spun down (4120 g; 5 min; 4° C.), resuspended in 2×YT/34 µg/ml chloramphenicol/50 µg/ml kanamycin/0.25 mM IPTG and grown overnight at 22° C. Phages were PEG-precipitated from the supernatant, resuspended in PBS/20% glycerol and stored at −80° C. Phage amplification between two panning rounds was conducted as follows: mid-log phase E. coli TG1 cells were infected with eluted phages and plated onto LB-agar supplemented with 1% of glucose and 34 µg/ml of chloramphenicol. After overnight incubation at 30° C., colonies were scraped off and used to inoculate 2×YT-CG until an $OD_{600nm}$ of 0.5 was reached and helper phage added as described above.

B. Pannings with HuCAL GOLD®

For the selection of antibodies recognizing human GM-CSF several panning strategies were applied. In summary, HuCAL GOLD® antibody-phages were divided into three pools comprising different VH master genes. These pools were individually subjected to either a) a solid phase panning on biotinylated human GM-CSF protein (custom made by R&D Systems, Minneapolis, Minn.) directly coated on neutravidin coated 96well plates (Pierce, Rockford, Ill.) as solid support for three rounds or b) a solution panning on biotinylated human GM-CSF protein captured onto streptavidin coated Dynabeads (Dynal, Oslo, Norway) for three rounds.

In detail, for panning on immobilized biotinylated GM-CSF, wells of the neutravidin plate were washed three times with 300 µl PBS. The antigen was diluted to a concentration of 3 µg/ml (200 nM) in PBS and 0.1 ml was coated per well for 2 h at room temperature. After two washing steps with 300 µl PBS the wells were incubated with blocking buffer containing 2× Chemiblocker (Chemicon, Temecula, Calif.) diluted 1:1 in PBS.

Prior to the selections, 100 µl of HuCAL GOLD® phages were pre-adsorbed in 100 µl blocking buffer containing 0.4 µl 25% Tween20 for 0.5 h at RT. Blocked phages were transferred in 100 µl aliquots to wells of a neutravidin plate for 0.5 h at RT. This step was repeated twice for pre-absorption.

After washing (2×300 µl PBS) of the coated and blocked neutravidin microtiter plate, 0.1 ml of the pre-adsorbed phages were added to the coated wells and incubated for 1.5 h at RT shaking gently. This incubation was followed by 10 wash cycles with PBS/0.05% Tween20 at RT.

Bound phages were eluted by adding 120 µl of 20 mM DTT in 10 mM Tris pH 8.0 per well for 10 min at RT. The eluate was removed and added to 14 ml E. coli TG1 grown to an $OD_{600nm}$ of 0.6-0.8. Wells were additionally washed with 200 µl PBS and this solution was also added to the TG1 cells. Phage infection of E. coli was allowed for 45 min at 37° C. without shaking. Additionally, 200 µl of TG1 cells grown to an $OD_{600nm}$ of 0.6-0.8 were added to the selection wells for 45 minutes at 37° C. without shaking. These TG-1 cells were added to the 14 ml culture already containing the phages from the first elution step. After centrifugation for 10 min at 5000 rpm, the bacterial pellets were each resuspended in 500 µl 2×YT medium, plated on 2×YT-CG agar plates and incubated overnight at 30° C. Colonies were then scraped from the plates and phages were rescued and amplified as described above.

The second and third rounds of selection were performed in an identical way to the first round of selection with the only difference that the washing conditions after binding of phage were more stringent. Additionally, in the third round of selection, phages were submitted to an additional preadsorption step on streptavidin-coated beads (Dynabeads M-280; Dynal). Eppendorf tubes were blocked with Chemiblocker solution by incubation for 30 min at RT. Of each phage pool 0.3 ml were mixed 1:1 with 2× Chemiblocker solution containing 0.05% Tween20 and incubated for 1 h at RT in the blocked Eppendorf tubes on a rotator. Blocked phages were then transferred to newly blocked Eppendorf tubes and 50 µl of Dynabeads M-280 were added for another 30 min for preadsorption. Beads were removed using a magnetic device (Dynal MPC-E). Aliquots of 150 µl of phages were then transferred to neutravidin plates for further preadsorption as in round 1 and 2 (see above).

For the solution panning using biotinylated GM-CSF coupled to Dynabeads the following protocol was applied: 1.5 ml Eppendorf tubes were blocked with 1.5 ml 2× Chemiblocker diluted 1:1 with PBS over night at 4° C. 200 µl streptavidin coated magnetic beads (Dynabeads M-280; Dynal) were washed 1× with 200 µl PBS and resuspended in 200 µl 1× Chemiblocker (diluted in 1×PBS). Blocking of beads was performed in preblocked tubes over night at 4° C. Phages diluted in 500 µl PBS for each panning condition were mixed with 500 µl 2× Chemiblocker/0.1% Tween 1 h at RT (rotator). Preadsorption of phages was performed twice: 50 µl of blocked Streptavidin magnetic beads were added to the blocked phages and incubated for 30 min at RT on a rotator. After separation of beads via a magnetic device (Dynal MPC-E) the phage supernatant (~1 ml) was transferred to a new blocked tube and preadsorption was repeated on 50 µl blocked beads for 30 min. Then, 200 nM biotinylated hGM-CSF was added to blocked phages in a new blocked 1.5 ml tube and incubated for 1 h at RT on a rotator. 100 µl of blocked streptavidin magnetic beads were added to each panning phage pool and incubated 10 min at RT on a rotator. Phage bound to biotinylated GM-CSF and therefore immobilized to the magnetic beads were collected with a magnetic particle separator (Dynal MPC-E). Beads were then washed 7× in PBS/0.05% Tween using a rotator, followed by washing another three times with PBS. Elution of phage from the Dynabeads was performed adding 300 µl 20 mM DTT in 10 mM Tris/HCl pH8 to each tube for 10 min. Dynabeads were removed by the magnetic particle separator and the supernatant was added to 14 ml of a E. coli TG-1 culture grown to $OD_{600nm}$ of 0.6-0.8. Beads were then washed once with 200 µl PBS and PBS containing additional removed phage was added to the 14 ml E. coli TG-1 culture.

After centrifugation for 10 min at 5000 rpm, the bacterial pellets were each resuspended in 500 µl 2×YT medium, plated on 2×YT-CG agar plates and incubated overnight at 30° C. Colonies were then scraped from the plates and phages were rescued and amplified as described above.

The second and third rounds of the solution panning on biotinylated GM-CSF was performed according to the protocol of the first round except for increasing the stringency of the washing procedure.

C. Subcloning of Selected Fab Fragments and Expression of Soluble Fab Fragments

The Fab encoding inserts of the selected HuCAL GOLD® phagemids were subcloned into the expression vector pMORPH® X9_Fab_FH (FIG. 5) to facilitate rapid expression of soluble Fab. The DNA of the selected clones was digested with XbaI and EcoRI, thereby cutting out the Fab encoding insert (ompA-VLCL and phoA-Fd), and cloned into the XbaI/EcoRI digested vector pMORPH® X9_Fab_FH. Fabs expressed in these vectors carry two C-terminal tags (FLAG™ and 6×His, respectively) for detection and purification.

D. Microexpression of HuCAL GOLD® Fab Antibodies in E. coli

Single colonies obtained after subcloning into pMORPH® X9_Fab_FH were used to inoculate wells of a sterile 96-well microtiter plate containing 100 µl 2×TY/Cm/ 1% Glu medium per well and grown overnight at 37° C. 5 µl of each TG-1 E. coli culture was transferred to a new sterile 96-well microtiter plate containing 100 µl 2×TY/Cm/ 0.1% Glu medium per well. Microtiter plates were incubated at 30° C. shaking at 400 rpm on a microplate shaker until the cultures were slightly turbid (~2-4 hrs) with an $OD_{600nm}$ of 0.5.

To these expression plates, 20 µl 2×YT/Cm/3 mM IPTG were added per well (end concentration 0.5 mM IPTG), sealed with a gas-permeable tape and incubated overnight at 30° C. shaking at 400 rpm.

Generation of Whole Cell Lysates (BEL Extracts)

To each well of the expression plates, 40 µl BEL buffer (2×BBS/EDTA: 24.7 g/l boric acid, 18.7 g NaCl/l, 1.49 g EDTA/l, pH8) was added containing 2.5 mg/ml lysozyme and incubated for 1 h at 22° C. on a microtiter plate shaker (400 rpm). BEL extracts were used for binding analysis by ELISA or a BioVeris M-Series® 384 analyzer (see Example 2).

E. Expression of HuCAL® Gold Fab Antibodies in E. coli and Purification

Expression of Fab fragments encoded by pMORPH® X9_Fab_FH in TG-1 cells was carried out in shaker flask cultures with 1 l of 2×YT medium supplemented with 34 µg/ml chloramphenicol. After induction with 0.5 mM IPTG, cells were grown at 22° C. for 16 h. Whole cell extracts of cell pellets were prepared by French Press and Fab fragments isolated by nickel/NTA chromatography (Qiagen, Hilden, Germany). Concentrations were determined by UV-spectrophotometry (Krebs et al., 2001).

Example 2

Identification of hGM-CSF Specific Antibodies

BEL extracts of individual *E. coli* clones selected by the above mentioned panning strategies were analyzed by ELISA or BioVeris (BioVeris M-Series® 384 analyzer) in order to identify clones encoding hGM-CSF specific Fabs.

A. Enzyme Linked Immunosorbent Assay (ELISA) Techniques

Human recombinant biotinylated GM-CSF (R&D Systems) was coated at 1.5 µg/ml in PBS onto Neutravidin microtiter plates for 2 h at RT.

After coating of antigen the wells were blocked with PBS/0.05% Tween (PBS-T) with 1% BSA for 1 h at RT. After washing of the wells with PBS-T BEL-extract, purified HuCAL® Fab or control IgGs were diluted in PBS, added to the wells and incubated for 1 h at RT. For detection of the primary antibodies, the following secondary antibodies were applied: alkaline phospatase (AP)-conjugated AffiniPure F(ab')$_2$ fragment, goat anti-human, -anti-mouse or -anti-rat IgG (Jackson Immuno Research). For the detection of AP-conjugates fluorogenic substrates like AttoPhos (Roche) were used according to the instructions by the manufacturer. Between all incubation steps, the wells of the microtiter plate were washed with PBS-T three times and three times after the final incubation with secondary antibody. Fluorescence was measured in a TECAN Spectrafluor plate reader.

B. Electrochemiluminescene (BioVeris) Based Binding Analysis for Detection of GM-CSF Binding Fab in Lysates Alternative to the ELISA experiments for the detection of GM-CSF binding Fab antibodies in *E. coli* lysates (BEL extracts), binding was analyzed in BioVeris M-SERIES® 384 AnalyzerBioVeris, Europe, Witney, Oxforfshire, UK).

To this end BEL extract was diluted at least 1:50 and maximally 1:1000 in assay buffer (PBS/0.05% Tween20/ 0.5% BSA) for use in BioVeris screening. Biotinylated GM-CSF (R&D Systems) was coupled to streptavidin coated paramagnetic beads, Dynabeads (Dynal), at a concentration of 0.1 µg/ml. Per well of a 96 or 384 well plate 25 or 15 µl of a 1:25 dilution of the Dynabead-stock solution was used. Beads were washed three times with assay buffer before adding biotinylated GM-CSF for 30 min at RT on a shaker. Beads were then washed three times with assay buffer and finally resuspended in fresh assay buffer. Anti-human (Fab)'$_2$ (Dianova) was ruthenium labelled using the BV-Tag™ (BioVeris Europe, Witney, Oxfordshire, UK). This secondary antibody was added to the GM-CSF coupled beads at a concentration of 6 µg/ml immediately before use. 100 µl or 60 µl of diluted BEL extract (see above) of *E. coli* expression cultures containing Fab antibodies was filled into wells of a 96 or 384 well plate and, respectively, 25 or 15 µl of the GM-CSF coupled beads plus anti-Fab-BV-Tag™ secondary antibody mix was added to each well and incubated for 2 h at RT on a plate shaking device. The plates were analyzed in a BioVeris M-SERIES® 384 Analyzer.

After sequence analysis seventy-four (74) unique clones were identified that showed sufficiently strong binding (signal:noise ratio greater than 10:1 in ELISA or 50:1 in BioVeris). These clones were expressed, purified and were tested in functional assays.

C. Determination of the Molecular Specificity and Species Crossreactivity of Selected Anti-hGM-CSF Fabs.

Crossreactivity of the anti-hGM-CSF antibodies was determined to the following analytes: rat and mouse GM-CSF, human IL-3, human IL-4, human IL-5, human IL-13, human M-CSF (all from Peprotech, London, UK). This was performed in a capture set-up by surface plasmon resonance (Biacore 3000, Uppsala, Sweden). CM5 chips (Biacore, Sweden) were coated with 5000-6000RU anti-F(ab)$_2$ (Dianova, Affinipure F(ab)$_2$ Fragment Goat Anti-Human IgG, F(ab)$_2$ Fragment specific); 80 µg/ml 10 mM acetate buffer, pH4 on all 4 flow cells, using standard EDC-NHS amine coupling chemistry. On the flow cells 2-4 specific GM-CSF Fabs (20 µl of 500 nM Fab at a flowrate of 5 µl/ml, 300-400RU) were captured. After capturing of the specific Fab, buffer was injected, to determine the dissociation of anti-Fab/Fab interaction. In a following cycle, the analyte growth factor was injected (20 µl, flow rate 20 µl/min) at a concentration range between 15 and 2000 nM for the determination of the specific signal. Afterwards the achieved buffer sensogram was manually subtracted from the specific one. After each cycle, the flow cells were regenerated with 100 mM HCl (5 µl). Seven HuCAL® anti-hGM-CSF antibodies including MOR03684 and MOR03682 were tested and were specific for human GM-CSF and did not bind to any of the other cytokines or mouse or rat GM-CSF. In contrast Fab MOR03929 showed significant cross reactivity to rat GM-CSF.

Example 3

Identification of Anti-Human GM-CSF Fab Candidates that Inhibit the Interaction Between GM-CSF and the GM-CSF Receptor Alpha 74 different hGM-CSF specific antibodies which were selected from the HuCAL GOLD® library were tested for the potency to inhibit the interaction between hGM-CSF and its receptor. The interaction was tested in two ways, (i) one being a proliferation assay using the GM-CSF dependent TF-1 cell line (Kitamura et al., 1989) and (ii) the other being a FACS analysis with a recombinant CHO cell line expressing the alpha chain of the GM-CSF receptor. In the TF-1 proliferation assay, the ability of the anti-GM-CSF antibodies to block the interaction of GM-CSF with the endogenous GM-CSF receptor consisting of the alpha and beta chain was analyzed leading to reduction in cell proliferation. In the FACS assay the specific inhibition of the interaction between GM-CSF and the alpha chain of the GM-CSF receptor was determined.

A. Cloning and Expression of Macaca Mulatta and Human GM-CSF

Macaca mulatta GM-CSF full-length cDNA (GenBank accession no.: AY007376) was synthesized by gene synthesis (geneART GmbH, Regensburg, Germany) and cloned into the pCR-Script-Amp vector (Stratagene, LaJolla, Calif., USA). Subsequently the cDNA was cloned into the eukaryotic expression vector pcDNA3.1 (+) (Invitrogen, Paisley, UK) yielding pcDNA-macGM-CSF. The cDNA of human GM-CSF (Genbank accession number NP_000749) was cloned by RT-PCR technique from RNA isolated from 1×10e7 TF-1 cells using the RNeasy kit from Qiagen (Hilden, Germany). Reverse transcription was performed with the SuperscriptII kit using random hexamers (Gibco) followed amplification of the GM-CSF cDNA by PCR. The obtained PCR-product was cloned into expression vector pcDNA3.1(+) yielding pcDNA-huGM-CSF.

HEK293 cells were transiently transfected with these expression vectors respectively using lipofectamine (Stratagene, LaJolla, USA). The medium containing the secreted recombinant macaca or human GM-CSF was harvested 4 days after transfection.

B. Inhibition of GM-CSF Dependent Proliferation of TF-1 Cells by Anti-hGM-CSF Fabs Using Human or Macaca GM-CSF TF-1 (Kitamura et al., 1989) cells were grown according to the provider's protocol (DSMZ, Braunschweig, Germany; DSMZ No. ACC 334). TF-1 cells were washed twice with RPMI1640 medium (10% FCS) and then seeded at a concentration of $2\times10^5$ cells/ml in 50 µl per well of a flat bottom 96well cell culture dish. Human recombinant GM-CSF ("Leucomax", ESSEX Pharma, München) at 0.5 ng/ml and HuCAL® Fab antibodies (200 ng/ml-200 µg/ml diluted in RPMI1640 medium, 10% FCS) were mixed for 30 min and 50 µl of the mix was added to the TF-1 cells, so that the final concentration of GM-CSF was 0.25 ng/ml. Maximal cell proliferation (0% inhibition) was measured incubating TF-1 cells at a final GM-CSF of concentration of 0.25 ng/ml, without the addition of antibody. 100% inhibition of TF-1 proliferation was measured by omitting GM-CSF from the assay and keeping the cells in RPMI1640 medium (10% FCS) only. TF1 cells were then incubated for 72 hours at 37° C. with 5% $CO_2$ in a humidified chamber. Cell vitality was measured by adding MTT or XTT reagent (Roche, Mannheim, Germany) according to the manufacturer's recommendation. Overall 19 Fab were identified that showed significant inhibition of TF-1 proliferation. The binders MOR03682, MOR03684 and MOR03929 showed consistent inhibition of TF1 cell proliferation of greater than 50% at a concentration of 2 µM. The inhibitory activity of these non-optimized Fabs was not strong enough to determine an $IC_{50}$ dose, because full inhibition could not be achieved. In comparison, monoclonal antibodies BVD2-21C11 (BD Biosciences Pharmingen; Cat#554503) and MAB215 (R&D Systems; Cat#MAB215) were able to fully inhibit TF-1 proliferation.

Additionally, binding of MOR03682 and MOR03684 to native human GM-CSF was tested in the TF-1 proliferation assay. Instead of adding purified human recombinant GM-CSF to the TF-1 cells a supernatant of 5637 cells (DSMZ No. ACC 35) that secrete native human GM-CSF into the medium was used. From a dose response curve comparing the effect of recombinant human GM-CSF with different dilutions of the 5637 supernatant it was determined that the medium contained ~5 ng/ml of native human GM-CSF. By preincubation of the 5637 supernatant with anti-human GM-CSF Fab MOR03682 or MOR03684 the binding of native human GM-CSF to the TF-1 cells was blocked so that the viability of cells was reduced comparably to the experiment with recombinant human GM-CSF. MOR03684 and MOR03682 thus binds to native human GM-CSF. Fab MOR03929 was not tested in this assay.

Additionally, the cross reactivity to macaca GM-CSF was tested in the TF-1 proliferation assay. Instead of adding purified human GM-CSF to the TF-1 cells a supernatant of transfected HEK293 cells that secrete recombinant macaca GM-CSF into the medium was used.

TF-1 cells proliferated in the presence of macaca GM-CSF containing supernatant but not in the presence of supernatant from untransfected HEK293 cells. From a dose response curve comparing the effect of recombinant human GM-CSF with different dilutions of the HEK-293 medium it was determined that the medium of the transfected cells contained ~2 µg/ml macaca GM-CSF. By preincubation of the macaca GM-CSF supernatant with anti-human GM-CSF Fab MOR03682 or MOR03684 the binding of macaca GM-CSF to the TF-1 cells was blocked so that the viability of cells was significantly reduced. MOR03682 and MOR03684_thus are cross-reactive with macaca GM-CSF. Fab MOR03929 was not tested in this assay.

C. Blocking of GM-CSF Binding to the GM-CSF Receptor Alpha by Anti-hGM-CSF Fabs

In order to test binding of GM-CSF to a cell surface expressed GM-CSF receptor alpha chain the cDNA was cloned into an expression vector and stably transfected into CHO-K1 cells (DSMZ ACC 110).

Cloning of a Stable CHO-K1 Cell Line Expressing the Alpha Chain of the GM-CSF Receptor The cDNA of the human GM-CSF receptor alpha chain (Genbank accession number M64445) was cloned by RT-PCR technique from RNA isolated from 1×10e7 TF-1 cells using the RNeasy kit from Qiagen (Hilden, Germany). Reverse transcription was performed with the SuperscriptII kit using random hexamers (Gibco). The GM-CSF-receptor alpha chain cDNA was then amplified using the following primers:

```
5': N-GCRa-plusSS:
                                   (SEQ ID NO: 64)
TTCTCTGGATCCGCCACCATGCTTCTCCTGGTGACAAGCC
and 3': C-flGCRa:
                                   (SEQ ID NO: 65)
ACCCTCCAATTGTCAGGTAATTTCCTTCACGGTC.
```

The PCR reaction yielded a product of ~1250 bp which was digested with EcoRI and BamHI (New England Biolabs). The expression vector pcDNA3.1(+) (Invitrogen, Paisley, UK) was digested with the same enzymes. After purification of the digested vector and PCR product, the fragments were ligated and transformed by electroporation into E. coli DH10B cells. Correct clones were identified after preparation of plasmid DNA and sequencing. Correct clones (pcDNA3.1(+)-GM-CSFRalpha) contained the full length human GM-CSF receptor alpha cDNA.

CHO-K1 cells were grown according to the provider's protocol (DSZM, Braunschweig, Germany; DSMZ No. ACC 110). For transfection cells were grown to 80% confluence in a 6-well plate and incubated with 5 µg DNA of pcDNA3.1(+)-GM-CSFRalpha mixed with 10 µl of the Lipofectamine 2000 reagent (Invitrogen). After 48 h cells were fed with 1 mg/ml G418 (Gibco) and after another 24 h medium was replaced with such containing 2 mg/ml G418. After two weeks single cells were seeded into wells of a 96-well culture dish. Single clones were grown up and $5\times10^5$ cells of each clone were tested for GM-CSFR-alpha expression by FACS analysis using murine IgG MAB1006 (Chemicon International, Temecula, Calif.) as primary antibody at a concentration of 1 µg/ml and (R-PE-AffiniPure (Fab')$_2$ Goat-anti-mouse-IgG (Dianova) as secondary antibody at a 1:200 dilution. Primary and secondary antibodies were incubated with the cells for 1 h sequentially, while cells were washed in FACS buffer (PBS, 3% FCS) between these steps. Fluorescence of stained cells was quantified in the FL2 channel using a FACSCalibur system (Becton Dickinson). Among the clones analyzed clone CHO-GMRa#11 showed the highest median fluorescent intensity. A median fluorescence value (MFL value) of 157 was determined for CHO-GMRa#11 (FIG. 6)

FACS Analysis of GM-CSF Binding to the GM-CSF Receptor Alpha Expressed on CHO-GMRa#11:

Prior to adding to cells, antibodies at increasing concentrations (0.1 to 100 μg/ml) were co-incubated with biotinylated GM-CSF (0.5 μg/ml) in FACS buffer (PBS/3% FBS/NaN$_3$0.05%) for 30 min at RT.

All stainings were performed in round bottom 96-well culture plates (Nalge Nunc) with 1-5×10$^5$ cells per well. 2×10E5 CHO-GMRa#11 cells were taken up in 50 μl of the antibody/GM-CSF containing FACS buffer and incubated at 4° C. for 1 h. Cells were then washed once with 150 μl FACS buffer/well and taken up in 100 μl phycoerythrin-labeled streptavidin (BD Biosciences Pharmingen) which has been diluted 1:400 in FACS buffer. After 1 h incubation at 4° C. cells were washed twice with FACS buffer, resuspended in 100 μl of FACS buffer and binding of biotinylated GM-CSF was measured via FL2 fluorescence intensity of cells in FACScalibur (Becton Dickinson). IC$_{50}$ values were determined from the dose response curves obtained using Graph-Pad Prism v3.03 software applying a non-linear regression curve fit.

Fab antibodies MOR03682, MOR03684 and MOR03929 showed significant inhibition of GM-CSF binding to the cell surface expressed GM-CSF receptor alpha.

Example 4

Affinity Maturation of Selected Fab by Stepwise Exchange of CDR Cassettes

A. Generation of Affinity Maturation Fab Libraries and Pannings

In order to increase the affinity and inhibitory activity of the anti-GM-CSF Fab fragments clones MOR03682, MOR03684 and MOR03929 were subjected to affinity maturation. In this regard, CDR regions were optimized by cassette mutagenesis using trinucleotide directed mutagenesis (Virnekäs et al., 1994; Nagy et al., 2002). Sequence analysis revealed no sequence homology between the CDRs of the three parental clones analyzed. Table 2a and 2b provide the six CDR peptide sequences for the parental clones MOR03682, MOR03684 and MOR03929.

The following briefly describes the protocol used for Fab optimization. Fab fragments from expression vector pMORPH® X9Fab_FH were cloned into a phagemid vector (U.S. Pat. No. 6,753,136). Then, two different strategies were applied to optimize the affinity and efficacy of the parental Fabs.

First, one phage antibody Fab library was generated where the L-CDR3 of each parental was replaced by a repertoire of individual lambda light chain CDR3 sequences. In a second library the H-CDR2 region was replaced by a repertoire of individual heavy chain CDR2 sequences.

Affinity maturation libraries were generated by transforming the diversified clones into E. coli TOP10F' (Invitrogen). Phages were prepared as described in Example 1A. Both L-CDR3 libraries of MOR03684 and MOR03682 were pooled and both H-CDR2 libraries derived from MOR03684 and MOR03682 were pooled, while the L-CDR3 and H-CDR2 libraries derived from MOR03929 were kept separately during the selection procedure.

Pannings were performed on biotinylated GM-CSF in solution for three rounds essentially as described in Example 1B and applying more stringent selection conditions.

B. Electrochemiluminescene (BioVeris) Based Binding Analysis for Detection of Improved GM-CSF Binding Fab in Lysates For the detection of GM-CSF binding Fab antibodies in E. coli lysates (BEL extracts), binding was analyzed in the BioVeris M-384 SERIES® Workstation (BioVeris Europe, Witney, Oxforshire, UK) essentially as described in Example 2B.

Fabs with the highest ECL values were purified and subjected to affinity measurement by solution equilibrium titration (SET; Haenel et al, 2005) and surface plasmon resonance (Biacore) (see Example 4D)

C. X-Cloning of Improved VL (L-CDR3) with Improved VH (H-CDR2)

For a further improvement of affinity the independently optimized H-CDR2 and L-CDR3 from matured Fabs which were derived from the same parental clone were combined, because there was a high probability that this combination would lead to a further gain of affinity (Yang et al., 1995; Schier et al., 1996; Chen et al., 1999). This procedure, called X-cloning, was applied for binders that were derived from the parental clone MOR03929 as Fabs with improved affinities were identified from both the H-CDR2 and the L-CDR3 library. This was accomplished by transferring whole light chains (XbaI/SphI fragment) from the L-CDR3-optimized donor clone to the H-CDR2-optimized acceptor clone.

TABLE 3

| X-cloning combinations | | | | |
|---|---|---|---|---|
| Parental | VH donor | | VL donor | Affinity Improved Fab after X-cloning |
| MOR03929 | MOR04287 | x | MOR04302 | MOR04350 |
| | MOR04290 | | | MOR04354 |
| | MOR04252 | | | MOR04357 |
| MOR03682 | MOR04283 | x | MOR04297 | MOR04342 |

For the resulting 4 Fabs the VL and VH was sequenced to confirm transfer of the correct VL to the respective H-CDR2 improved vector backbone. Table 2a and 2b show the VH and VL protein sequences of all derivatives of MOR03929 and 3682, which are listed in table 3.

D. Determination of Picomolar Affinities Using Solution Equilibrium Titration (SET) and Surface Plasmon Resonance (Biacore)

For $K_D$ determination, monomer fractions (at least 90% monomer content, analyzed by analytical SEC; Superdex75, Amersham Pharmacia) of Fab were used. Electrochemiluminescence (ECL) based affinity determination in solution and data evaluation were basically performed as described by Haenel et al., 2005: A constant amount of Fab was equilibrated with different concentrations (serial 5" dilutions) of human GM-CSF (Leucomax) in solution. Biotinylated human GM-CSF (R&D Systems) coupled to paramagnetic beads (M-280 Streptavidin, Dynal) and BV-Tag™ (BioVeris Europe, Witney, Oxforshire, UK) labeled anti-human (Fab)'$_2$ (Dianova) was added and incubated for 15-30 min. Subsequently, the concentration of unbound Fab was quantified via ECL detection using a M-SERIES® 384 analyzer (BioVeris Europe).

In accordance with Friguet et al., 1985, care was taken to avoid significant equilibrium shift to solid phase during detection.

Using the assay conditions described above affinities for the Fabs were determined, which are shown in table 4.

Additionally kinetic SPR analysis was performed on an F1 chip (Biacore, Sweden) which was coated with a density of ~100 RU recombinant human GM-CSF (Peprotech) in 10 mM Na-acetate pH 4.5 using standard EDC-NHS amine coupling chemistry. A respective amount of HSA was immobilized on the reference flow cell. PBS (136 mM NaCl, 2.7 mM KCl, 10 mM $Na_2HPO_4$, 1.76 mM $KH_2PO_4$ pH 7.4)+ 0.005% Tween 20 was used as running buffer. Fab was applied in concentration series of 6.3-200 nM at a flow rate of 20 µl/min. Association phase was set to 60 s and dissociation phase to 120 s (parental) or up to 600 s (affinity optimized). In order to monitor dissociation phase over a longer period, the following conditions, basically according to Drake et al., (2004) were used: Fab was applied in a single concentration of 200 nM; flow rate was set to 100 µl/min and dissociation phase to 6000-18.000 s. On the basis of the off-rates determined under these assay conditions affinities for the Fabs were estimated, which are shown in table 4.

TABLE 4

Affinities of anti-hGM-CSF Fabs determined by Biacore and solution equilibrium titration (SET)

| MOR0 | Biacore $K_D$ (pM) | SET $K_D$ (pM) |
|---|---|---|
| 3684 | 6420 | 16000 |
| 4251 | 70 | 7.4 |
| 3929 | 4260 | 2000 |
| 4302 | 174 | 63.5 |
| 4287 | nd | 17.9 |
| 4252 | 55 | 6 |
| 4290 | 122 | 11.1 |
| 4350 | 19 | 1.1 |
| 4354 | 21 | 2.8 |
| 4357 | 7 | 0.4 |
| 3682 | nd | 11406 |
| 4283 | nd | 113 |

TABLE 4-continued

Affinities of anti-hGM-CSF Fabs determined by Biacore and solution equilibrium titration (SET)

| MOR0 | Biacore $K_D$ (pM) | SET $K_D$ (pM) |
|---|---|---|
| 4297 | nd | 49.2 |
| 4342 | nd | 4.9 |

E. Determination of Affinities to Rat GM-CSF Using Solution Equilibrium Titration (SET)

Affinity determination to rat GM-CSF was done essentially as described in Example 4D using rat-GM-CSF (Peprotech) as analyte in solution instead of human GM-CSF. Affinities were calculated according to Haenel et al (2005). In this assay affinity of Fab MOR04357 to rat GM-CSF was determined to be $K_D$=1.0 nM.

Example 5

Characterization of Optimized Anti-Human GM-CSF Fabs that Inhibit the Interaction Between GM-CSF and the GM-CSF Receptor Alpha Chain A. GM-CSF Receptor Alpha Binding Assay The GM-CSF receptor binding assay was performed as described above (Example 3C) using 0.5 µg/ml (35 nM) of biotinylated GM-CSF. Maximal binding of GM-CSF to CHO-GMRa#11 cells (0% inhibition) was measured by incubating cells at a final GM-CSF concentration of 0.5 µg/ml of biotinylated GM-CSF, without the addition of antibody. 100% inhibition of GM-CSF binding was measured by omitting GM-CSF from the assay. $IC_{50}$ values were determined from the dose response curves obtained using GraphPad Prism v3.03 software applying a non-linear regression curve fit. Fabs with improved affinities, the parental Fabs and monoclonal reference IgGs were analyzed. Table 5 summarizes the IC50 values obtained in these assays. The inhibition achieved at an antibody concentration of 5 µg/ml is also given in table 5.

TABLE 5

$IC_{50}$ values of anti-hGM-CSF Fabs in receptor inhibition assay

| | MOR0# | | | | | | | | | | |
|---|---|---|---|---|---|---|---|---|---|---|---|
| | 4251 | 4357 | 4354 | 4350 | 4252 | 4287 | 4290 | 4302 | 3684 | 3929 | Mab21521C11 |
| $IC_{50}$ (nM) | 53 | 26 | 26 | 24 | 26 | 25 | 27 | 24 | >400 | 35 | no fit* | 9 |
| % inhibition at 5 µg/ml antibody | ~100% | ~75% | ~75% | ~75% | ~75% | ~75% | ~75% | ~75% | ~25% | ~60% | ~50% | ~100% |

*no sigmoidal dose response curve could be fitted in this case

This assay qualitatively showed that the Fabs obtained from affinity maturation and X-cloning prevent GM-CSF from binding to the GM-CSF receptor alpha chain and therefore retained the blocking mechanism of their parental Fabs. The assay needed to be performed with a concentration of 35 nM (0.5 μg/ml) biotinylated GM-CSF in order to obtain a significant signal in FACS. Therefore 17.5 nM Fab (or 8.75 nM IgG) is theoretically needed to block 50% of the GM-CSF, thus setting a limit for determination of $IC_{50}$ values.

B. Inhibition of GM-CSF Dependent Proliferation of TF-1 by Anti-hGM-CSF Fabs Using Human GM-CSF TF-1 proliferation assay was performed as described in Example 3B. Fab with improved affinities and the parental Fabs as well as monoclonal reference IgGs were analyzed. $IC_{50}$ values were determined from the dose response curves obtained using GraphPad Prism v3.03 software applying a non-linear regression curve fit. Table 6 summarizes the $IC_{50}$ values obtained in these assays.

TABLE 6

$IC_{50}$ values of anti-hGM-CSF Fabs and control IgGs in TF-1 proliferation assay

| | MOR0# | | | | | | | | | | | |
|---|---|---|---|---|---|---|---|---|---|---|---|---|
| | 4251 | 4357 | 4354 | 4350 | 4252 | 4287 | 4290 | 4302 | 3684 | 3929 | Mab215 | BVD2-21C11 |
| $IC_{50}$ (pM) | 463 | 90 | 56 | 82 | 2010 | 3382 | 696 | 10678 | >200000 | >200000 | 4315 | 6560 |
| $IC_{50}$ x-fold improved compared to Mab215 | 9.3 | 47.9 | 77.1 | 52.6 | 2.1 | 1.3 | 6.2 | — | — | — | — | — |
| $IC_{50}$ x-fold improved compared to BVD2-21C11 | 14.2 | 72.9 | 117.1 | 80.0 | 3.2 | 1.9 | 9.4 | — | — | — | 1.5 | — |

In another set of experiments $IC_{50}$ values in the TF-1 proliferation assay were determined for the parental Fab MOR03682, its affinity matured derivatives MOR04283, MOR04297 and the x-cloned variant MOR04342. Table 7 summarizes the $IC_{50}$ values obtained in these assays.

TABLE 7

$IC_{50}$ values of anti-hGM-CSF Fabs in TF-1 proliferation assay

| | MOR0# | | | |
|---|---|---|---|---|
| | 4342 | 4283 | 4297 | 3682 |
| $IC_{50}$ (pM) | 80 | 17293 | 13975 | >200000 |

These experiments demonstrated the large improvements achieved in $IC_{50}$ values after affinity maturation and X-cloning. For example, MOR04357, MOR04350, MOR04354 show >2000fold improved $IC_{50}$ values compared to their parental MOR03929 and exceed the potency of BVD2-21C11 and Mab215

Example 6

Conversion of MOR04357 to Human IgG1 Format

A. Gene Optimization of Fab DNA Sequences for Expression in Mammalian Expression Systems.

To optimize DNA of the VH and VL of MOR04357 for mammalian gene expression (e.g. changing codon usage, GC content, etc.) GeneOptimizer™ software from Geneart (Regensburg, Germany) was utilized to define such optimized VH and VL DNA sequences, which were gene synthesized at Geneart (Regensburg, Germany) and cloned into pPCR-Script vectors yielding 055906pPCR-Script and 055907pPCR-Script. SEQ ID NO: 48 shows the respective VH sequence, while SEQ ID NO: 57 shows the respective VL sequence.

B. Cloning of Fab MOR04357 into Human IgG1 Format and IgG1 Expression

In order to express full length immunoglobulin (Ig), variable domain fragments of the gene optimized heavy (VH) and light chains (VL) were subcloned from the pPCR-Script vectors (Example 5a) into the pMORPH® 2_h_Ig vector series for human IgG1. Codon-optimized VH of MOR04357 was isolated from 055906pPCR-Script via NheI/BlpI digestion and inserted into pMorph2_h_IgG1f master vector cut with the same restriction enzymes. This vector already contained a human gamma 1 constant region. The resulting expression plasmid was termed pMorph2_h_IgG1f_MOR04357_co. Codon-optimized VL of MOR04357 was isolated from 055907pPCR-Script via NheI/HpaI digestion and inserted into pMorph2_h_Iglambda2 master vector cut with the same restriction enzymes. This vector already contained a human lambda constant region. The resulting expression plasmid was termed pM2_h_Iglambda2_MOR04357_co.

C. Transient Expression and Purification of Human IgG

Eukaryotic HKB11 cells were transfected with an equimolar amount of IgG heavy and light chain expression vector DNA. Cell culture supernatant was harvested from 3 to 7 days post transfection. After adjusting the pH of the supernatant to 8.0 and sterile filtration, the solution was subjected to standard protein A affinity chromatography (rProteinA FF or MabSelect SURE, GE Healthcare). Buffer exchange was performed to 1× Dulbcecco's PBS (pH 7.2, Invitrogen) and samples were sterile filtered (0.2 μm). MOR04357 IgG1 was dialysed against 1× Dulbcecco's PBS (pH 6.5, Invitrogen). Purity of IgG was analysed under denaturing, reducing conditions in SDS-PAGE or by using Agilent BioAnalyzer and in native state by SE-HPLC.

D. Determination of Picomolar Affinities Using Solution Equilibrium Titration (SET)

For $K_D$ determination, monomer fractions (at least 90% monomer content, analyzed by analytical SEC; Superdex75, Amersham Pharmacia) of IgG1 were used. Electrochemiluminescence (ECL) based affinity determination in solution and data evaluation were basically performed as described by Haenel et al., 2005 and as described in Example 4B. The $K_D$ values for MOR04357 IgG1 against human recombinant GM-CSF was determined to be 1.1 pM.

E. Determination of Affinities to Rat GM-CSF Using Solution Equilibrium Titration (SET)

Affinity determination to rat GM-CSF was done essentially as described in Example 4D using rat-GM-CSF (Peprotech) as analyte in solution instead of human GM-CSF. Affinities were calculated according to Haenel et al (2005). The $K_D$ value for the MOR04357 IgG1 against rat recombinant GM-CSF was determined to be 130 pM.

Example 7

Characterization of MOR04357 IgG1 Derived from Optimized Anti-Human GM-CSF Fabs

A. Inhibition of GM-CSF Dependent Proliferation of TF-1 by Anti-hGM-CSF IgGs Using Human and Rhesus GM-CSF TF-1 proliferation assay was performed as described in Example 3B. MOR04357 was analyzed in IgG1 format and as control monoclonal reference IgGs were analyzed. $IC_{50}$ values were determined from the dose response curves obtained using GraphPad Prism v3.03 software applying a non-linear regression curve fit. Table 8 summarizes the $IC_{50}$ values obtained in these assays. Three different variants of GM-CSF were used in this assay: Firstly, recombinant human GM-CSF at a concentration of 0.25 ng/ml, produced in E. coli, secondly, culture supernatant from HEK293 which have been transiently transfected with pcDNA-huGM-CSF (see Example 3A), containing recombinant human GM-CSF and thirdly, culture supernatant from HEK293 cells which have been transiently transfected with pcDNA-macGM-CSF (see Example 3A), containing recombinant macaca mulatta (rhesus) GM-CSF. For TF-1 proliferation assays the HEK293 culture supernatants were used as a source of the respective GM-CSF in such dilutions that TF-1 cells showed a similar proliferation as compared to proliferation given at the defined concentration of 0.25 ng/ml purified recombinant human GM-CSF produced in E. coli.

TABLE 8

$IC_{50}$ values of MOR04357 IgG and control IgGs in TF-1 proliferation assay

| | $IC_{50}$ (pM) | | |
|---|---|---|---|
| | human GM-CSF (E. coli) | human GM-CSF (HEK293) | macaca GM-CSF (HEK293) |
| MOR04357 IgG1 | 48 | 11 | 15 |
| 21C11 | 1668 | 144 | 128 |
| Mab215 | 625 | 54 | 190 |

This experiment demonstrated the large improvements achieved in $IC_{50}$ values after affinity maturation and X-cloning where preserved after conversion from Fab to IgG1 format. IgG1 MOR04357 shows >2000fold improved $IC_{50}$ values compared to Fab MOR03929 and exceeds the potency of BVD2-21C11 and Mab215.

REFERENCES

Alvaro-Gracia J M, Zvaifler N J, Brown C B, Kaushansky K, and Firestein G S. (1991). Cytokines in chronic inflammatory arthritis. VI. Analysis of the synovial cells involved in granulocyte-macrophage colony-stimulating factor production and gene expression in rheumatoid arthritis and its regulation by IL-1 and tumor necrosis factor-alpha. J Immunol 146, 3365-3371.

Babior, B. (2000). Phagocytes and oxidative stress. Am J Med 109, 33-44.

Bonfield, T. L., Kavuru, M. S., and Thomassen, M. J. (2002). Anti-GM-CSF titer predicts response to GM-CSF therapy in pulmonary alveolar proteinosis. Clin Immunol 105, 342-350.

Bozinovski, S., Jones, J., Beavitt, S. J., Cook, A. D., Hamilton, J. A., and Anderson, G. P. (2003). Innate immune responses to lipopolysaccharide in mouse lung are suppressed and reversed by neutralization of GM-CSF via repression of TLR-4. Am J Physiol Lung Cell Mol. Physiol.

Broide, D. H. and Firestein, G. S. (1991). Endobronchial allergen challenge in asthma. Demonstration of cellular source of granulocyte macrophage colony-stimulating factor by in situ hybridization. J Clin Invest 88, 1048-1053.

Broide, D. H., Paine, M. M., and Firestein, G. S. (1992). Eosinophils express interleukin 5 and granulocyte macrophage-colony-stimulating factor mRNA at sites of allergic inflammation in asthmatics. J Clin Invest 90, 1414-1424.

Brown, C. B., Pihl, C. E., and Kaushansky, K. (1994). Mapping of human granulocyte-macrophage-colony-stimulating-factor domains interacting with the human granulocyte-macrophage-colony-stimulating-factor-receptor alpha-subunit. Eur J Biochem 225, 873-880.

Burmester, G. R., Stuhlmuller, B., Keyszer, G., and Kinne, R. W. (1997). Mononuclear phagocytes and rheumatoid synovitis. Mastermind or workhorse in arthritis? Arthritis Rheum 40, 5-18.

Campbell, I. K., Bendele, A., Smith, D. A., and Hamilton, J. A. (1997). Granulocyte-macrophage colony stimulating factor exacerbates collagen induced arthritis in mice. Ann Rheum Dis 56, 364-368.

Campbell, I. K., Rich, M. J., Bischof, R. J., Dunn, A. R., Grail, D., and Hamilton, J. A. (1998). Protection from collagen-induced arthritis in granulocyte-macrophage colony-stimulating factor-deficient mice. J Immunol 161, 3639-3644.

Carrieri, P. B., Providera, V., De Rosa, T., Tartaglia, G., Gorga, F., and Perella, O. (1998). Profile of cerebrospinal fluid and serum cytokines in patients with relapsing-remitting multiple sclerosis: a correlation with clinical activity. Immunopharmacol Immunotoxicol. 20, 373-382.

Cebon, J., Nicola, N. A., Ward, M., Gardner, I., Dempsey, P. J., Layton, J. E., Dührsen, U., Burgess, A., Nice, E. C., and Morstyn, G. (1990). Granulocyte-macrophage stimulating factor from human lymphocytes. J Biol Chem 265, 4483-4491.

Chantry, D., Turner, M., Brennan, F., Kingsbury, A., and Feldmann, M. (1990). Granulocyte-macrophage colony stimulating factor induces both HLA-DR expression and cytokine production by human monocytes. Cytokine 2, 60-67.

Chen Y., Wiesmann C., Fuh G., Li B., Christinger H. W., McKay. P, de Vos A. M., Lowman H. B. (1999) Selection and analysis of an optimized anti-VEGF antibody: crystal structure of an affinity-matured Fab in complex with antigen. J Mol. Biol. 293, 865-81.

Cheng, S. S., Lai, J. J., Lukacs, N. W., and Kunkel, S. L. (2001). Granulocyte-macrophage colony stimulating factor up-regulates CCR1 in human neutrophils. J Immunol 166, 1178-1184.

Clark, S. C. and Kamen, R. (1987). The human hematopoietic colony-stimulating factors. Science 236, 1229-1237.

Cook, A. D., Braine, E. L., Campbell, I. K., Rich, M. J., and Hamilton, J. A. (2001). Blockade of collagen-induced arthritis post-onset by antibody to granulocyte-macrophage colony-stimulating factor (GM-CSF): requirement for GM-CSF in the effector phase of disease. Arthritis Res 3, 293-298.

de Groot, R. P., Coffer, P. J., and Koenderman, L. (1998). Regulation of proliferation, differentiation and survival by the IL-3/IL-5/GM-CSF receptor family. Cell Signal. 10, 619-628.

de Vries, E. G., Willemse, P. H., Biesma, B., Stern, A. C., Limburg, P. C., and Vellenga, E. (1991). Flare-up of rheumatoid arthritis during GM-CSF treatment after chemotherapy. Lancet 338, 517-518.

Diederichs, K., Boone, T., and Karplus, P. A. (1991). Novel fold and putative receptor binding site of granulocyte-macrophage colony-stimulating factor. Science 254, 1779-1782.

Drake A. W., Myszka D. G., Klakamp S. L. (2004) Characterizing high-affinity antigen/antibody complexes by kinetic- and equilibrium-based methods. Anal Biochem. 328, 35-43.

Dranoff, G., Crawford, A. D., Sadelain, M., Ream, B., Rashid, A., Bronson, R. T., Dickersin, G. R., Bachurski, C. J., Mark, E. L., Whitsett, J. A., and (1994). Involvement of granulocyte-macrophage colony-stimulating factor in pulmonary homeostasis. Science 264, 713-716.

Friguet B., Chaffotte A. F, Djavadi-Ohaniance L., Goldberg M. E. (1985), Measurements of the true affinity constant in solution of antigen-antibody complexes by enzyme-linked immunosorbent assay. J Immunol Methods. 77, 305-19.

Gasson, J. C., Baldwin, G. C., Sakamoto, K. M., and DiPersio, J. F. (1990a). The biology of human granulocyte-macrophage colony-stimulating factor (GM-CSF). Prog Clin Biol Res 352, 375-384.

Gasson, J. C., Fraser, J. K., and Nimer, S. D. (1990b). Human granulocyte-macrophage colony-stimulating factor (GM-CSF): regulation of expression. Prog Clin Biol Res 338, 27-41.

Gasson, J. C., Kaufman, S. E., Weisbart, R. H., Tomonaga, M., and Golde, D. W. (1986). High-affinity binding of granulocyte-macrophage colony-stimulating factor to normal and leukemic human myeloid cells. Proc Natl Acad Sci USA. 83, 669-673.

Gearing, D. P., King, J. A., Gough, N. M., and Nicola, N. A. (1989). Expression cloning of a receptor for human granulocyte-macrophage colony-stimulating factor. EMBO J. 12, 3667-3676.

Gomez-Cambronero, J., Horn, J., Paul, C. C., and Baumann, M. A. (2003). Granulocyte-macrophage colony-stimulating factor is a chemoattractant cytokine for human neutrophils: involvement of the ribosomal p70 S6 kinase signaling pathway. J Immunol 171, 6846-6855.

Haenel, C., Satzger, M., Della Ducata, D., Ostendorp, R. and Brocks, B. (2005). Characterization of high-affinity antibodies by electrochemiluminescence-based equilibrium titration. Analytical Biochemistry, 339, 1, 182-184.

Hamilton, J. A. (1993). Rheumatoid arthritis: opposing actions of hemopoietic growth factors and slow acting anti-rheumatic drugs. Lancet 342, 536-539.

Hamilton, J. A. (2002). GM-CSF in inflammation and autoimmunity. Trends Immunol 23, 403-408.

Hart, P. H., Whitty, G. A., Piccoli, D. S., and Hamilton, J. A. (1988). Synergistic activation of human monocytes by granulocyte-macrophage colony-stimulating factor and IFN-gamma. Increased TNF-alpha but not IL-1 activity. J Immunol 141, 1516-1521.

Haworth, C., Brennan, F. M., Chantry, D., Turner, M., Maini, R. N., and Feldmann, M. (1991). Expression of granulocyte-macrophage colony-stimulating factor in rheumatoid arthritis: regulation by tumor necrosis factor-alpha. Eur J Immunol 21, 2575-2579.

Hayashida, K., Kitamura, T., Gorman, D. M., Arai, K., Yokota, K., and Miyajima, A. (1990). Molecular cloning of a second subunit of the receptor for human granulocyte-macrophage colony-stimulating factor (GM-CSF): reconstitution of a high-affinity GM-CSF receptor. Proc Natl Acad Sci USA 87, 9655-9659.

Hazenberg B P, Van Leeuwen M A, Van Rijswijk M H, Stern A C, and Vellenga E (1989). Correction of granulocytopenia in Felty's syndrome by granulocyte-macrophage colony-stimulating factor. Simultaneous induction of interleukin-6 release and flare-up of the arthritis. Blood 74, 2769-2780.

Kastelein, R. A. and Shanafelt, A. B. (1993). GM-CSF receptor: interactions and activation. Oncogene 8, 231-236.

Kaufman, S. E., DiPersio, J. F., and Gasson, J. C. (1989). Effects of human GM-CSF on neutrophil degranulation in vitro. Exp Hematol 17, 800-804.

Kitamura, T., Sato, N., Arai, K., and Miyajima, A. (1991). Expression cloning of the human IL-3 receptor cDNA reveals a shared beta subunit for the human IL-3 and GM-CSF receptors. Cell 66, 1165-1174.

Kitamura, T., Tanaka, N., Watanabe, J., Uchida, Kanegasaki, S., Yamada, Y., and Nakata, K. (1999). Idiopathic pulmonary alveolar proteinosis as an autoimmune disease with neutralizing antibody against granulocyte/macrophage colony-stimulating factor. J Exp Med 190, 875-880.

Kitamura T., Tange T., Terasawa T., Chiba S., Kuwaki T., Miyagawa K., Piao Y. F., Miyazono K., Urabe A., Takaku F. (1989). Establishment and characterization of a unique human cell line that proliferates dependently on GM-CSF, IL-3, or erythropoietin J Cell Physiol. 140, 323-34.

Knappik, A., Ge, L., Honegger, A., Pack, P., Fischer, M., Wellnhofer, G., Hoess, A., Wolle, J., Pluckthun, A., and Virnekas, B. (2000). Fully synthetic human combinatorial antibody libraries (HuCAL) based on modular consensus frameworks and CDRs randomized with trinucleotides. J Mol Biol 296, 57-86.

Krebs, B., Rauchenberger, R., Reiffert, S., Rothe, C., Tesar, M., Thomassen, E., Cao, M., Dreier, T., Fischer, D., Hoss, A., Inge, L., Knappik, A., Marget, M., Pack, P., Meng, X. Q., Schier, R., Sohlemann, P., Winter, J., Wolle, J., and Kretzschmar, T. (2001). High-throughput generation and engineering of recombinant human antibodies. J Immunol Methods 254, 67-84.

Lopez, A. F., Williamson, D. J., Gamble, J. R., Begley, C. G., Harlan, J. N., Klebanoff, S. J., Waltersdorph, A., Wong, G., Clark, S. C., and Vadas, M. A. (1986). Recombinant human granulocyte-macrophage colony-stimulating factor stimulates in vitro mature human neutrophil and eosinophil function, surface receptor expression, and survival. J Clin Invest 78, 1220-1228.

McQualter, J. L., Darwiche, R., Ewing, C., Onuki, M., Kay, T. W., Hamilton, J. A., Reid, H. H., and Bernard, C. C.

(2001). Granulocyte macrophage colony-stimulating factor: a new putative therapeutic target in multiple sclerosis. J Exp Med 194, 873-882.

Meager, A., Wadhwa, M., Bird, C., Dilger, P., Thorpe, R., Newsom-Davis, J., and Willcox, N. (1999). Spontaneously occurring neutralizing antibodies against granulocyte-macrophage colony-stimulating factor in patients with autoimmune disease. Immunology 97, 526-532.

Metcalf, D., Begley, C. G., Johnson, G. R., Nicola, N. A., Vadas, M. A., Lopez, A. F., Williamson, D. J., Wong, G. G., Clark, S. C., and Wang, E. A. (1986). Biologic properties in vitro of a recombinant human granulocyte-macrophage colony-stimulating factor. Blood 67, 37-45.

Mulherin, D., Fitzgerald, O., and Bresnihan, B. (1996). Synovial tissue macrophage populations and articular damage in rheumatoid arthritis. Arthritis Rheum 39, 115-124.

Nagy Z. A., Hubner B., Lohning C., Rauchenberger R., Reiffert S., Thomassen-Wolf E., Zahn S., Leyer S., Schier E. M., Zahradnik A., Brunner C., Lobenwein K., Rattel B., Stanglmaier M., Hallek M., Wing M., Anderson S., Dunn M., Kretzschmar T., Tesar M. (2002) Fully human, HLA-DR-specific monoclonal antibodies efficiently induce programmed death of malignant lymphoid cells. Nat. Med. 8, 801-7

Olver, I. N., Hercus, T., Lopez, A., Vadas, M., Somogyi, A. A., Doyle, I., Foster, D. J., Keefe, D., Taylor, A., Brown, M., To, L. B., Cole, J., Rawling, T., Cambareri, B., Myers, M., Olszewski, N., Bastiras, S., Senn, C., Hey, A., Verma, M., and Wigley, P. (2002). A phase I study of the GM-CSF antagonist E21R. Cancer Chemother Pharmacol 50, 171-178.

Plenz, G., Eschert, H., Beissert, S., Arps, V., Sindermann, J. R., Robenek, H., and Völker, W. (2003). Alterations in the vascular extracellular matrix of granulocyte-macrophage colony-stimulating factor (GM-CSF)-deficient mice. FASEB J. 17, 1451-1457.

Rapoport, A. P., Abboud, C. N., and DiPersio, J. F. (1992). Granulocyte-macrophage colony-stimulating factor (GM-CSF) and granulocyte colony-stimulating factor (G-CSF): receptor biology, signal transduction, and neutrophil activation. Blood Rev 6, 43-57.

Rauchenberger, R., Borges, E., Thomassen-Wolf, E., Rom, E., Adar, R., Yaniv, Y., Malka, M., Chumakov, I., Kotzer, S., Resnitzky, D., Knappik, A., Reiffert, S., Prassler, J., Jury, K., Waldherr, D., Bauer, S., Kretzschmar, T., Yayon, A., and Rothe, C. (2003). Human combinatorial Fab Library yielding specific and functional antibodies against the human fibroblast growth factor receptor 3. J Biol. Chem.

Santiago-Schwarz F, Anand P, L. S., and Carsons S E (2001). Dendritic cells (DCs) in rheumatoid arthritis (RA): progenitor cells and soluble factors contained in RA synovial fluid yield a subset of myeloid DCs that preferentially activate Th1 inflammatory-type responses. J Immunol 167, 1758-1768.

Sato, N., Sakamaki, K., Terada, N., Arai, K., and Miyajima, A. (1993). Signal transduction by the high-affinity GM-CSF receptor: two distinct cytoplasmic regions of the common beta subunit responsible for different signaling. EMBO J. 12, 4181-4189.

Schier R., McCall A., Adams G. P, Marshall K. W., Merritt H., Yim M., Crawford R. S., Weiner L. M., Marks C., Marks J. D. (1996) Isolation of picomolar affinity anti-c-erbB-2 single-chain Fv by molecular evolution of the complementarity determining regions in the center of the antibody binding site. J Mol. Biol. 8, 263:551-67.

Shanafelt, A. B., Johnson, K. E., and Kastelein, R. A. (1991a). Identification of critical amino acid residues in human and mouse granulocyte-macrophage colony-stimulating factor and their involvement in species specificity. J Biol Chem 266, 13804-13810.

Shanafelt, A. B., Miyajima, A., Kitamura, T., and Kastelein, R. A. (1991b). The amino-terminal helix of GM-CSF and IL-5 governs high affinity binding to their receptors. EMBO J. 10, 4105-4112.

Shibata, Y., Berclaz, P.-Y., Chroneos, Z., Yoshida, H., and Trapnell, B. C. (2001). GM-CSF regulates alveolar macrophage differentiation and innate immunity in the lung through PU. Immunity 15, 557-567.

Sisson, S. D. and Dinarello, C. A. (1988). Production of interleukin-1 alpha, interleukin-1 beta and tumor necrosis factor by human mononuclear cells stimulated with granulocyte-macrophage colony-stimulating factor. Blood 72, 1368-1374.

Stanley, E., Lieschke, G. J., Grail, D., Metcalf, D., Hodgson, G., Gall, J. A., Maher, D. W., Cebon, J., Sinickas, V., and Dunn, A. R. (1994). Granulocyte/macrophage colony-stimulating factor-deficient mice show no major perturbation of hematopoiesis but develop a characteristic pulmonary pathology. Proc Natl Acad Sci USA 91, 5592-5596.

Trapnell, B. C. and Whitsett, J. A. (2002). GM-CSF regulates pulmonary surfactant homeostasis and alveolar macrophage-mediated innate host defense. Annu Rev Physiol 64, 775-802.

Uchida, K., Nakata, K., Trapnell, B. C., Terakawa, T., Hamano, E., Mikami, A., Matsushita, I., Seymour, J. F., Oh-Eda, M., Ishige, I., Eishi, Y., Kitamura, T., Yamada, Y., Hanaoka, K., and Keicho, N. (2004). High-affinity autoantibodies specifically eliminate granulocyte-macrophage colony-stimulating factor activity in the lungs of patients with idiopathic pulmonary alveolar proteinosis. Blood 103, 1089-1098.

Virnekäs, B., Ge, L., Plückthun, A., Schneider, K. C., Wellnhofer, G. & Moroney, S. E., (1994). Nucleic Acids Research 22, 5600-5607.

Xu, W. D., Firestein, G. S., Taetle, R., Kaushansky, K., and Zvaifler, N. J. (1989). Cytokines in chronic inflammatory arthritis. II. Granulocyte-macrophage colony-stimulating factor in rheumatoid synovial effusions. J Clin Invest 83, 876-882.

Yamashita, N., Tashimo, H., Ishida, H., Kaneko, F., Nakano, J., Kato, H., Horiuchi, T., and Ohta, K. (2002). Attenuation of airway hyperresponsiveness in a murine asthma model by neutralization of GM-CSF. Cell Immunol 219, 92-97.

Yang W. P., Green K., Pinz-Sweeney S., Briones A. T., Burton D. R., Barbas C. F. 3rd. (1995). CDR walking mutagenesis for the affinity maturation of a potent human anti-HIV-1 antibody into the picomolar range. J Mol. Biol. 254, 392-403

Zhang, Y., McCluskey, K., Fujii, K., and Wahl, L. M. (1998). Differential regulation of monocyte matrix metalloproteinase and TIMP-1 production by TNF-alpha, granulocyte-macrophage CSF, and IL-1 beta through prostaglandin-dependent and -independent mechanisms. J Immunol 161, 3071-3076.

The invention claimed is:

1. An isolated human or humanized antibody or functional fragment thereof that is specific for human GM-CSF, wherein said isolated human or humanized antibody or functional fragment thereof is able
   (i) to block interaction of 0.5 μg/ml human GM-CSF with the alpha chain of human GM-CSF receptor expressed on about $2\times10^5$ CHO-K1 cells by at least 50% under the following conditions:
      (a) the concentration of said human GM-CSF receptor alpha chain expressed on said CHO-K1 cells is similar to the concentration of human GM-CSF receptor alpha chain expressed on about $2\times10^5$ CHO-GMRa#11 cells, and
      (b) the concentration of said isolated human or humanized antibody or functional fragment thereof is about 5 μg/ml; and
   (ii) to neutralize 0.25 ng/ml human GM-CSF in a TF-1 proliferation assay with an at least five-fold lower $IC_{50}$ value than reference antibodies MAB215 or BVD2-21C11.

2. An isolated human or humanized antibody according to claim 1, which is an IgG.

3. A pharmaceutical composition comprising an isolated humanized or human antibody or functional fragment thereof according to claim 1, and a pharmaceutically acceptable carrier or excipient therefor.

4. The isolated human or humanized antibody or functional fragment thereof of claim 1, wherein said isolated human or humanized antibody or functional fragment thereof is able to neutralize 0.25 ng/ml human GM-CSF in a TF-1 proliferation assay with an at least 10-fold lower $IC_{50}$ value than the reference antibody MAB215 or BVD2-21C11.

5. The isolated human or humanized antibody or functional fragment thereof of claim 4, wherein said isolated human or humanized antibody or functional fragment thereof is able to neutralize 0.25 ng/ml human GM-CSF in a TF-1 proliferation assay with an at least 30-fold lower $IC_{50}$ value than the reference antibody MAB215 or BVD2-21C11.

* * * * *